(12) United States Patent
Wang et al.

(10) Patent No.: US 12,173,296 B2
(45) Date of Patent: Dec. 24, 2024

(54) METHOD FOR USING PLANT HETEROSIS

(71) Applicant: China National Rice Research Institute, Zhejiang (CN)

(72) Inventors: Kejian Wang, Zhejiang (CN); Chun Wang, Zhejiang (CN)

(73) Assignee: China National Rice Research Institute, Zhejiang (CN)

( * ) Notice: Subject to any disclaimer, the term of this patent is extended or adjusted under 35 U.S.C. 154(b) by 529 days.

(21) Appl. No.: 17/046,794

(22) PCT Filed: Mar. 6, 2019

(86) PCT No.: PCT/CN2019/077154
§ 371 (c)(1),
(2) Date: Oct. 11, 2020

(87) PCT Pub. No.: WO2019/196576
PCT Pub. Date: Oct. 17, 2019

(65) Prior Publication Data
US 2021/0363537 A1    Nov. 25, 2021

(30) Foreign Application Priority Data

Apr. 12, 2018  (CN) .......................... 201810325528.4
Oct. 16, 2018  (CN) .......................... 201811205889.1

(51) Int. Cl.
*C12N 15/82*    (2006.01)
*C07K 14/415*   (2006.01)

(52) U.S. Cl.
CPC ........ *C12N 15/8216* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 2014/0090099 A1 | 3/2014 | Chan et al. | |
| 2014/0298507 A1* | 10/2014 | Chan et al. ............ | A01H 4/005 800/298 |
| 2017/0067067 A1 | 3/2017 | Chintamanani et al. | |
| 2019/0200554 A1* | 7/2019 | Caldo et al. ....... | C12N 15/8261 |

FOREIGN PATENT DOCUMENTS

| | | |
|---|---|---|
| CN | 102308000 A | 1/2012 |
| CN | 103597080 A | 2/2014 |
| CN | 105821074 A | 8/2016 |
| CN | 106661589 A | 5/2017 |
| CN | 106755077 A | 5/2017 |
| CN | 107298702 A | 10/2017 |
| CN | 108503700 A | 9/2018 |
| CN | 109982560 A | 7/2019 |
| WO | 2017087682 A | 5/2017 |
| WO | 2017161264 A1 | 9/2017 |

OTHER PUBLICATIONS

Mieulet et al. (1016) Cell Res. 26:242-54.*
Mieulet et al. (2016) Cell Res 26:1242-54.*
Yamada (1988) Mol Microbiol 2(3):405-12.*
Whisstock & Lesk (2003) Q Rev Biophys. 36(3):307-40.*
Guo et al. (2004) Proc Natl Acad Sci USA 101:9205-10.*
XP_015638092.1 (2018) NCBI.*
NP-001410824.1 (2023) NCBI.*
Mangwhar et al. (2019) 24(12): 1102-25.*
Wang et al. (2019) Nat Biotech 37:283-87.*
Gao (2021) Cell 184:1621-35.*
Zhu et al. (2020) Nat Rev Mol Cell Biol 21:661-77.*
Mieulet, D. et al. "Turning Rice Meiosis into Mitosis". Cell Research, vol. 26. Oct. 21, 2016 (Oct. 21, 2016), ISSN:1001-0602. pp. 1242-1254.
Matrilineal, A sperm-specific phospholipase, triggers maize haploid induction, LETTER, doi: 10.1038/nature20827.
The extended European search report of the corresponding EP patent application No. 19784291.7, mail date Jan. 4, 2022.
L. Brownfield et al: "Unreduced gamete formation in plants: mechanisms and prospects", Journal of Experimental Botany, vol. 62, No. 5, Nov. 25, 2010 (Nov. 25, 2010), pp. 1659-1668, XP055228862, GB ISSN: 0022-0957, DOI: 10.1093/jxb/erq371 p. 1663, col. 2, paragraph 2-p. 1666, col. 1, paragraph 1; figure 2.
Ma Xingliang et al: "A Robust CRISPR/Cas 9 System for Convenient, High-Efficiency Multiplex Genome Editing in Monocot and Dicot Plants", Molecular Plant, vol. 8, No. 8, Aug. 1, 2015(Aug. 1, 2015), pp. 1274-1284, XP 055822799, ISSN: 1674-2052, SOI: 10.1016/j.molp.2015.04.007.
Kandemir Nejdet et al: "Apomixis: new horizons in plant breeding", Turkish Journal of Agriculture and Forestry, vol. 39, Jan. 1, 2015(Jan. 1, 2015), pp. 549-556, XP055871784, TR ISSN: 1300-011X, DOI : 10.3906/tar/-1409-74 Retrieved from the internet: URL: https://journals. tubitak.gov.tr/agriculture/issues/tar-15-39-4/tar-39-4-3-1409-74.
Wang Chun et al:"Clonal seeds from hybrid rice by simultaneous genome engineering of meiosis and fertilization genes", Nature Biotechnology, Nature Publishing Group US, New York, vol. 37, No. 3, Jan. 4, 2019(Jan. 4, 2019), pp. 283-286, XP036717134, ISSN: 1087-0156, DOI: 10.1038/S41587-018-0003-0.
The Examination report No. 1 for the AU standard patent application No. 2019250836, mail date Jan. 27, 2022.
Turning Meiosis into Mitosis, Isabelle d'Erfurth et al. PLoS Biology, vol. 7, issue 6, e1000124, (2009).
Synthetic Clonal Reproduction Through Seeds, Mohan P. A. Marimuthu et al. Science, vol. 331, pp. 876 (2011).

\* cited by examiner

*Primary Examiner* — Russell T Boggs
(74) *Attorney, Agent, or Firm* — Samson G. Yu

(57) ABSTRACT

The present disclosure discloses a method for using plant heterosis. The method comprises the following steps: S1, transforming the meiosis of germ cells of hybrids into mitosis-like so as to obtain gametes whose genotype and chromosome ploidy are consistent with hybrids by using gene mutation or gene engineering technology; and S2, influencing and involving in the development of gametes or embryos in plants by using gene mutation and gene engineering technology, wherein a protein involved is MTL protein.

4 Claims, 5 Drawing Sheets

Specification includes a Sequence Listing.

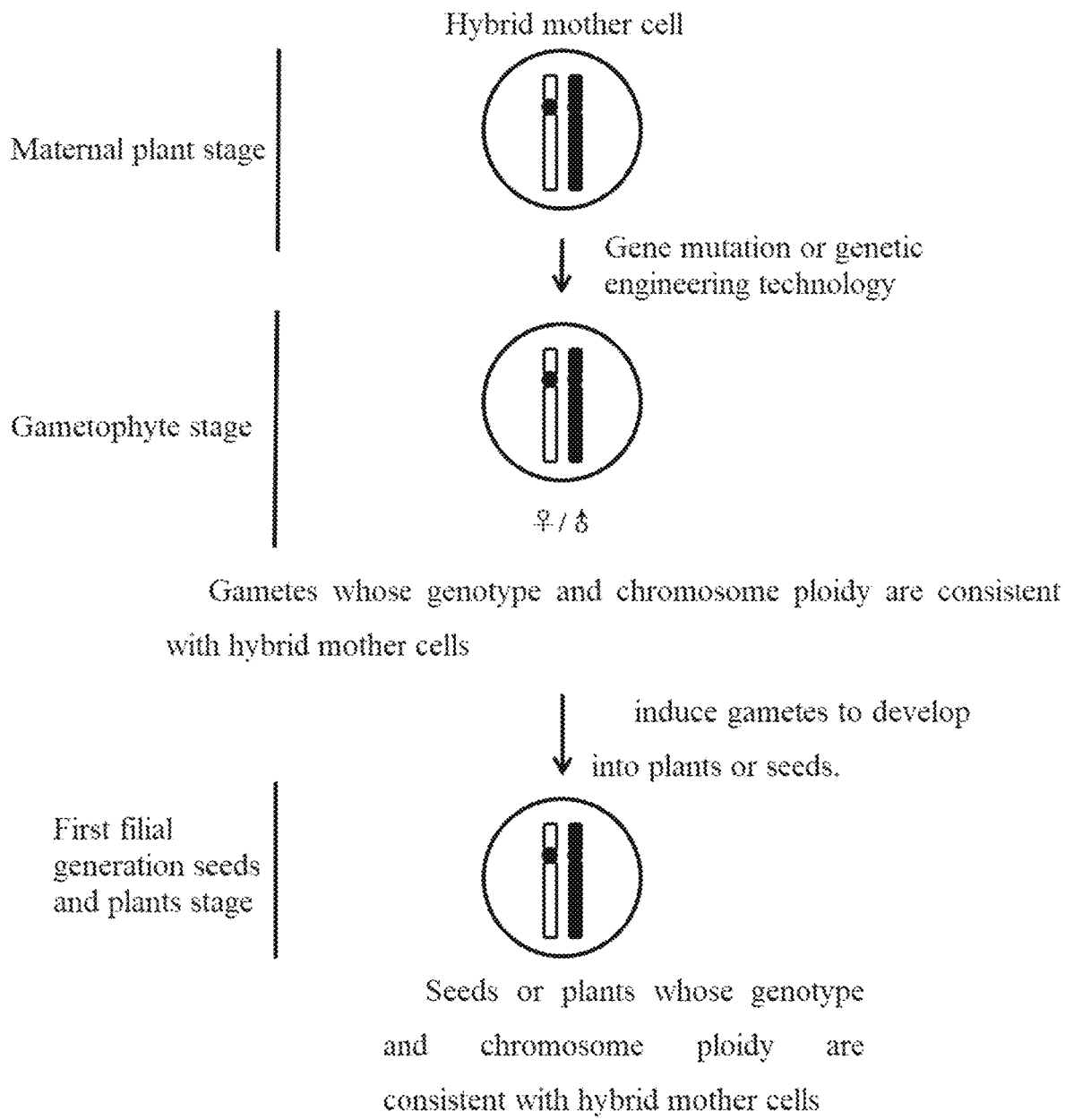

Fig.3
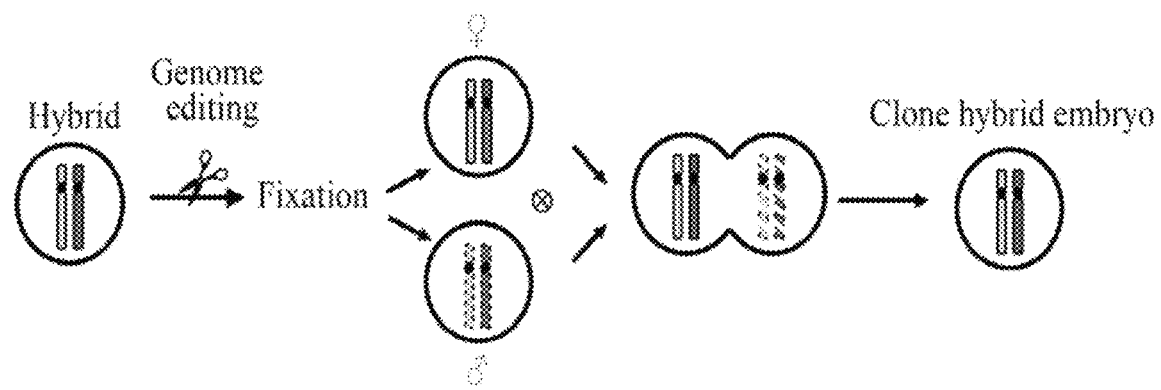
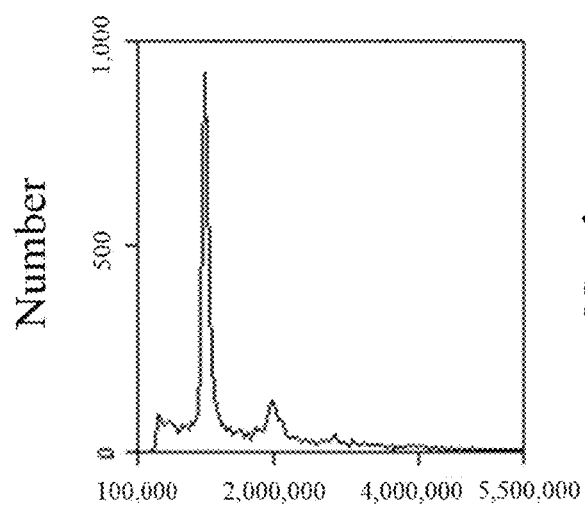
Fig.4A
Chunyou84
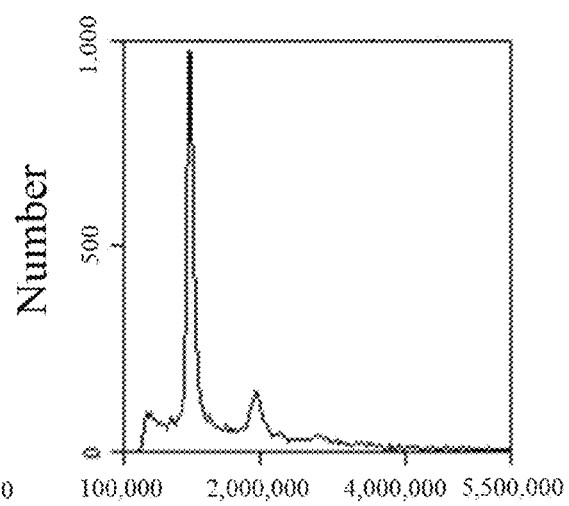
Fig. 4B
Genotype and chromosome ploidy fixed plants

SEQUENCE LISTING

```
<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: OSD1 gene knockout site
<220> FEATURE:
<221> NAME/KEY: primer_bind
<222> LOCATION: (20)..(22)
<223> OTHER INFORMATION: PAM Sequence

<400> SEQUENCE: 1
ctgccgccga cgagcaacaa gg                                            22

<210> SEQ ID NO 2
<211> LENGTH: 22
<212> TYPE: DNA
<213> ORGANISM: Artificial Sequence
<220> FEATURE:
```

```
<223> OTHER INFORMATION: PAIR1 gene knockout site
<220> FEATURE:
<221> NAME/KEY: primer_bind
<222> LOCATION: (20)..(22)
<223> OTHER INFORMATION: PAM Sequence

<400> SEQUENCE: 2
aagcaaccca gtgcaccgct gg                                         22

<210> SEQ ID NO 3
<211> LENGTH: 22
<212> TYPE: DNA
<213> ORGANISM: Artificial Sequence
<220> FEATURE:
<223> OTHER INFORMATION: REC8 gene knockout site
<220> FEATURE:
<221> NAME/KEY: primer_bind
<222> LOCATION: (20)..(22)
<223> OTHER INFORMATION: PAM Sequence

<400> SEQUENCE: 3
cccatggcac taaggctctc cg                                         22

<210> SEQ ID NO 4
<211> LENGTH: 22
<212> TYPE: DNA
<213> ORGANISM: Artificial Sequence
<220> FEATURE:
<223> OTHER INFORMATION: MTL gene knockout site
<220> FEATURE:
<221> NAME/KEY: primer_bind
<222> LOCATION: (20)..(22)
<223> OTHER INFORMATION: PAM Sequence

<400> SEQUENCE: 4
ggtcaacgtc gagaccggca gg                                         22

<210> SEQ ID NO 5
<211> LENGTH: 23
<212> TYPE: DNA
<213> ORGANISM: Artificial Sequence
<220> FEATURE:
<223> OTHER INFORMATION: Primer OSD1-F

<400> SEQUENCE: 5
atctccagga tgcctgaagt gag                                        23

<210> SEQ ID NO 6
<211> LENGTH: 26
<212> TYPE: DNA
<213> ORGANISM: Artificial Sequence
<220> FEATURE:
<223> OTHER INFORMATION: Primer OSD1-R

<400> SEQUENCE: 6
cctagactgc tactcttgct agtgat                                     26

<210> SEQ ID NO 7
<211> LENGTH: 24
<212> TYPE: DNA
<213> ORGANISM: Artificial Sequence
<220> FEATURE:
<223> OTHER INFORMATION: Primer PAIR1-F

<400> SEQUENCE: 7
ctgtacctgt gcatctaatt acag                                       24
```

```
<210> SEQ ID NO 8
<211> LENGTH: 27
<212> TYPE: DNA
<213> ORGANISM: Artificial Sequence
<220> FEATURE:
<223> OTHER INFORMATION: Primer PAIR1-R

<400> SEQUENCE: 8
ccccatctta tgtactgagc ttgccag                                           27

<210> SEQ ID NO 9
<211> LENGTH: 22
<212> TYPE: DNA
<213> ORGANISM: Artificial Sequence
<220> FEATURE:
<223> OTHER INFORMATION: Primer REC8-F

<400> SEQUENCE: 9
gcgacgcttc actcgaagat ca                                                22

<210> SEQ ID NO 10
<211> LENGTH: 22
<212> TYPE: DNA
<213> ORGANISM: Artificial Sequence
<220> FEATURE:
<223> OTHER INFORMATION: Primer REC8-R

<400> SEQUENCE: 10
cgccatgcct cgttgatctc aa                                                22

<210> SEQ ID NO 11
<211> LENGTH: 24
<212> TYPE: DNA
<213> ORGANISM: Artificial Sequence
<220> FEATURE:
<223> OTHER INFORMATION: Primer MTL-F

<400> SEQUENCE: 11
acagtgacta gtgacaaacg atcg                                              24

<210> SEQ ID NO 12
<211> LENGTH: 25
<212> TYPE: DNA
<213> ORGANISM: Artificial Sequence
<220> FEATURE:
<223> OTHER INFORMATION: Primer MTL-R

<400> SEQUENCE: 12
gatcgcgtca gcatgatgcg tgtac                                             25

<210> SEQ ID NO 13
<211> LENGTH: 492
<212> TYPE: PRT
<213> ORGANISM: Plant

<400> SEQUENCE: 13
```

| Met | Lys | Leu | Lys | Met | Asn | Lys | Ala | Cys | Asp | Ile | Ala | Ser | Ile | Ser | Val |
|---|---|---|---|---|---|---|---|---|---|---|---|---|---|---|---|
| 1 | | | | 5 | | | | | 10 | | | | | 15 | |

| Leu | Pro | Pro | Arg | Arg | Thr | Gly | Gly | Ser | Ser | Gly | Ala | Ser | Ala | Ser | Gly |
|---|---|---|---|---|---|---|---|---|---|---|---|---|---|---|---|
| | | | 20 | | | | | 25 | | | | | 30 | | |

| Ser | Val | Ala | Val | Ala | Val | Ala | Ser | Gln | Pro | Arg | Ser | Gln | Pro | Leu | Ser |
|---|---|---|---|---|---|---|---|---|---|---|---|---|---|---|---|
| | | 35 | | | | | 40 | | | | | 45 | | | |

| Gln | Ser | Gln | Gln | Ser | Phe | Ser | Gln | Gly | Ala | Ser | Ala | Ser | Leu | Leu | His |
|---|---|---|---|---|---|---|---|---|---|---|---|---|---|---|---|
| 50 | | | | | 55 | | | | | 60 | | | | | |

```
Ser Gln Ser Gln Phe Ser Gln Val Ser Leu Asp Asn Leu Leu Thr
 65                  70                  75                  80

Leu Leu Pro Ser Pro Thr Arg Asp Gln Arg Phe Gly Leu His Asp Asp
                 85                  90                  95

Ser Ser Lys Arg Met Ser Ser Leu Pro Ala Ser Ser Ala Ser Cys Ala
            100                 105                 110

Arg Glu Glu Ser Gln Leu Gln Leu Ala Lys Leu Pro Ser Asn Pro Val
            115                 120                 125

His Arg Trp Asn Pro Ser Ile Ala Asp Thr Arg Ser Gly Gln Val Thr
            130                 135                 140

Asn Glu Asp Val Glu Arg Lys Phe Gln His Leu Ala Ser Ser Val His
145                 150                 155                 160

Lys Met Gly Met Val Val Asp Ser Val Gln Ser Asp Val Met Gln Leu
                165                 170                 175

Asn Arg Ala Met Lys Glu Ala Ser Leu Asp Ser Gly Ser Ile Arg Gln
                180                 185                 190

Lys Ile Ala Val Leu Glu Ser Ser Leu Gln Gln Ile Leu Lys Gly Gln
            195                 200                 205

Asp Asp Leu Lys Ala Leu Phe Gly Ser Ser Thr Lys His Asn Pro Asp
210                 215                 220

Gln Thr Ser Val Leu Asn Ser Leu Gly Ser Lys Leu Asn Glu Ile Ser
225                 230                 235                 240

Ser Thr Leu Ala Thr Leu Gln Thr Gln Met Gln Ala Arg Gln Leu Gln
                245                 250                 255

Gly Asp Gln Thr Thr Val Leu Asn Ser Asn Ala Ser Lys Ser Asn Glu
            260                 265                 270

Ile Ser Ser Thr Leu Ala Thr Leu Gln Thr Gln Met Gln Ala Asp Ile
            275                 280                 285

Arg Gln Leu Arg Cys Asp Val Phe Arg Val Phe Thr Lys Glu Met Glu
            290                 295                 300

Gly Val Val Arg Ala Ile Arg Ser Val Asn Ser Arg Pro Ala Ala Met
305                 310                 315                 320

Gln Met Met Ala Asp Gln Ser Tyr Gln Val Pro Val Ser Asn Gly Trp
                325                 330                 335

Thr Gln Ile Asn Gln Thr Pro Val Ala Ala Gly Arg Ser Pro Met Asn
            340                 345                 350

Arg Ala Pro Val Ala Ala Gly Arg Ser Arg Met Asn Gln Leu Pro Glu
            355                 360                 365

Thr Lys Val Leu Ser Ala His Leu Val Tyr Pro Ala Lys Val Thr Asp
            370                 375                 380

Leu Lys Pro Lys Val Glu Gln Gly Lys Val Lys Ala Ala Pro Gln Lys
385                 390                 395                 400

Pro Phe Ala Ser Ser Tyr Tyr Arg Val Ala Pro Lys Gln Glu Glu Val
                405                 410                 415

Ala Ile Arg Lys Val Asn Ile Gln Val Pro Ala Lys Lys Ala Pro Val
            420                 425                 430

Ser Ile Ile Ile Glu Ser Asp Asp Ser Glu Gly Arg Ala Ser Cys
            435                 440                 445

Val Ile Leu Lys Thr Glu Thr Gly Ser Lys Glu Trp Lys Val Thr Lys
            450                 455                 460

Gln Gly Thr Glu Glu Gly Leu Glu Ile Leu Arg Arg Ala Arg Lys Arg
465                 470                 475                 480

Arg Arg Arg Glu Met Gln Ser Ile Val Leu Ala Ser
```

485         490

<210> SEQ ID NO 14
<211> LENGTH: 609
<212> TYPE: PRT
<213> ORGANISM: Plant

<400> SEQUENCE: 14

Met Val Met Ala Gln Lys Thr Lys Glu Ala Glu Ile Thr Glu Gln Asp
1               5                   10                  15

Ser Leu Leu Leu Thr Arg Asn Leu Leu Arg Ile Ala Ile Tyr Asn Ile
            20                  25                  30

Ser Tyr Ile Arg Gly Leu Phe Pro Glu Lys Tyr Phe Asn Asp Lys Ser
        35                  40                  45

Val Pro Ala Leu Glu Met Lys Ile Lys Lys Leu Met Pro Met Asp Thr
    50                  55                  60

Glu Ser Arg Arg Leu Ile Asp Trp Met Glu Lys Gly Val Tyr Asp Ala
65                  70                  75                  80

Leu Gln Lys Lys Tyr Leu Lys Thr Leu Leu Phe Cys Ile Cys Glu Lys
                85                  90                  95

Glu Glu Gly Pro Met Ile Glu Glu Tyr Ala Phe Ser Phe Ser Tyr Pro
            100                 105                 110

Asn Thr Ser Gly Asp Glu Val Ala Met Asn Leu Ser Arg Thr Gly Ser
        115                 120                 125

Lys Lys Asn Ser Ala Thr Phe Lys Ser Asn Ala Ala Glu Val Thr Pro
    130                 135                 140

Asp Gln Met Arg Ser Ser Ala Cys Lys Met Ile Arg Thr Leu Val Ser
145                 150                 155                 160

Leu Met Arg Thr Leu Asp Gln Met Pro Glu Glu Arg Thr Ile Leu Met
                165                 170                 175

Lys Leu Leu Tyr Tyr Asp Asp Val Thr Pro Glu Asp Tyr Glu Pro Pro
            180                 185                 190

Phe Phe Lys Cys Cys Ala Asp Asn Glu Ala Ile Asn Ile Trp Asn Lys
        195                 200                 205

Asn Pro Leu Lys Met Glu Val Gly Asn Val Asn Ser Lys His Leu Val
    210                 215                 220

Leu Ala Leu Lys Val Lys Ser Val Leu Asp Pro Cys Asp Asp Asn Asn
225                 230                 235                 240

Val Asn Ser Glu Asp Asp Asn Met Ser Leu Asp Asn Glu Ser Asp Gln
                245                 250                 255

Asp Asn Asp Phe Ser Asp Thr Glu Val Arg Pro Ser Glu Ala Glu Arg
            260                 265                 270

Tyr Ile Val Ala Pro Asn Asp Gly Thr Cys Lys Gly Gln Asn Gly Thr
        275                 280                 285

Ile Ser Glu Asp Asp Thr Gln Asp Pro Val His Glu Glu Leu Thr
    290                 295                 300

Ala Gln Val Arg Glu Trp Ile Cys Ser Arg Asp Thr Glu Ser Leu Glu
305                 310                 315                 320

Val Ser Asp Val Leu Val Asn Phe Pro Asp Ile Ser Met Glu Met Val
                325                 330                 335

Glu Asp Ile Met Glu Arg Leu Leu Lys Asp Gly Leu Leu Ser Arg Ala
            340                 345                 350

Lys Lys Asp Ser Tyr Ser Val Asn Lys Ile Ala Asp Pro Thr Thr Pro
        355                 360                 365

```
His Ile Lys Lys Glu Val Ile Met Gln Asn Val Ser Pro Thr Glu Gly
    370                 375                 380

Thr Lys Asn Ser Asn Gly Asp Leu Met Tyr Met Lys Ala Leu Tyr His
385                 390                 395                 400

Ala Leu Pro Met Asp Tyr Val Ser Val Gly Lys Leu His Gly Lys Leu
                405                 410                 415

Asp Gly Glu Ala Ser Gln Asn Met Val Arg Lys Leu Ile Glu Lys Met
            420                 425                 430

Val Gln Asp Gly Tyr Val Lys Asn Ser Ala Asn Arg Leu Gly Lys
        435                 440                 445

Ala Val Ile His Ser Glu Val Thr Asn Arg Lys Leu Leu Glu Ile Lys
450                 455                 460

Lys Ile Leu Glu Val Asp Ile Ala Glu Gln Met Ala Ile Asp Thr Asn
465                 470                 475                 480

Ala Glu Pro Gly Glu Pro Glu Arg Lys Asp His Leu Ser Gly His Glu
                485                 490                 495

Met Arg Asp Gly Ser Thr Met Gly Cys Leu Gln Ser Val Gly Ser Asp
            500                 505                 510

Leu Thr Arg Thr Arg Glu Leu Pro Glu Pro Gln Gln Asn Val Ser Met
        515                 520                 525

Gln Ser Gly Gln Glu Ala Ser Thr Val Asp Lys Asp Pro Ser Arg Thr
530                 535                 540

Pro Thr Ser Val Arg Glu Ala Ser Val Cys Ser Leu Glu Ser Gly Val
545                 550                 555                 560

Leu Gly Gln Lys Val Arg Lys Ser Leu Ala Gly Ala Gly Gly Thr Gln
                565                 570                 575

Cys Ser Gln Asp Lys Arg Phe Arg Lys Ala Ser Thr Val Lys Glu Pro
            580                 585                 590

Ile Leu Gln Tyr Val Lys Arg Gln Lys Ser Gln Val Gln Val Gln Val
        595                 600                 605
Gln

<210> SEQ ID NO 15
<211> LENGTH: 844
<212> TYPE: PRT
<213> ORGANISM: Plant

<400> SEQUENCE: 15

Met Glu Val Glu Leu Thr Asn Ile Gln Lys Ala Thr Ser Ser Asp Tyr
1               5                   10                  15

Trp Ser Leu Ala Ser Asn Gln Tyr Pro Cys Gly Lys Phe Pro Lys Val
            20                  25                  30

Ser Val Gly Val Thr Ile Pro Arg Thr Ser Ser Val Ser Arg Gly Arg
        35                  40                  45

Asp Ala Ala Ser Thr Ala Ala Phe Glu Lys Asn Leu Ser Gln Gly Thr
    50                  55                  60

Asp Gly Arg Ser Arg Pro Pro Lys Met Asp Asn Ala Ser Leu Gln Val
65                  70                  75                  80

Ser Pro Glu Ala Ala Asn His Gly Gly Ser Ala Lys Glu Val Pro Lys
                85                  90                  95

Pro Val Pro Ala Lys Val Ser Val Ser Gln Pro Asp Asp Asn Ala Ile
            100                 105                 110

Glu Gln Thr Gly Thr Phe Ser Phe Gly Thr Arg Arg Glu Gln Asp Ser
        115                 120                 125
```

```
His Leu Asp Gln Leu Asp Arg Pro Leu Val Ser Ser Gln Gly Lys
130                 135                 140

Arg Gln Val Glu Ser Ala Asp Lys Asn Lys Pro Asn Ser Glu Met Leu
145                 150                 155                 160

Arg Met Lys Leu Trp Glu Ile Leu Gly Gly Thr Ser Gln Asn Lys Glu
                165                 170                 175

Ala Val Ala Ser Pro Asn Pro Glu Asp Ile Glu Thr Pro Cys Gln Pro
            180                 185                 190

Lys Ser Gln Ile Ala Asn Gly Pro Ser Ser Gly Arg Gln Lys Val Phe
        195                 200                 205

Thr Ser Pro Val Pro Tyr Asn Ile Lys Thr Pro Ala Gln Phe Asn Ser
210                 215                 220

Gln Thr Ala Asn Lys Pro Ser Ser Asp Pro Ile Glu Ser Asp Ser Asp
225                 230                 235                 240

Ser Pro Gln Val Val Glu Val Arg Pro Ile Thr Arg Ser Leu Gly Arg
                245                 250                 255

Lys Lys Glu Pro Thr Gly Ser Thr His Gln Asp Lys Ser Gly Ser Ala
            260                 265                 270

Lys Lys Pro Leu Ser Thr His Arg Ser Thr Pro Lys Gln Lys Ile Leu
        275                 280                 285

Asp Asn Val Phe Ala Phe Asn Asp Lys Cys Thr Pro Lys Thr Val Gly
290                 295                 300

Lys Ser Ala Asn Gly Glu Ser Gly Ser Leu Arg Asn Leu Arg Ser Leu
305                 310                 315                 320

Ser Arg Arg Ala Lys Val Glu Pro Lys Lys Ala His Cys Ser Asp Arg
                325                 330                 335

Ile Ser His Lys Thr Thr Gln Asp Asp Met Glu Arg Lys Val Pro Ser
            340                 345                 350

Lys Tyr Ile Pro Ser Glu Lys Lys Gly Glu Lys Thr Asn Ser Phe Ser
        355                 360                 365

Ser Leu Ser Arg Thr Gly Lys Thr Ala Glu Ser Cys Ser Arg Ser Pro
370                 375                 380

Lys Arg Glu Arg Val Asn Thr Met Ala Asn Val Gly Ala Arg Lys
385                 390                 395                 400

Met Gln Leu Ser Glu Asn Leu Leu Val Lys Thr Leu Asn Asp Gly Glu
                405                 410                 415

His Lys Leu Ser Ser Pro Gln Leu Thr Ser Phe Lys Ser Lys Gly Lys
            420                 425                 430

Cys Ser Ser Ile Ser Pro Gln Gln Lys Glu Asn Asp Asn Thr His Ile
        435                 440                 445

Pro Glu Ala Ser Asp Arg Thr Ala Ala Arg Asn Ser Phe Asn Ser Thr
450                 455                 460

Pro Ser Pro Ala Ala Asn Pro Ser Pro Val Leu Arg Lys Tyr Ser Trp
465                 470                 475                 480

Glu His Asp Glu Asn Pro Ala Ile Asn Gly Lys Ser Gly Gln Lys Asp
                485                 490                 495

Ala Ser Pro Leu Ala Asp Arg Phe Ser Asp Met Pro Asp Asp Phe Ala
            500                 505                 510

Ser Pro Thr Phe Ala Ala Asn Ile Lys Ile Ser Pro His Arg Ser Lys
        515                 520                 525

Met Leu Asp Asp Asp Leu Phe Ser Ser Lys Tyr Pro Lys Gly Val Asn
530                 535                 540

Arg Ser Arg Ser Thr Ser Phe Thr Ser Asp Pro Glu Ser Glu Pro Leu
```

```
                    545                 550                 555                 560
Asp Lys Met Glu Lys Thr Asn Glu Leu Pro Gly Ser Glu Ser Pro Asn
                565                 570                 575
Ser Gln Glu Glu Arg Gln Asn Arg Lys Gln Pro His Leu Ser Pro Leu
                580                 585                 590
Ser Pro Ile Glu Ser Glu Gly Ala Gln Ile Ser Ile Pro Ser Phe Arg
                595                 600                 605
Lys Gly Tyr Lys Ser His Lys Trp Leu Ser Asp Val Asp Ser Pro Asp
                610                 615                 620
Lys Ser Ser Ile Glu His Leu Gly Arg Lys Ser His Leu Lys Glu Gly
625                 630                 635                 640
Arg Lys Gly Lys Arg Gln Leu Thr Ser Pro Thr His Phe Ala Thr Ser
                645                 650                 655
Gly Thr Gln Glu Thr Met Ser Asp Lys Glu Pro Glu Lys Val Pro Glu
                660                 665                 670
Asn Tyr Leu Thr Arg Ala Phe Asp Gln Leu Val Val Val Leu Gly Arg
                675                 680                 685
Phe Gln Thr Lys Ile Lys Ser Glu Thr Arg Asn Lys Ser Ser Lys Ile
                690                 695                 700
Leu Ala Ala Thr Gly Glu Ile Ile Arg Gln His Leu Glu Gly Val Glu
705                 710                 715                 720
Gly Gln Met Gln Ala Asp Val Asp Lys Leu Val Asn Ala Gly Lys Ser
                725                 730                 735
Lys Arg Lys Arg Leu Glu Ser Thr Phe Glu Glu Gln Glu Lys Leu
                740                 745                 750
Arg Ile Leu His Glu Lys Phe Lys Glu Val Asn Gln Gln Leu Leu
                755                 760                 765
Gly Cys Lys Asn Ser Val Glu Asp Phe Glu Ala Tyr His Ala Glu Leu
                770                 775                 780
Lys Gly Val Ala Asp Lys Gln Lys Ala Ser His Lys Lys Leu Leu Gln
785                 790                 795                 800
Asn Ala Glu Lys Thr Val Gly Ala Gln Leu Ser Asp Ala Glu Thr Lys
                805                 810                 815
Ile Ala Glu Val Gln Lys Arg Ala Arg Lys Arg Met Lys Gly Leu Lys
                820                 825                 830
Phe Val Leu Lys Glu Leu Ile Ala Glu Thr Ala Glu
                835                 840

<210> SEQ ID NO 16
<211> LENGTH: 1193
<212> TYPE: PRT
<213> ORGANISM: Plant

<400> SEQUENCE: 16

Met Glu Met Val Leu Ile Met Ser Phe Arg Val Leu Leu Tyr His Arg
1               5                   10                  15
Leu Thr Ala Gln Thr Gly Pro Phe Lys Leu His Cys Leu Gly Ile Leu
                20                  25                  30
Leu Asn Ser Thr Lys Asp Ala Ala Thr Tyr Ile Gly Asp Lys Gln Ser
                35                  40                  45
Leu Tyr Leu Asn Leu Val Asn Asn Leu Arg Leu Pro Ser Asp Glu Ile
                50                  55                  60
Arg Gly Glu Ile Leu Phe Val Leu Tyr Lys Leu Ser Leu Leu Asn Ala
65                  70                  75                  80
```

-continued

```
Thr Pro Trp Asp Asp Ile Cys Asp Asn Asp Asn Val Asp Leu Ser Ala
                 85                  90                  95

Ile Gly Arg Ser Leu Leu Gln Phe Ser Leu Glu Val Leu Leu Lys Thr
            100                 105                 110

Gln Asn Asp Asp Val Arg Leu Asn Cys Ile Ala Leu Leu Leu Thr Leu
            115                 120                 125

Ala Lys Lys Gly Ala Phe Asp Ile Leu Leu Leu Ser Asp Pro Ser Leu
            130                 135                 140

Ile Asn Ser Ala Glu Ala Glu Asp Asn Val Pro Leu Asn Asp Ser Leu
145                 150                 155                 160

Val Ile Leu Phe Ala Glu Ala Val Lys Gly Ser Leu Leu Ser Thr Asn
                165                 170                 175

Ile Glu Val Gln Thr Gly Thr Leu Glu Leu Ile Phe His Phe Leu Ser
                180                 185                 190

Ser Asp Ala Asn Ile Phe Val Leu Lys Thr Leu Ile Asp Gln Asn Val
            195                 200                 205

Ala Asp Tyr Val Phe Glu Val Leu Arg Leu Ser Gly Met Arg Asn His
            210                 215                 220

Leu Leu Gln Ser Ser Asn Ala Ser Gln Phe Leu Thr Lys Leu Leu Tyr
225                 230                 235                 240

Val Ser Gly Asn Asn Asp Pro Leu Val Ile Ser Ser Ile Lys Val Leu
                245                 250                 255

Ser Ile Leu Ala Asn Ser Glu Glu Arg Phe Lys Glu Lys Leu Ala Ile
            260                 265                 270

Ala Val Ser Thr Leu Leu Pro Val Leu His Tyr Val Ser Glu Ile Pro
            275                 280                 285

Phe His Pro Val Gln Ser Gln Val Leu Arg Leu Val Cys Ile Ser Ile
            290                 295                 300

Ile Asn Cys Ser Gly Ile Leu Ser Leu Ser Gln Glu Glu Gln Ile Ala
305                 310                 315                 320

Cys Thr Leu Ser Ala Ile Leu Arg Arg His Gly Asn Gly Glu Leu Gly
                325                 330                 335

Met Ser Ser Glu Thr Phe Ala Leu Val Cys Ser Met Leu Val Glu Ile
            340                 345                 350

Leu Lys Leu Pro Ser Ala Asp Asp Ile Gln Lys Leu Pro Ser Phe Ile
            355                 360                 365

Val Glu Ala Ser Lys His Ala Ile Ser Leu Thr Phe Ser His Glu Tyr
            370                 375                 380

Asp Cys Leu Phe Leu Ile Pro His Ser Leu Leu Leu Lys Glu Ala
385                 390                 395                 400

Leu Ile Phe Cys Leu Glu Gly Asn Lys Asp Gln Ile Leu Arg Lys Lys
                405                 410                 415

Ser Leu Glu Asp Ser Ile Ile Glu Thr Cys Glu Thr Tyr Leu Leu Pro
            420                 425                 430

Trp Leu Glu Ser Ala Ile Val Asp Gly Asn Asp Glu Glu Thr Leu Ser
            435                 440                 445

Gly Ile Leu Gln Ile Phe Gln Ile Ile Leu Ser Arg Ala Ser Asp Asn
            450                 455                 460

Lys Ser Phe Lys Phe Ala Glu Met Leu Ala Ser Ser Trp Phe Ser
465                 470                 475                 480

Leu Ser Phe Gly Phe Met Gly Leu Phe Pro Thr Asp His Val Lys Ser
                485                 490                 495

Ala Val Tyr Leu Val Ile Ser Ser Ile Val Asp Lys Val Leu Gly Ile
```

-continued

```
                500             505             510
Ser Tyr Gly Glu Thr Ile Arg Asp Ala Cys Ile Tyr Leu Pro Pro Asp
        515             520             525

Pro Ala Glu Leu Leu Tyr Leu Leu Gly Gln Cys Ser Ser Glu Asp Phe
        530             535             540

Asn Leu Ala Ser Cys Gln Cys Ala Ile Leu Val Ile Leu Tyr Val Cys
545             550             555             560

Ser Phe Tyr Asn Glu Arg Leu Ala Ala Asp Asn Gln Ile Leu Ala Ser
                565             570             575

Val Glu Gln Tyr Ile Leu Leu Asn Gly Ala Lys Phe Pro His Glu Ile
                580             585             590

Pro Gly Ser Leu Met Leu Thr Leu Leu Val His Leu Tyr Ala Phe Val
        595             600             605

Arg Gly Ile Ser Phe Arg Phe Gly Ile Pro His Ser Pro Glu Ala Glu
        610             615             620

Lys Thr Leu Phe His Ala Met Thr His Lys Glu Trp Asp Leu Leu Leu
625             630             635             640

Ile Arg Val His Leu Ile Ala Leu Lys Trp Leu Phe Gln Asn Glu Glu
                645             650             655

Leu Met Glu Pro Leu Ser Phe His Leu Leu Asn Phe Cys Lys Phe Phe
                660             665             670

Cys Glu Asp Arg Thr Val Met Leu Ser Ser Thr Gln Leu Val Asp
        675             680             685

Ile Gln Leu Ile Ala Glu Leu Val Tyr Ser Gly Glu Thr Cys Ile Ser
        690             695             700

Ser Leu Leu Val Ser Leu Ser Gln Met Ile Lys Glu Ser Ala Glu
705             710             715             720

Asp Glu Val Leu Ser Val Asn Val Ile Thr Glu Ile Leu Val Ser
                725             730             735

Phe Pro Cys Thr Ser Asp Gln Phe Val Ser Cys Gly Ile Val Asp Ala
        740             745             750

Leu Gly Ser Ile Tyr Leu Ser Leu Cys Ser Ser Arg Ile Lys Ser Val
        755             760             765

Cys Ser Leu Leu Ile Phe Asn Ile Leu His Ser Ala Ser Ala Met Thr
770             775             780

Phe Thr Cys Asp Asp Ala Trp Leu Ala Leu Thr Met Lys Leu Leu
785             790             795             800

Asp Cys Phe Asn Ser Ser Leu Ala Tyr Thr Ser Ser Glu Gln Glu Trp
                805             810             815

Lys Ile Leu Ile Gly Ile Leu Cys Leu Ile Leu Asn His Ser Ala Asn
                820             825             830

Lys Val Leu Ile Glu Pro Ala Lys Ala Ile Ile Leu Asn Asn Cys Leu
        835             840             845

Ala Leu Leu Met Asp Gly Ile Val Gln Glu Ala Cys Ala Lys Gly Pro
850             855             860

Ser Leu Phe Gln His Asn Gln Glu Thr Thr Phe Gly Glu Leu Leu Ile
865             870             875             880

Leu Met Leu Leu Leu Ile Phe Phe Ser Val Arg Ser Leu Gln Ala Ile
                885             890             895

Leu Glu Ala Ser Ile Asp Trp Gln Glu Phe Leu Gln Tyr Ser Asp Asp
                900             905             910

Thr Glu Ser Ser Ser Val Leu Gly Ile Pro Cys His Asp Leu Cys Arg
        915             920             925
```

```
Leu Met His Phe Gly Pro Ser Pro Val Lys Leu Ile Ala Ser Gln Cys
    930                 935                 940

Leu Leu Glu Leu Leu Asn Arg Ile Ser Asp Gln Arg Ser Cys Leu Asn
945                 950                 955                 960

Ala Glu Leu Arg Cys Ser Ala Lys Tyr Leu Lys Ser Met Ile Ala Val
                965                 970                 975

Thr Glu Gly Met Val Phe Asp Gln Asp Ser Arg Val Ala Glu Asn Cys
            980                 985                 990

Gly Ala Cys Leu Thr Val Ile Leu Gly Trp Glu Arg Phe Gly Ser Arg
        995                 1000                1005

Glu Lys Ala Val Ile Arg Glu Ser Lys Trp Ser Arg Leu Ile Leu
    1010                1015                1020

Glu Glu Phe Ala Val Ala Leu Thr Ala Pro Gly Leu Thr Ser Lys
    1025                1030                1035

Ser Phe Ser Asn Gln Gln Lys Ile Ala Ala Asn Ile Ala Leu Ser
    1040                1045                1050

Leu Leu Gln Leu Ser Gln Val Pro Asp Trp Leu Thr Ser Leu Phe
    1055                1060                1065

Ser Asp Ser Leu Ile Ser Gly Ile Val Ala Asn Leu Ser Ala Arg
    1070                1075                1080

Asn Val Thr Ala Glu Ile Val Thr Leu Phe Ser Glu Leu Met Ala
    1085                1090                1095

Lys Asn Tyr Leu Asn Gln Glu His Ile Ala Gly Leu His Asn Leu
    1100                1105                1110

Phe Gln Val Cys Arg Arg Gln Ala Tyr Glu Gly Gly Gly Gly Ser
    1115                1120                1125

Lys Ala Gln Pro Ser Glu Gln Lys Ala Ala Ala Ala Arg Cys Ala
    1130                1135                1140

Asp Asp Val Arg Ala Leu Leu Phe Gly Met Met Leu Glu Gln Arg
    1145                1150                1155

Ala Cys Ser Arg Ala Thr Val Glu Met Glu Gln Gln Arg Leu Leu
    1160                1165                1170

Arg Glu Ile Asp Ser Phe Phe Phe Gln Glu Ser Ser Leu Arg Glu
    1175                1180                1185

Gln Asn Ser Val Lys
    1190

<210> SEQ ID NO 17
<211> LENGTH: 388
<212> TYPE: PRT
<213> ORGANISM: Plant

<400> SEQUENCE: 17

Met Ala Pro Pro Ala Ser Arg Pro Pro Thr Pro Thr Pro Thr Pro Thr
1               5                   10                  15

Ala Asn Ala Ala Ala Ser Ser Arg Ile Glu Ser Pro Ser Leu Arg
            20                  25                  30

Ala Ala Leu Ala Met Ala Leu Ile His Tyr Asn Arg Leu Pro Ser Arg
        35                  40                  45

Ala Ala Ala Ala Ala Ala Pro Ser Pro Gln Ala Leu Leu Asn Trp Lys
    50                  55                  60

Arg Lys Ala Lys Asp Arg Lys Arg Glu Ile Leu Arg Leu Arg Glu Glu
65                  70                  75                  80

Leu Lys Leu Leu Gln Asp Gly Ala Arg Gly Glu Glu Met Glu Pro Pro
```

```
                    85                  90                  95
Val Ala Ser Cys Arg Cys His Phe Phe Asp Gly Cys Gly Asp Leu Pro
            100                 105                 110

Pro Pro Thr Asp Gly Asp Ala Gly Glu His Trp Val Asp Asp Val Leu
            115                 120                 125

Arg Arg Arg Phe Val Arg Leu Val Arg Trp Lys Asp Lys Arg Arg Arg
130                 135                 140

Leu Asp Arg Ser Leu Pro Thr Ser Ser Leu Met Glu Tyr Asn Thr Glu
145                 150                 155                 160

Asp Glu Val Gln Gln Leu Ser Leu Ser Ile Asp Phe Leu Val Glu Leu
                    165                 170                 175

Ser Asp Gly Leu Phe Ala Lys Arg Glu Ala Gly Ser Ser Phe Thr Thr
                    180                 185                 190

Phe Ser His Gln Ala Val Asp Phe Ile Leu Ala Ser Leu Lys Asn Ile
                195                 200                 205

Leu Ser Glu Arg Glu Lys Glu Ile Ile Glu Glu Ile Ile Asn Gly
210                 215                 220

Leu Val Ala Arg Leu Met Lys Arg Met Cys Thr Thr Pro Glu Asn Ala
225                 230                 235                 240

Gly Ser Val Asp Cys Ser Asp Ala Gln Phe Ser Leu Gln His Leu Phe
                    245                 250                 255

Arg Lys Leu Gly Asn Glu Glu Phe Val Gly Gln Arg Ile Ile Leu Ala
                260                 265                 270

Ile Ser Gln Lys Ile Ser Asn Val Ser Glu Lys Leu Leu Leu Ala Asp
                275                 280                 285

Pro Phe Asp Asp Gly Phe Pro Glu Met His Ser Asn Met Phe Ile Met
290                 295                 300

Ile Gln Leu Ile Glu Phe Leu Ile Ser Asp Ser Phe Asn Asn Trp Leu
305                 310                 315                 320

Cys Arg Asp His Phe Asp Arg Lys Leu Phe Glu Glu Trp Val Arg Ser
                325                 330                 335

Ile Leu Lys Ala Arg Lys Asp Leu Glu Val Leu Asp Gly Arg Asn Gly
                340                 345                 350

Leu Tyr Val Val Tyr Ile Glu Arg Val Ile Gly Arg Leu Ala Arg Glu
                355                 360                 365

Val Ala Pro Ala His Gln Gly Lys Leu Asp Leu Glu Val Leu Ser
            370                 375                 380

Lys Leu Leu Tyr
385

<210> SEQ ID NO 18
<211> LENGTH: 381
<212> TYPE: PRT
<213> ORGANISM: Plant

<400> SEQUENCE: 18

Met Ala Gly Arg Glu Lys Arg Arg Arg Val Ala Ala Leu Asp Gly Glu
1               5                   10                  15

Glu Arg Arg Arg Arg Gln Glu Glu Ala Ala Thr Leu Leu His Arg Ile
            20                  25                  30

Arg Gly Leu Val Arg Trp Val Val Ala Glu Val Ala Ala Gly Arg Ser
        35                  40                  45

Pro Thr Val Ala Leu His Arg Tyr Gln Asn Tyr Cys Ser Ser Ala Ser
    50                  55                  60
```

```
Ala Ala Ala Ala Ser Pro Cys Ala Cys Ser Tyr Asp Val Pro Val Gly
 65                  70                  75                  80

Thr Asp Val Leu Ser Leu Leu His Arg Gly Ser His Ala Ser Arg Leu
                 85                  90                  95

Asn Val Leu Leu Arg Val Leu Val Val Gln Gln Leu Leu Gln Gln
            100                 105                 110

Asn Lys His Cys Ser Lys Arg Asp Ile Tyr Tyr Met Tyr Pro Ser Ile
            115                 120                 125

Phe Gln Glu Gln Ala Val Val Asp Arg Ala Ile Asn Asp Ile Cys Val
130                 135                 140

Leu Phe Lys Cys Ser Arg His Asn Leu Asn Val Val Pro Val Ala Lys
145                 150                 155                 160

Gly Leu Val Met Gly Trp Ile Arg Phe Leu Glu Gly Lys Glu Val
            165                 170                 175

Tyr Cys Val Thr Asn Val Asn Ala Ala Phe Ser Ile Pro Val Ser Ile
            180                 185                 190

Glu Ala Ile Lys Asp Val Val Ser Val Ala Asp Tyr Ile Leu Ile Val
            195                 200                 205

Glu Lys Glu Thr Val Phe Gln Arg Leu Ala Asn Asp Lys Phe Cys Glu
210                 215                 220

Arg Asn Arg Cys Ile Val Ile Thr Gly Arg Gly Tyr Pro Asp Ile Pro
225                 230                 235                 240

Thr Arg Arg Phe Leu Arg Tyr Leu Val Glu Gln Leu His Leu Pro Val
                245                 250                 255

Tyr Cys Leu Val Asp Ala Asp Pro Tyr Gly Phe Asp Ile Leu Ala Thr
            260                 265                 270

Tyr Lys Phe Gly Ser Leu Gln Leu Ala Tyr Asp Ala Asn Phe Leu Arg
            275                 280                 285

Val Pro Asp Ile Arg Trp Leu Gly Val Phe Thr Ser Asp Phe Glu Asp
            290                 295                 300

Tyr Arg Leu Pro Asp Cys Cys Leu Leu His Leu Ser Ser Glu Asp Arg
305                 310                 315                 320

Arg Lys Ala Glu Gly Ile Leu Ser Arg Cys Tyr Leu His Arg Glu Ala
                325                 330                 335

Pro Gln Trp Arg Leu Glu Leu Glu Ala Met Leu Gln Lys Gly Val Lys
            340                 345                 350

Phe Glu Ile Glu Ala Leu Ser Ala Cys Ser Ile Ser Phe Leu Ser Glu
            355                 360                 365

Glu Tyr Ile Pro Lys Lys Ile Lys Gln Gly Arg His Ile
370                 375                 380

<210> SEQ ID NO 19
<211> LENGTH: 385
<212> TYPE: PRT
<213> ORGANISM: Plant

<400> SEQUENCE: 19

Met Ala Glu Ala Gly Val Ala Ala Ala Ser Leu Phe Gly Ala Asp Arg
1               5                   10                  15

Arg Leu Cys Ser Ala Asp Ile Leu Pro Pro Ala Glu Val Arg Ala Arg
            20                  25                  30

Ile Glu Val Ala Val Leu Asn Phe Leu Ala Ala Leu Thr Asp Pro Ala
            35                  40                  45

Ala Pro Ala Ile Ser Ala Leu Pro Leu Ile Ser Arg Gly Ala Ala Asn
50                  55                  60
```

```
Arg Gly Leu Arg Arg Ala Leu Arg Asp Asp Val Ser Val Tyr
 65                  70                  75                  80

Leu Ser Tyr Ala Ser Cys Lys Arg Ser Leu Thr Arg Ala Asn Asp Ala
                 85                  90                  95

Lys Ala Phe Val Arg Val Trp Lys Val Met Glu Met Cys Tyr Lys Ile
            100                 105                 110

Leu Gly Glu Gly Lys Leu Val Thr Leu Arg Glu Leu Phe Tyr Thr Leu
            115                 120                 125

Leu Ser Glu Ser Pro Thr Tyr Phe Thr Cys Gln Arg His Val Asn Gln
            130                 135                 140

Thr Val Gln Asp Val Val Ser Leu Leu Arg Cys Thr Arg Gln Ser Leu
145                 150                 155                 160

Gly Ile Met Ala Ser Ser Arg Gly Ala Leu Ile Gly Arg Leu Val Val
                165                 170                 175

Gln Gly Pro Glu Glu Glu His Val Asp Cys Ser Ile Leu Gly Pro Ser
            180                 185                 190

Gly His Ala Ile Thr Gly Asp Leu Asn Val Leu Ser Lys Leu Ile Phe
            195                 200                 205

Ser Ser Asp Ala Arg Tyr Ile Ile Val Val Glu Lys Asp Ala Ile Phe
210                 215                 220

Gln Arg Leu Ala Glu Asp Arg Ile Tyr Ser His Leu Pro Cys Ile Leu
225                 230                 235                 240

Ile Thr Ala Lys Gly Tyr Pro Asp Leu Ala Thr Arg Phe Ile Leu His
                245                 250                 255

Arg Leu Ser Gln Thr Tyr Pro Asn Met Pro Ile Phe Ala Leu Val Asp
            260                 265                 270

Trp Asn Pro Ala Gly Leu Ala Ile Leu Cys Thr Tyr Lys Tyr Gly Ser
            275                 280                 285

Ile Ser Met Gly Leu Glu Ser Tyr Arg Tyr Ala Cys Asn Val Lys Trp
            290                 295                 300

Leu Gly Leu Arg Gly Asp Asp Leu Gln Leu Ile Pro Gln Ser Ala Tyr
305                 310                 315                 320

Gln Glu Leu Lys Pro Arg Asp Leu Gln Ile Ala Lys Ser Leu Leu Ser
                325                 330                 335

Ser Lys Phe Leu Gln Asp Lys His Arg Ala Glu Leu Thr Leu Met Leu
            340                 345                 350

Glu Thr Gly Lys Arg Ala Glu Ile Glu Ala Leu Tyr Ser His Gly Phe
            355                 360                 365

Asp Phe Leu Gly Lys Tyr Val Ala Arg Lys Ile Val Gln Gly Asp Tyr
            370                 375                 380

Ile
385

<210> SEQ ID NO 20
<211> LENGTH: 469
<212> TYPE: PRT
<213> ORGANISM: Plant

<400> SEQUENCE: 20

Met Pro Pro Thr Met Leu Ala Ser Val Pro Thr Arg Pro Arg Ser His
 1               5                  10                  15

Pro Phe Arg Arg Arg Gly Ala Ala Ala Ala Pro Pro Leu Leu
            20                  25                  30

Pro Asp Gln Ile Ala Ala Ala Ala Ala Ala Ala Lys Arg Pro Ala
```

```
            35                  40                  45
Glu Ser Ser Thr Ser Ala Ser Ser Cys Phe His Ser Glu Val Ile Ser
 50                  55                  60

Ala Thr Ser Thr Thr Cys Pro Thr Ser Leu Ala Ala Gln Arg Pro
 65                  70                  75                  80

Glu Lys Arg Pro Arg Tyr Gln Asp Val Asp Glu Gln Pro Ala
                 85                  90                  95

Ser Glu Cys Ser Glu Ile Ile Gly Gly Ala Arg Pro Arg Ala Ala Glu
                100                 105                 110

Val Glu Val Ser Glu Ser Ser Cys Leu Ala Ser Val Leu Glu Ser Tyr
                115                 120                 125

Leu Ala Cys Pro Glu Gln Leu Ala Asn Asp Ala Glu Thr Thr Ala Tyr
        130                 135                 140

Ser Ser Ala Arg Glu Asp Leu Thr Leu Ser Glu Thr Glu Glu Glu
145                 150                 155                 160

Glu Glu Glu Glu Val Arg Ser Gly Pro Cys Ile Cys Thr Asp Cys Ser
                165                 170                 175

Phe Ser Pro Leu His Glu Ser Ser Ser Ser Asp Asp Asn Ala
        180                 185                 190

Val Pro Ser Pro Thr Phe Ser Leu Phe Leu Ala Leu Ala Glu Gln Phe
        195                 200                 205

Val Pro Phe Thr His Pro Lys Thr Pro Thr Ala Thr Asp Val Ala Leu
210                 215                 220

Gln Ala Gly Glu Gly Lys Arg Phe Glu Asp Leu Asp Asn Glu Val Ser
225                 230                 235                 240

Tyr Glu Arg Phe Arg Arg Glu Arg Arg Gly Val Val Ala Arg Asp
                245                 250                 255

Tyr Ile Glu Val Tyr Ser Ser Met Leu Gly Ser Tyr Gly Arg Ala Val
                260                 265                 270

Val Glu Gln Arg Val Val Met Val Asn Trp Ile Met Glu His Ser Gln
                275                 280                 285

Ala Met Lys Leu Gln Pro Glu Thr Val Phe Met Gly Ile Gly Leu Met
290                 295                 300

Asp Arg Phe Leu Thr Arg Gly Tyr Val Lys Gly Ser Arg Asn Leu Gln
305                 310                 315                 320

Leu Leu Gly Ile Ala Cys Thr Thr Leu Ala Thr Arg Ile Glu Glu Asn
                325                 330                 335

Gln Pro Tyr Asn Cys Ile Leu Gln Lys Ala Phe Lys Val Gly Ile Asn
                340                 345                 350

Thr Tyr Ser Arg Ser Glu Val Val Ala Met Glu Trp Leu Val Gln Glu
        355                 360                 365

Val Leu Asp Phe Gln Cys Phe Val Thr Thr His His Phe Leu Trp
370                 375                 380

Phe Tyr Leu Lys Ala Ala Asn Ala Asp Asp Arg Val Glu Asp Leu Ala
385                 390                 395                 400

Lys Tyr Leu Ala Leu Leu Ser Leu Leu Asp His Lys His Leu Ser Phe
                405                 410                 415

Trp Pro Ser Thr Val Ala Ala Val Val Ala Leu Ala Cys Leu Ala
                420                 425                 430

Thr Asn Asn Glu Ser Ser Cys His Leu Val Met Glu Thr His Met Arg
        435                 440                 445

Thr Lys Asn Asp Asp Leu Pro Glu Cys Leu Met Ser Leu Glu Trp Leu
        450                 455                 460
```

Thr Asn Tyr Ala Ser
465

<210> SEQ ID NO 21
<211> LENGTH: 475
<212> TYPE: PRT
<213> ORGANISM: Plant

<400> SEQUENCE: 21

Met Ser Ala Pro Met Glu Val Ser Phe Ser Ala Pro Pro Pro Asp
1               5                   10                  15

Ala Ala Ser Ala Ala Ala Ala Pro Ser Leu Val Pro Ala Val Ser
                20                  25                  30

Ala Ala Ala Val Ala Ala Thr Thr Val Ser Cys Ser Pro Gln Pro Pro
                35                  40                  45

Thr Gly Ser Pro Ser Ala Asp Asp Arg Ile Leu Val Ser Val Glu Val
        50                  55                  60

Leu Leu His Ala Thr Ser Thr Ala Arg Ala Glu Asp Val Cys Ala Ala
65                  70                  75                  80

Val Glu Arg Met Leu Glu Ala Arg Ser Leu Ser Tyr Val Asp Gly Pro
                85                  90                  95

Val Pro Ile Pro Asn Asp Asp Pro Phe Leu Leu Ala Asn Val Lys Arg
                100                 105                 110

Ile Gln Ile Cys Asp Thr Asp Glu Trp Thr Glu Asn His Lys Val Leu
                115                 120                 125

Leu Phe Trp Gln Val Arg Pro Val Val His Val Phe Gln Leu Ser Glu
                130                 135                 140

Asp Gly Pro Gly Glu Glu Pro Gly Asp Asp Thr Leu Ser Ser Phe
145                 150                 155                 160

Asn Glu Trp Ala Leu Pro Ala Lys Glu Phe Asp Gly Leu Trp Glu Ser
                165                 170                 175

Leu Leu Tyr Glu Val Gly Leu Lys Gln Arg Leu Arg Tyr Ala Ala
                180                 185                 190

Ser Ala Leu Leu Phe Thr Glu Lys Gly Val Asp Pro Cys Leu Val Ser
                195                 200                 205

Trp Asn Arg Ile Val Leu Leu His Gly Pro Pro Gly Thr Gly Lys Thr
                210                 215                 220

Ser Leu Cys Lys Ala Leu Ala Gln Lys Leu Ser Ile Arg Phe Lys Ser
225                 230                 235                 240

Arg Tyr Ser Met Cys Gln Leu Ile Glu Val Asn Ala His Ser Leu Phe
                245                 250                 255

Ser Lys Trp Phe Ser Glu Ser Gly Lys Leu Val Ala Lys Leu Phe Gln
                260                 265                 270

Lys Ile Gln Glu Met Val Glu Glu Ser Asn Leu Val Phe Val Leu
                275                 280                 285

Ile Asp Glu Val Glu Ser Leu Ala Ala Ala Arg Gln Ala Ala Ile Ser
                290                 295                 300

Gly Ser Glu Pro Ser Asp Ser Ile Arg Val Val Asn Ala Leu Leu Thr
305                 310                 315                 320

Gln Met Asp Lys Leu Lys Ser Trp Pro Asn Val Ile Ile Leu Thr Thr
                325                 330                 335

Ser Asn Ile Thr Thr Ala Ile Asp Ile Ala Phe Val Asp Arg Ala Asp
                340                 345                 350

Ile Lys Ala Tyr Val Gly Pro Pro Thr Leu Gln Ala Arg Tyr Glu Ile

```
            355                 360                 365
Leu Arg Ser Cys Leu Gln Glu Leu Leu Arg Val Gly Ile Leu Thr His
    370                 375                 380

Thr Gln Gly Gly Asn Ser Leu Cys Leu Leu Ser Tyr Phe Ser Leu Met
385                 390                 395                 400

Glu Asn Gln His Cys Pro Glu Val Ala Asp Pro His Gly Ser Val His
                405                 410                 415

Leu Ser Gly Leu Leu His Lys Ala Ala Glu Ile Cys Glu Gly Leu Ser
            420                 425                 430

Gly Arg Thr Leu Arg Lys Leu Pro Phe Leu Ala His Ala Ser Val Ala
        435                 440                 445

Asn Pro Ser Cys Cys Asp Ala Ser Ala Phe Leu His Ala Leu Ile Gln
    450                 455                 460

Thr Ala Gln Arg Glu Leu Ser Glu Ser Arg Gly
465                 470                 475

<210> SEQ ID NO 22
<211> LENGTH: 286
<212> TYPE: PRT
<213> ORGANISM: Plant

<400> SEQUENCE: 22

Met Glu Arg Ala Thr Thr Ser Gly Gly Gly Gly Gly Ser Gln Pro
1               5                   10                  15

Pro Arg Gly Val Gly Leu Pro Leu Val Glu Val Gln Ala Ala Ala
                20                  25                  30

Ser Leu Arg Arg Ser Glu Val Phe Tyr Val Val Lys Glu Leu Leu Gly
            35                  40                  45

Phe Val Leu Tyr Met His His Gln Ile Pro Ala Val Leu Gln Asn Leu
    50                  55                  60

Glu Asn Glu Phe Ala Ser Leu Lys Glu Met Thr Glu Met Ala Leu
65                  70                  75                  80

Pro Pro Gly Glu Met Lys Pro Ser Asp Gln Arg Lys Tyr Asn Thr Arg
                85                  90                  95

Lys Arg Glu Val Arg Arg Ile Lys Lys Gln Glu Lys Leu Met Asn
            100                 105                 110

Gly Leu Ser Ser Val Phe Ser Ala Leu Gln Lys Ala Leu Asp Glu Val
        115                 120                 125

Pro Ser Ile Glu Gly Val Leu Leu Ile Leu Gly Gly Ser Leu Val Arg
    130                 135                 140

Pro Leu Phe Val Tyr Asp Ile Thr Ile Ser His Gly Arg Phe Asp Ala
145                 150                 155                 160

Gly Ser Ala Asn Glu Arg Gly Ala Ser Lys Leu Ala Gln Ser Val Ser
                165                 170                 175

Arg Lys Ala Ile Arg Ala Leu Ile Ser Ser Gly Ala Gly Ser Leu Ser
            180                 185                 190

Tyr Thr Gly Pro Thr Lys Leu Phe Val Leu Val Arg Cys Pro Cys Thr
        195                 200                 205

Leu Asn Leu Pro Leu Asp Phe Leu Pro Lys Arg Asp Phe Arg Tyr Ser
    210                 215                 220

Lys Lys Val Val Pro Leu Gln Met Cys Ile Lys Cys Asn Ile Ala Gly
225                 230                 235                 240

Ile Gln Ile Asp Asn Gln Gln Ile Thr Ser Ile Val Asp Ala Ser Arg
                245                 250                 255
```

```
Cys Thr Ser Glu Ser Thr Ile Ser Glu Val Ile Trp Phe Gln Cys Lys
            260                 265                 270

His Thr Ile Arg Gly Leu Pro Cys Lys Ala Ser Leu Glu Glu
            275                 280                 285

<210> SEQ ID NO 23
<211> LENGTH: 487
<212> TYPE: PRT
<213> ORGANISM: Plant

<400> SEQUENCE: 23

Met Ala Ser Ser Pro Pro Ser Thr Ala Ser Pro Thr Ser Ser Ser
1               5                   10                  15

Pro Tyr Arg Lys Leu Leu His Ser Leu Ile Tyr Trp Ala Val Gln Arg
            20                  25                  30

Cys Arg Met Ser Glu Ser Pro Cys Arg Leu Thr Val Ser Val Lys Arg
            35                  40                  45

Ser Pro Glu Pro Ala Gly Ser Ser Pro Leu Arg Ile Ser Val Ser Asp
50                  55                  60

Thr Gly Val Gly Ser Lys Leu Glu Glu Phe Leu Glu Leu Asp Ala Leu
65                  70                  75                  80

Ala Arg Glu Thr Pro Val Glu Lys Trp Asp Gly Thr Leu Leu Ile Thr
                85                  90                  95

Thr Thr Gly Ile Asp Asp Lys Ala Ile Tyr Arg Tyr Gln Phe Asn Leu
            100                 105                 110

Gln Glu Asp Thr Ser Ser Ser Thr Arg Phe Thr Lys Leu Ala Thr Met
            115                 120                 125

Tyr Lys Ser Arg Ala Ile Phe Ser Gly Thr Glu Val Cys Leu Cys Leu
130                 135                 140

Pro Thr Glu Ala Asp Val Asp Asp Leu Ile Leu Trp Leu Val Gly Phe
145                 150                 155                 160

Val Arg Lys Ile Phe Val Leu Arg Ala Ser Asn Leu Ala Cys Glu Leu
                165                 170                 175

Phe Val Ala Gln Thr Asp Ser Ala Gly Ser Gly Asp Val Cys Leu Ser
            180                 185                 190

Gln Ser Asp Asp Val His Ile Ser Ile Thr Thr Ser Ser Ile Asp
            195                 200                 205

Arg Leu Val Ser Gly Leu Lys Asp Tyr Ala Leu Ser His Ala Asn Thr
210                 215                 220

Ser Asp Arg Cys Glu Ala Cys Tyr Met Asn Arg Asp Arg Leu Lys Ile
225                 230                 235                 240

Gly Thr Gly Thr Ala Lys Tyr Val Asp Lys Arg Lys Ala Lys Gly Gln
                245                 250                 255

Leu Val Glu Val Val Ile Met Ile Ala Pro Thr Ser Ser Asp Leu Ser
            260                 265                 270

Cys Trp Met Thr Asn Cys Ser Ser Thr Gln Val Leu His Phe Val Glu
            275                 280                 285

Phe Ile Pro Cys Pro Ile Ser Gln Ser Ser Leu Ser Ala Leu Met Ser
            290                 295                 300

Ile Asp Trp Gln Ser Tyr Gly Phe Lys Phe Lys Gly Gly Phe Ile Asp
305                 310                 315                 320

Asp Asp Gly Asn Ala Glu Leu Gln Trp Asp Asn Met Ala Phe Ser His
                325                 330                 335

Val Asp Ile Ala Ile His Thr Tyr His Glu Gly Ala Val Asp Glu Trp
            340                 345                 350
```

```
Lys Ser Ser Gln Pro Glu Arg His Leu Leu Arg Lys Ala Leu Lys Ser
        355                 360                 365
Ala Leu Phe Gly Leu Lys Ala Asp His Ala Glu Asp Phe Leu Ser Cys
    370                 375                 380
His Gly Gln Lys Val Arg Glu Tyr Val Pro Asp Leu Ala Glu Ser Ile
385                 390                 395                 400
Ala Gly Leu Ile Leu Ser Ser Asn Asp Gln Glu Phe Gln Asp Glu Cys
                405                 410                 415
Ile Ala Leu Leu Gly Leu Gly Ser Asp Gln Asp Leu Thr Glu Gly Ala
            420                 425                 430
Val Arg Ser Cys Ile Gly Glu Lys Met Asn Arg Ile Ile Glu Met Asn
        435                 440                 445
Asp Thr Lys Glu Asn Val Glu His Asn Ala Pro Tyr Leu Phe Glu Cys
    450                 455                 460
Glu Arg Phe Asp Glu Asp Tyr Ser Leu Leu Asp Glu Asp Pro Asp
465                 470                 475                 480
Glu Asp Met Ile Phe Asp Phe
                485

<210> SEQ ID NO 24
<211> LENGTH: 233
<212> TYPE: PRT
<213> ORGANISM: Plant

<400> SEQUENCE: 24

Met Arg His Asn Ile Lys Phe Lys Ser Lys Gly Thr Leu Lys Ile Arg
1               5                   10                  15
Asn Thr Ala Gln Ile Ser Leu Trp Lys Lys Cys Ser Asp Ser Met Ile
            20                  25                  30
Ala Asp Gln Thr Tyr Leu Phe Ile Asn Arg Val Gln Asp Arg Arg Phe
        35                  40                  45
Asp Glu Glu Ser Leu Arg Ile Leu Glu Leu Ser Leu Val Ala Met Asn
    50                  55                  60
Val Lys Ser Phe Leu Glu Val Arg Ser Arg Leu Arg Asp Phe Met Arg
65                  70                  75                  80
Ser Glu Ser Val Val Ile Phe Gly Glu Leu Thr Gly Glu Ser Met Val
                85                  90                  95
Ala Lys Leu Ser Val Leu Glu Phe Phe Ala Arg Ala Phe Ala Leu Leu
            100                 105                 110
Gly Asp Met Glu Ser Cys Leu Ala Met Arg Tyr Glu Ala Leu Asn Leu
        115                 120                 125
Arg Gln Leu Lys Ser Pro Ser Cys Leu Trp Leu Gly Val Ser His Ser
    130                 135                 140
Glu Trp Thr Lys Phe Ala Val Gln Ser Met Glu Asn Gly Phe Pro Ser
145                 150                 155                 160
Ile Ala Gly Lys Ala Ser Glu Asn Ala Leu Leu Ser Leu Lys Lys Asp
                165                 170                 175
Ser Leu Ile Glu Pro Lys Ser Glu Asp Asn Ser Asp Ile Leu Asp Ala
            180                 185                 190
Ala Glu Lys Val Arg Arg Leu Arg Asp Ser Ala Ala Ser Leu Thr Ser
        195                 200                 205
Ser His Ser Gly Ile Phe Ile Tyr Ile Val Ser Ser Leu Lys Phe Ala
    210                 215                 220
Val Cys Asn Arg Leu Leu Thr Thr Phe
```

```
                     225                 230

<210> SEQ ID NO 25
<211> LENGTH: 608
<212> TYPE: PRT
<213> ORGANISM: Plant

<400> SEQUENCE: 25

Met Phe Tyr Ser His Gln Leu Leu Ala Arg Lys Ala Pro Leu Gly Gln
1               5                   10                  15

Ile Trp Met Ala Ala Thr Leu His Ser Lys Ile Asn Arg Lys Arg Leu
            20                  25                  30

Asp Lys Leu Asp Ile Ile Lys Ile Cys Glu Glu Ile Leu Asn Pro Ser
        35                  40                  45

Val Pro Met Ala Leu Arg Leu Ser Gly Ile Leu Met Gly Gly Val Ala
    50                  55                  60

Ile Val Tyr Glu Arg Lys Val Lys Ala Leu Tyr Asp Asp Val Ser Arg
65                  70                  75                  80

Phe Leu Ile Glu Ile Asn Glu Ala Trp Arg Val Lys Pro Val Ala Asp
                85                  90                  95

Pro Thr Val Leu Pro Lys Gly Lys Thr Gln Ala Lys Tyr Glu Ala Val
            100                 105                 110

Thr Leu Pro Glu Asn Ile Met Asp Met Asp Val Glu Gln Pro Met Leu
        115                 120                 125

Phe Ser Glu Ala Asp Thr Thr Arg Phe Arg Gly Met Arg Leu Glu Asp
    130                 135                 140

Leu Asp Asp Gln Tyr Ile Asn Val Asn Leu Asp Asp Asp Phe Ser
145                 150                 155                 160

Arg Ala Glu Asn His His Gln Ala Asp Ala Glu Asn Ile Thr Leu Ala
                165                 170                 175

Asp Asn Phe Gly Ser Gly Leu Gly Glu Thr Asp Val Phe Asn Arg Phe
            180                 185                 190

Glu Arg Phe Asp Ile Thr Asp Asp Ala Thr Phe Asn Val Thr Pro
        195                 200                 205

Asp Gly His Pro Gln Val Pro Ser Asn Leu Val Pro Ser Pro Arg
    210                 215                 220

Gln Glu Asp Ser Pro Gln Gln Glu Asn His His Ala Ala Ser Ser
225                 230                 235                 240

Pro Leu His Glu Glu Ala Gln Gln Gly Gly Ala Ser Val Lys Asn Glu
                245                 250                 255

Gln Glu Gln Gln Lys Met Lys Gly Gln Pro Ala Lys Ser Ser Lys
            260                 265                 270

Arg Lys Lys Arg Arg Lys Asp Asp Glu Val Met Met Asp Asn Asp Gln
        275                 280                 285

Ile Met Ile Pro Gly Asn Val Tyr Gln Thr Trp Leu Lys Asp Pro Ser
    290                 295                 300

Ser Leu Ile Thr Lys Arg His Arg Ile Asn Ser Lys Val Asn Leu Ile
305                 310                 315                 320

Arg Ser Ile Lys Ile Arg Asp Leu Met Asp Leu Pro Leu Val Ser Leu
                325                 330                 335

Ile Ser Ser Leu Glu Lys Ser Pro Leu Glu Phe Tyr Tyr Pro Lys Glu
            340                 345                 350

Leu Met Gln Leu Trp Lys Glu Cys Thr Glu Val Lys Ser Pro Lys Ala
        355                 360                 365
```

-continued

Pro Ser Ser Gly Gly Gln Gln Ser Ser Pro Glu Gln Gln Gln Arg
    370                 375                 380

Asn Leu Pro Pro Gln Ala Phe Pro Thr Gln Pro Gln Val Asp Asn Asp
385                 390                 395                 400

Arg Glu Met Gly Phe His Pro Val Asp Phe Ala Asp Asp Ile Glu Lys
                405                 410                 415

Leu Arg Gly Asn Thr Ser Gly Glu Tyr Gly Arg Asp Tyr Asp Ala Phe
            420                 425                 430

His Ser Asp His Ser Val Thr Pro Gly Ser Pro Gly Leu Ser Arg Arg
        435                 440                 445

Ser Ala Ser Ser Ser Gly Gly Ser Gly Arg Gly Phe Thr Gln Leu Asp
450                 455                 460

Pro Glu Val Gln Leu Pro Ser Gly Arg Ser Lys Arg Gln His Ser Ser
465                 470                 475                 480

Gly Lys Ser Phe Gly Asn Leu Asp Pro Val Glu Glu Phe Pro Phe
                485                 490                 495

Glu Gln Glu Leu Arg Asp Phe Lys Met Arg Arg Leu Ser Asp Val Gly
                500                 505                 510

Pro Thr Pro Asp Leu Leu Glu Glu Ile Glu Pro Thr Gln Thr Pro Tyr
            515                 520                 525

Glu Lys Lys Ser Asn Pro Ile Asp Gln Val Thr Gln Ser Ile His Ser
530                 535                 540

Tyr Leu Lys Leu His Phe Asp Thr Pro Gly Ala Ser Gln Ser Glu Ser
545                 550                 555                 560

Leu Ser Gln Leu Ala His Gly Met Thr Thr Ala Lys Ala Ala Arg Leu
                565                 570                 575

Phe Tyr Gln Ala Cys Val Leu Ala Thr His Asp Phe Ile Lys Val Asn
                580                 585                 590

Gln Leu Glu Pro Tyr Gly Asp Ile Leu Ile Ser Arg Gly Pro Lys Met
            595                 600                 605

<210> SEQ ID NO 26
<211> LENGTH: 234
<212> TYPE: PRT
<213> ORGANISM: Plant

<400> SEQUENCE: 26

Met Pro Glu Val Arg Asn Ser Gly Gly Arg Ala Ala Leu Ala Asp Pro
1               5                   10                  15

Ser Gly Gly Gly Phe Phe Ile Arg Arg Thr Thr Ser Pro Pro Gly Ala
                20                  25                  30

Val Ala Val Lys Pro Leu Ala Arg Arg Ala Leu Pro Pro Thr Ser Asn
            35                  40                  45

Lys Glu Asn Val Pro Pro Ser Trp Ala Val Thr Val Arg Ala Thr Pro
        50                  55                  60

Lys Arg Arg Ser Pro Leu Pro Glu Trp Tyr Pro Arg Ser Pro Leu Arg
65                  70                  75                  80

Asp Ile Thr Ser Val Val Lys Ala Val Glu Arg Lys Ser Arg Leu Gly
                85                  90                  95

Asn Ala Ala Val Arg Gln Gln Ile Gln Leu Ser Glu Asp Ser Ser Arg
            100                 105                 110

Ser Val Asp Pro Ala Thr Pro Val Gln Lys Glu Glu Gly Val Pro Gln
        115                 120                 125

Ser Thr Pro Thr Pro Pro Thr Gln Lys Ala Leu Asp Ala Ala Ala Pro
    130                 135                 140

```
Cys Pro Gly Ser Thr Gln Ala Val Ala Ser Thr Ser Thr Ala Tyr Leu
145                 150                 155                 160

Ala Glu Gly Lys Pro Lys Ala Ser Ser Ser Pro Ser Asp Cys Ser
            165                 170                 175

Phe Gln Thr Pro Ser Arg Pro Asn Asp Pro Ala Leu Ala Asp Leu Met
            180                 185                 190

Glu Lys Glu Leu Ser Ser Ile Glu Gln Ile Glu Lys Met Val Arg
            195                 200                 205

Lys Asn Leu Lys Arg Ala Pro Lys Ala Ala Gln Pro Ser Lys Val Thr
            210                 215                 220

Ile Gln Lys Arg Thr Leu Leu Ser Met Arg
225                 230

<210> SEQ ID NO 27
<211> LENGTH: 442
<212> TYPE: PRT
<213> ORGANISM: Plant

<400> SEQUENCE: 27

Met Ser Ser Ser Arg Asn Leu Ser Gln Glu Asn Pro Ile Pro Arg
1               5                   10                  15

Pro Asn Leu Ala Lys Thr Arg Thr Ser Leu Arg Asp Val Gly Asn Arg
            20                  25                  30

Arg Ala Pro Leu Gly Asp Ile Thr Asn Gln Lys Asn Gly Ser Arg Asn
            35                  40                  45

Pro Ser Pro Ser Ser Thr Leu Val Asn Cys Ser Asn Lys Ile Gly Gln
50                  55                  60

Ser Lys Lys Ala Pro Lys Pro Ala Leu Ser Arg Asn Trp Asn Leu Gly
65                  70                  75                  80

Ile Leu Asp Ser Gly Leu Pro Pro Lys Pro Asn Ala Lys Ser Asn Ile
                85                  90                  95

Ile Val Pro Tyr Glu Asp Thr Glu Leu Leu Gln Ser Asp Asp Ser Leu
            100                 105                 110

Leu Cys Ser Ser Pro Ala Leu Ser Leu Asp Ala Ser Pro Thr Gln Ser
            115                 120                 125

Asp Pro Ser Ile Ser Thr His Asp Ser Leu Thr Asn His Val Val Asp
            130                 135                 140

Tyr Met Val Glu Ser Thr Thr Asp Asp Gly Asn Asp Asp Asp Asp Asp
145                 150                 155                 160

Glu Ile Val Asn Ile Asp Ser Asp Leu Met Asp Pro Gln Leu Cys Ala
                165                 170                 175

Ser Phe Ala Cys Asp Ile Tyr Glu His Leu Arg Val Ser Glu Val Asn
            180                 185                 190

Lys Arg Pro Ala Leu Asp Tyr Met Glu Arg Thr Gln Ser Ser Ile Asn
            195                 200                 205

Ala Ser Met Arg Ser Ile Leu Ile Asp Trp Leu Val Glu Val Ala Glu
            210                 215                 220

Glu Tyr Arg Leu Ser Pro Glu Thr Leu Tyr Leu Ala Val Asn Tyr Val
225                 230                 235                 240

Asp Arg Tyr Leu Thr Gly Asn Ala Ile Asn Lys Gln Asn Leu Gln Leu
                245                 250                 255

Leu Gly Val Thr Cys Met Met Ile Ala Ala Lys Tyr Glu Glu Val Cys
            260                 265                 270

Val Pro Gln Val Glu Asp Phe Cys Tyr Ile Thr Asp Asn Thr Tyr Leu
```

```
                  275                 280                 285
Arg Asn Glu Leu Leu Glu Met Glu Ser Ser Val Leu Asn Tyr Leu Lys
    290                 295                 300

Phe Glu Leu Thr Thr Pro Thr Ala Lys Cys Phe Leu Arg Arg Phe Leu
305                 310                 315                 320

Arg Ala Ala Gln Gly Arg Lys Glu Val Pro Ser Leu Leu Ser Glu Cys
                325                 330                 335

Leu Ala Cys Tyr Leu Thr Glu Leu Ser Leu Leu Asp Tyr Ala Met Leu
            340                 345                 350

Arg Tyr Ala Pro Ser Leu Val Ala Ala Ser Ala Val Phe Leu Ala Gln
        355                 360                 365

Tyr Thr Leu His Pro Ser Arg Lys Pro Trp Asn Ala Thr Leu Glu His
    370                 375                 380

Tyr Thr Ser Tyr Arg Ala Lys His Met Glu Ala Cys Val Lys Asn Leu
385                 390                 395                 400

Leu Gln Leu Cys Asn Glu Lys Leu Ser Ser Asp Val Val Ala Ile Arg
                405                 410                 415

Lys Lys Tyr Ser Gln His Lys Tyr Lys Phe Ala Ala Lys Lys Leu Cys
            420                 425                 430

Pro Thr Ser Leu Pro Gln Glu Leu Phe Leu
        435                 440

<210> SEQ ID NO 28
<211> LENGTH: 450
<212> TYPE: PRT
<213> ORGANISM: Plant

<400> SEQUENCE: 28

Met Cys Pro Cys Val Glu Arg Arg Ala Pro Pro Gly Val Tyr Tyr Thr
1               5                   10                  15

Pro Pro Pro Ala Arg Thr Ser Asp His Val Ala Ala Met Pro Met Thr
                20                  25                  30

Glu Arg Arg Arg Pro Pro Tyr Ser Cys Ser Ser Ser Ser Glu Arg Arg
            35                  40                  45

Asp Pro Phe His Ile Val His Lys Val Pro Ser Gly Asp Ser Pro Tyr
    50                  55                  60

Val Arg Ala Lys His Ala Gln Leu Ile Asp Lys Asp Pro Asn Arg Ala
65                  70                  75                  80

Ile Ser Leu Phe Trp Thr Ala Ile Asn Ala Gly Asp Arg Val Asp Ser
                85                  90                  95

Ala Leu Lys Asp Met Ala Val Val Met Lys Gln Leu Gly Arg Ser Asp
                100                 105                 110

Glu Gly Ile Glu Ala Ile Lys Ser Phe Arg Tyr Leu Cys Ser Phe Glu
            115                 120                 125

Ser Gln Asp Ser Ile Asp Asn Leu Leu Leu Glu Leu Tyr Lys Lys Ser
    130                 135                 140

Gly Arg Ile Glu Glu Glu Ala Val Leu Leu Glu His Lys Leu Gln Thr
145                 150                 155                 160

Leu Glu Gln Gly Met Gly Phe Gly Gly Arg Val Ser Arg Ala Lys Arg
                165                 170                 175

Val Gln Gly Lys His Val Ile Met Thr Ile Glu Gln Glu Lys Ala Arg
                180                 185                 190

Ile Leu Gly Asn Leu Gly Trp Val His Leu Gln Leu His Asn Tyr Gly
            195                 200                 205
```

-continued

```
Ile Ala Glu Gln His Tyr Arg Phe Gly Phe Val Thr Lys Ile Pro Asn
210                 215                 220

Ile Asp Tyr Cys Leu Val Met Arg Ala Leu Gly Leu Glu Arg Asp Lys
225                 230                 235                 240

Asn Lys Leu Cys Asn Leu Ala Ile Cys Leu Met Arg Met Ser Arg Ile
            245                 250                 255

Pro Glu Ala Lys Ser Leu Leu Asp Asp Val Arg Asp Ser Pro Ala Glu
        260                 265                 270

Ser Glu Cys Gly Asp Glu Pro Phe Ala Lys Ser Tyr Asp Arg Ala Val
            275                 280                 285

Glu Met Leu Ala Glu Ile Glu Ser Lys Pro Glu Ala Asp Leu Ser
290                 295                 300

Glu Lys Phe Tyr Ala Gly Cys Ser Phe Val Asn Arg Met Lys Glu Asn
305                 310                 315                 320

Ile Ala Pro Gly Thr Ala Asn Lys Asn Tyr Ser Asp Val Ser Ser Ser
            325                 330                 335

Pro Ala Ser Val Arg Pro Asn Ser Ala Gly Leu Tyr Thr Gln Pro Arg
        340                 345                 350

Arg Cys Arg Leu Phe Glu Glu Thr Arg Gly Ala Ala Arg Lys Leu
    355                 360                 365

Leu Phe Gly Lys Pro Gln Pro Phe Gly Ser Glu Gln Met Lys Ile Leu
370                 375                 380

Glu Arg Gly Glu Glu Pro Met Lys Arg Lys Leu Asp Gln Asn
385                 390                 395                 400

Met Ile Gln Tyr Leu His Glu Phe Val Lys Asp Thr Ala Asp Gly Pro
            405                 410                 415

Lys Ser Glu Ser Lys Lys Ser Trp Ala Asp Ile Ala Glu Glu Glu
        420                 425                 430

Ala Glu Glu Glu Glu Glu Arg Leu Gln Gly Glu Leu Lys Thr Ala
            435                 440                 445

Glu Met
    450

<210> SEQ ID NO 29
<211> LENGTH: 432
<212> TYPE: PRT
<213> ORGANISM: Plant

<400> SEQUENCE: 29

Met Ala Ala Ser Tyr Ser Cys Arg Arg Thr Cys Glu Ala Cys Ser Thr
1               5                   10                  15

Arg Ala Met Ala Gly Cys Val Val Gly Glu Pro Ala Ser Ala Pro Gly
            20                  25                  30

Gln Arg Val Thr Leu Leu Ala Ile Asp Gly Gly Ile Arg Gly Leu
        35                  40                  45

Ile Pro Gly Thr Ile Leu Ala Phe Leu Glu Ala Arg Leu Gln Glu Leu
    50                  55                  60

Asp Gly Pro Asp Ala Arg Leu Ala Asp Tyr Phe Asp Cys Ile Ala Gly
65                  70                  75                  80

Thr Ser Thr Gly Gly Leu Ile Thr Ala Met Leu Ala Ala Pro Gly Asp
                85                  90                  95

His Gly Arg Pro Leu Phe Ala Ala Ser Asp Ile Asn Arg Phe Tyr Leu
            100                 105                 110

Asp Asn Gly Pro Leu Ile Phe Pro Gln Lys Arg Cys Gly Met Ala Ala
        115                 120                 125
```

```
Ala Met Ala Ala Leu Thr Arg Pro Arg Tyr Asn Gly Lys Tyr Leu Gln
    130                 135                 140

Gly Lys Ile Arg Lys Met Leu Gly Glu Thr Arg Val Arg Asp Thr Leu
145                 150                 155                 160

Thr Asn Val Val Ile Pro Thr Phe Asp Val Arg Leu Leu Gln Pro Thr
                165                 170                 175

Ile Phe Ser Thr Tyr Asp Ala Lys Ser Met Pro Leu Lys Asn Ala Leu
            180                 185                 190

Leu Ser Asp Ile Cys Ile Ser Thr Ser Ala Ala Pro Thr Tyr Leu Pro
        195                 200                 205

Ala His Cys Phe Gln Thr Thr Asp Ala Thr Gly Lys Val Arg Glu
    210                 215                 220

Phe Asp Leu Ile Asp Gly Gly Val Ala Ala Asn Asn Pro Thr Met Val
225                 230                 235                 240

Ala Met Thr Gln Ile Thr Lys Lys Ile Met Val Lys Asp Lys Glu Glu
                245                 250                 255

Leu Tyr Pro Val Lys Pro Ser Asp Cys Gly Lys Phe Leu Val Leu Ser
            260                 265                 270

Val Gly Thr Gly Ser Thr Ser Asp Gln Gly Met Tyr Thr Ala Arg Gln
        275                 280                 285

Cys Ser Arg Trp Gly Ile Val Arg Trp Leu Arg Asn Lys Gly Met Ala
    290                 295                 300

Pro Ile Ile Asp Ile Phe Met Ala Ala Ser Ser Asp Leu Val Asp Ile
305                 310                 315                 320

His Ala Ala Val Met Phe Gln Ser Leu His Ser Asp Gly Asp Tyr Leu
                325                 330                 335

Arg Ile Gln Asp Asn Thr Leu His Gly Asp Ala Ala Thr Val Asp Ala
            340                 345                 350

Ala Thr Arg Asp Asn Met Arg Ala Leu Val Gly Ile Gly Glu Arg Met
        355                 360                 365

Leu Ala Gln Arg Val Ser Arg Val Asn Val Glu Thr Gly Arg Tyr Val
    370                 375                 380

Glu Val Pro Gly Ala Gly Ser Asn Ala Asp Ala Leu Arg Gly Phe Ala
385                 390                 395                 400

Arg Gln Leu Ser Glu Glu Arg Arg Ala Arg Leu Gly Arg Arg Asn Ala
                405                 410                 415

Cys Gly Gly Gly Glu Gly Glu Pro Ser Gly Val Ala Cys Lys Arg
            420                 425                 430

<210> SEQ ID NO 30
<211> LENGTH: 23
<212> TYPE: DNA
<213> ORGANISM: Artificial Sequence
<220> FEATURE:
<223> OTHER INFORMATION: ZmOSD1 gene knockout site
<220> FEATURE:
<221> NAME/KEY: primer_bind
<222> LOCATION: (21)..(23)
<223> OTHER INFORMATION: PAM Sequence

<400> SEQUENCE: 30
tctgcctgta ctggagttat tgg                                    23

<210> SEQ ID NO 31
<211> LENGTH: 23
<212> TYPE: DNA
<213> ORGANISM: Artificial Sequence
```

```
<220> FEATURE:
<223> OTHER INFORMATION: ZmPAIR1 gene knockout site
<220> FEATURE:
<221> NAME/KEY: primer_bind
<222> LOCATION: (21)..(23)
<223> OTHER INFORMATION: PAM Sequence

<400> SEQUENCE: 31
ggaaggcgag gatggttccc ggg                                                 23

<210> SEQ ID NO 32
<211> LENGTH: 23
<212> TYPE: DNA
<213> ORGANISM: Artificial Sequence
<220> FEATURE:
<223> OTHER INFORMATION: ZmREC8 gene knockout site
<220> FEATURE:
<221> NAME/KEY: primer_bind
<222> LOCATION: (21)..(23)
<223> OTHER INFORMATION: PAM Sequence

<400> SEQUENCE: 32
ggaagtccca cgagtaatta tgg                                                 23

<210> SEQ ID NO 33
<211> LENGTH: 23
<212> TYPE: DNA
<213> ORGANISM: Artificial Sequence
<220> FEATURE:
<223> OTHER INFORMATION: ZmREC8 gene knockout site
<220> FEATURE:
<221> NAME/KEY: primer_bind
<222> LOCATION: (21)..(23)
<223> OTHER INFORMATION: PAM Sequence

<400> SEQUENCE: 33
ggaaggcgag gatggttccc ggg                                                 23

<210> SEQ ID NO 34
<211> LENGTH: 22
<212> TYPE: DNA
<213> ORGANISM: Artificial Sequence
<220> FEATURE:
<223> OTHER INFORMATION: SlOSD1 gene knockout site
<220> FEATURE:
<221> NAME/KEY: primer_bind
<222> LOCATION: (20)..(22)
<223> OTHER INFORMATION: PAM Sequence

<400> SEQUENCE: 34
cagaagcagg gagaatggca gg                                                  22

<210> SEQ ID NO 35
<211> LENGTH: 22
<212> TYPE: DNA
<213> ORGANISM: Artificial Sequence
<220> FEATURE:
<223> OTHER INFORMATION: SlSPO11 gene knockout site
<220> FEATURE:
<221> NAME/KEY: primer_bind
<222> LOCATION: (20)..(22)
<223> OTHER INFORMATION: PAM Sequence

<400> SEQUENCE: 35
cagaagcagg gagaatggca gg                                                  22

<210> SEQ ID NO 36
<211> LENGTH: 22
<212> TYPE: DNA
```

```
<213> ORGANISM: Artificial Sequence
<220> FEATURE:
<223> OTHER INFORMATION: S1REC8 gene knockout site
<220> FEATURE:
<221> NAME/KEY: primer_bind
<222> LOCATION: (20)..(22)
<223> OTHER INFORMATION: PAM Sequence

<400> SEQUENCE: 36
gcacaggagg aacctgctaa gg                                            22

<210> SEQ ID NO 37
<211> LENGTH: 22
<212> TYPE: DNA
<213> ORGANISM: Artificial Sequence
<220> FEATURE:
<223> OTHER INFORMATION: S1MTL gene knockout site
<220> FEATURE:
<221> NAME/KEY: primer_bind
<222> LOCATION: (21)..(22)
<223> OTHER INFORMATION: PAM Sequence

<400> SEQUENCE: 37
tgattgccgg aacgagcacc gg                                            22
```

METHOD FOR USING PLANT HETEROSIS

CROSS-REFERENCE TO RELATED PATENT APPLICATIONS

The present application is a National Stage of International Patent Application No. PCT/CN2019/077154, filed Mar. 6, 2019, and claims the priority of Chinese Patents Application No. 201810325528.4, filed on Apr. 12, 2018, and 201811205889.1, filed on Oct. 16, 2018, the disclosures of which are incorporated herein by reference in their entirety.

TECHNICAL FELD

The present disclosure relates to the field of biotechnology, specifically, to a method for using plant heterosis.

BACKGROUND

Heterosis refers to the phenomenon that in the biological world, two varieties or related species with different genetic background are hybridized to generate a hybrid, and the generation of the hybrid is better in traits such as growth vigour, viability, adaptability and yield, etc., than their parents. Heterosis is a common phenomenon in the biological world, and it is widely used in the cultivation of varieties and production practice of crops.

For the application of heterosis in agricultural production, one of the most important links is the efficient preparation of hybrid seeds. In diclinous crops such as maize, etc., the male flowers of the maternal inbred line can be manually (or mechanically) removed, and the pollen of another inbred line (male parent) can be used for pollination to obtain hybrid seeds. The operation is relatively simple, therefore, the heterosis of maize has been used early, and the system is mature and widely used. However, there is also the problem that the flowering period of some parents is inconsistent, which makes it impossible to carry out large-scale hybrid seed production in the field.

Moreover, monoecious crops (such as, rice, wheat, etc.) cannot achieve large-scale hybrid seed production by removing pollen from the female parent. For example, rice: at present, the way to solve such problem in rice is to use plants with pollen sterility characteristics as the female parent, and use another variety as the male parent to provide pollen hybrids, that is, a heterosis utilization system using male sterility as the core technology. Among them, the utilization of rice heterosis can be divided into two technical approaches. One is the "three-line method" hybridization technology with nuclear-cytoplasmic interaction pollen sterility as the core technology, and the other is the "two-line method" hybridization technology with photo-thermo sensitive genic male sterile controlled by natural light cycle and temperature as the core technology.

As shown in FIG. 1A, the "three-line method" hybridization technology: uses the nucleocytoplasmic male sterile line as the female parent, and use the maintainer line as the male parent for batch propagation of seeds that still retain the sterile characteristics; use the sterile line as the female parent and the restorer line as the male parent for large scale production of hybrid seeds restoring the pollen fertility and having heterosis, and the hybrid seeds are used to produce hybrid rice.

As shown in FIG. 1B, the "two-line method" hybridization technology: the same rice line, under certain conditions, the pollen of which is fertile, and its fertility is used to propagate the sterile line seeds; under another specific condition, the pollen is sterile, its sterility is used to hybridize with the male parent to prepare hybrid seeds.

Since hybrid rice uses the advantage of the first generation of hybrids, the separation of traits or fertility will occur over many generations, thus seed production must be carried out every year, which consumes a lot of manpower, material resources and land resources. In addition, the "three-line method" is restricted by the restoring and maintaining relationship, and the utilization rate of germplasm resources is low; the "two-line method" is affected by natural temperature and light, and the reproductive yield of sterile lines is unstable, and self-fertility of sterile lines induced at low temperature during hybrid seed production leads to the risk that the purity of hybrid seeds will not reach the standard.

In addition, it is reported by some related literatures that the utilization of heterosis and genes related to plant reproduction, for example: Turning rice meiosis into mitosis, (Cell Research (2016) 26:1242-1254) discloses that the apomictic seeds can be used to make the self-reproduction of F1 hybrids to maintain excellent traits, where the CENH3 genes expressed by exogenous modification are introduced through hybridization. US 2014/0298507 A1 discloses the transformation of apomixis gametes into cloned embryos or seeds. Journal of Sichuan University (Natural Science Edition), Vol. 29, No. 2, 1992, discloses the application of apomixis in plant breeding and research methods of cell embryology.

SUMMARY

The present disclosure aims to provide a method for using plant heterosis so that hybrids can produce cloned seeds or plants, thereby improving seed production efficiency.

In order to achieve the above object, according to one aspect of the present disclosure, a method for using plant heterosis is provided. The method comprises the following steps: S1, transforming the meiosis of germ cells of hybrids into mitosis-like so as to obtain gametes whose genotype and chromosome ploidy are consistent with hybrids by using gene mutation or gene engineering technology; and S2, influencing and involving in the development of gametes or embryos in plants by using gene mutation and gene engineering technology, wherein a protein involved is MTL protein.

Further, the gene mutation includes random mutagenesis and directed mutagenesis; wherein the random mutagenesis includes chemical mutagenesis, physical mutagenesis, and biological mutagenesis; the directed mutagenesis includes gene editing technology, the gene editing technology includes CRISPR/Cas gene editing technology, CRISPR/Cpf1 gene editing technology, TALEN gene editing technology, homing endonuclease gene editing technology and ZFN gene editing technology; the gene engineering technology includes transgene technology to induce specific expression, ectopic expression or gene silencing of genes.

Further, the S1 includes taking hybrid seeds, transforming the meiosis of germ cells of hybrids into mitosis-like to obtain gametes whose genotype and chromosome ploidy are consistent with hybrids by using gene mutation or gene engineering technology.

Further, the S1 includes editing the parent of the hybrid seeds using gene mutation or gene engineering technology, and then obtaining the hybrid through interparental hybridization, so as to obtain hybrid gametes whose meiosis of germ cells is transformed into mitosis-like.

Further, the S1 includes editing proteins involved in meiosis in plants to realize the transformation of meiosis of germ cells into mitosis-like by using gene mutation or gene engineering technology; wherein the proteins include a first protein, a second protein and a third protein, among them, the first protein is a protein involved in the formation of DNA double-strand breaks, and the first protein is a protein selected from the group consisting of:

a PAIR1 protein as shown in SEQ ID NO: 13, a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO: 14, a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO: 15, a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO: 16, a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO: 17, a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO: 18, a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO: 19, a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO: 20, a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO: 21, a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a P31$^{comet}$ protein as shown in SEQ ID NO: 22, a protein having at least 30%, 35%, 40%, 45%, 50%, 55%, 60%, 65%, 70%, 75%, 80%, 85%, 90%, 95% or 98% sequence identity with the P31$^{comet}$ protein, or a protein having at least 40%, 45%, 50%, 55%, 60%, 65%, 70%, 75%, 80%, 85%, 90%, 95% or 98% sequence similarity with the P31$^{comet}$ protein;

a MTOPVIB protein as shown in SEQ ID NO: 23, a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO: 24, a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

the REC8 protein as shown in SEQ ID NO: 25, a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

a OSD1 protein as shown in SEQ ID NO: 26, a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO: 27, a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein;

a TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein.

Further, the S2 includes influencing and involving in the development of gametes or embryos in plants, and inducing the gametes to develop into seeds or plants by using gene mutation and gene engineering technology.

Further, the S2 includes pollinating induced pollen from other plants to induce the gametes to develop into seeds or plants.

Further, the S2 includes inducing the gametes to develop into seeds or plants through physical stimulation, biotic stress, or chemical agent treatment.

Further, the S2 includes inducing the gametes to develop into seeds or plants through anther culture or pollen culture.

Further, the MTL protein is a MTL protein as shown in SEQ ID NO: 29, a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein.

Further, plants include monocotyledonous plants and dicotyledonous plants.

Further, plant include rice, maize, sorghum, millet, barley, wheat, rye, oats, buckwheat, coix seed, sugar cane, asparagus, bamboo shoots, *Allium tuberosum*, yams, soybeans, potatoes, peas, mung beans, adzuki beans, *Vicia faba, Vigna sesquipedalis, Phaseolus vulgaris, Lens culinaris, Calopogonium mucunoides*, chickpeas, cassava, sweet potato, rape, cotton, beets, eggplant, peanuts, tea, mint, coffee, sesame, sunflower, *Ricinus communis*, perillaseed, safflower, tomato, pepper, cucumber, *Brassica chinensis*, lettuce, spinach, garlic, *Brassica oleracea, Brassica juncea, Zizania aquatica*, welsh onion, *Benincasa hispida*, zucchini, loofah, chinese cabbage, radish, onion, watermelon, grape, carrot, cauliflower, pumpkin, tobacco, pasture, *Pennisetum purpureum* schumach, *Pennisetum alopecuroides, Sorghum sudanense*, orchids, lilies, tulips and alfalfa.

According to another aspect of the present disclosure, a plant or seed that maintains heterosis is provided. The plant or seed is prepared by any of the above methods.

According to still another aspect of the present disclosure, a kit for maintaining heterosis in plants is provided. The kit includes a vector and/or reagent capable of transforming meiosis of plants germ cells into mitosis-like, and a vector and/or reagent for the development of gametes into seeds or plants.

Further, the vector and/or reagent capable of transforming meiosis of germ cells in plants into mitosis-like is a vector and/or reagent used in gene mutation or gene engineering technology to transform the meiosis of germ cells of hybrids into mitosis-like, preferably the vector and/or reagent is a vector and/or reagent for random mutagenesis or directed mutagenesis.

Further, the random mutagenesis includes chemical mutagenesis, physical mutagenesis, and biological mutagenesis; the directed mutagenesis includes CRISPR/Cas gene editing technology, CRISPR/Cpf1 gene editing technology, TALEN gene editing technology, homing endonuclease gene editing technology and ZFN gene editing technology; the gene engineering technology includes transgene technology to induce specific expression, ectopic expression or gene silencing of genes.

Further, the vector and/or reagent capable of transforming meiosis of germ cells in plants into mitosis-like is a vector and/or reagent used in gene mutation or gene engineering technology to edit proteins involved in meiosis in plants to realize the transformation of meiosis of germ cells into mitosis-like, wherein the proteins include a first protein, a second protein and a third protein, among them, the first protein is a protein involved in the formation of DNA double-strand break, and the first protein is a protein selected from the group consisting of:

a PAIR1 protein as shown in SEQ ID NO: 13, a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO: 14, a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO: 15, a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO: 16, a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO: 17, a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO: 18, a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO: 19, a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO: 20, a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO: 21, a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a $P31^{comet}$ protein as shown in SEQ ID NO: 22, a protein having at least 30%, 35%, 40%, 45%, 50%, 55%, 60%, 65%, 70%, 75%, 80%, 85%, 90%, 95% or 98% sequence identity with the $P31^{comet}$ protein, or a protein having at least 40%, 45%, 50%, 55%1c, 60%, 65%, 70%, 75%, 80%, 85%, 90%, 95% or 98% sequence similarity with the $P31^{comet}$ protein;

a MTOPVIB protein as shown in SEQ ID NO: 23, a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO: 24, a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

a REC8 protein as shown in SEQ ID NO: 25, a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

a OSD1 protein as shown in SEQ ID NO: 26, a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO: 27, a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein;

a TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein.

Further, the vector and/or reagent for the development of gametes into seeds or plants, among them, include a vector and/or reagent for inducing gametes to develop into seeds or plants by using gene mutation and gene engineering technology to influence the MTL protein involved in the development of gametes or embryos in plants, the MTL protein is a MTL protein as shown in SEQ ID NO: 29, a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein.

According to still another aspect of the present disclosure, a plant produced by using the above kit is provided. The meiosis of germ cells of the plant is transformed into mitosis-like so that it can produce gametes whose genotype and chromosome ploidy are consistent with hybrids.

Further, the gametes of the plants can be induced to develop into plants or seeds.

Further, the plant is a gene mutant or genetically engineered plant, the plant is used in the gene mutation or gene engineering technology to regulate proteins involved in meiosis in plants to realize the transformation of meiosis of germ cells into mitosis-like; the plant is used in the gene mutation or gene engineering technology to influence a fourth protein involved in the development of gametes or embryos in plants so as to induce gametes to develop into seeds or plants; wherein the proteins include a first protein, a second protein and a third protein, among them, the first protein is a protein involved in the formation of DNA double-strand break, and the first protein is a protein selected from the group consisting of:

a PAIR1 protein as shown in SEQ ID NO: 13, a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO: 14, a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO: 15, a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO: 16, a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO: 17, a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO: 18, a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO: 19, a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO: 20, a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO: 21, a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a P31$^{comet}$ protein as shown in SEQ ID NO: 22, a protein having at least 30%, 35%, 40%, 45%, 50%, 55%, 60%, 65%, 70%, 75%, 80%, 85%, 90%, 95% or 98% sequence identity with the P31$^{comet}$ protein, or a protein having at least 40%, 45%, 50%, 55%, 60%, 65%, 70%, 75%, 80%, 85%, 90%, 95% or 98% sequence similarity with the P31$^{comet}$ protein;

a MTOPVIB protein as shown in SEQ ID NO: 23, a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO: 24, a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

a REC8 protein as shown in SEQ ID NO: 25, a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

a OSD1 protein as shown in SEQ ID NO: 26, a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO: 27, a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein; the TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein;

a TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein;

the fourth protein is a protein selected from the group consisting of:

a MTL protein as shown in SEQ ID NO: 29, a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein.

According to still another aspect of the present disclosure, a method for maintaining plant heterosis is provided. The method includes the following steps: S1, transforming the meiosis of germ cells of the hybrid into mitosis-like during the F1 generation so as to obtain the diploid female gametes of the F1 generation by using gene editing technology; and, S2, influencing and involving in the development of gametes or embryos in plants to induce the diploid female gametes to develop into seeds by using gene mutation and gene engineering technology, wherein a protein influenced is MTL protein.

Further, the S1 includes taking hybrid F1 generation seeds, transforming the meiosis of germ cells of the hybrid into mitosis-like so as to obtain the diploid female gametes of the F1 generation by using gene editing technology.

Further, the S1 includes editing the parent of the hybrid seeds using gene editing technology to obtain plants having the edited genes which are all heterozygous mutant, and then obtaining the hybrid seeds through interparental hybridization, screening hybrid seeds having a plurality of edited genes which are all homozygous mutant in both parents, so as to obtain the diploid female gametes of the F1 generation whose meiosis of germ cells is transformed into mitosis-like.

Further, the S1 includes knocking out the REC8, OSD1, and PAIR1 genes to realize the transformation of meiosis of germ cells into mitosis-like by using gene editing technology.

Further, the S2 includes pollinating the diploid female gamete with haploid inducer pollen to induce the diploid female gametes to develop into seeds.

Further, the S2 includes knocking out the MTL genes to produce haploid inducer pollen by using gene editing technology.

Further, the S2 includes using the haploid inducer pollen from other plants to induce the diploid female gametes to develop into seeds.

Further, knocking out the REC8, OSD1, PAIR1 and MTL genes of the hybrids simultaneously during the F1 generation.

Further, the plant includes rice, maize, sorghum, millet, barley and wheat.

By applying the technical solution of the present disclosure, hybrids can produce cloned seeds whose genotypes and chromosome ploidy are completely consistent with their own, so that the hybrids can be used for a long time, and the problems such as difficulty in interparental hybridization due to the inconsistent florescence, etc., low seed production, and high cost of hybrids, etc. during the use of heterosis can be solved.

BRIEF DESCRIPTION OF THE DRAWINGS

The accompanying drawings, which form a part of this application, are provided to further understand the present disclosure, the illustrative embodiments of the present disclosure and the description thereof are intended to explain the present disclosure and are not intended to limit thereto. In the drawings:

FIGS. 2 and 3 show schematic diagrams of the genotype maintenance of F1 generation of the present disclosure;

FIG. 4A shows the cell ploidy test results of the F1 generation plant Chunyou 84 in Example 1; and FIG. 4B shows the cell ploidy test results of the heterosis fixed plants in Example 1;

DETAILED DESCRIPTION OF THE EMBODIMENTS

Figure 1A:
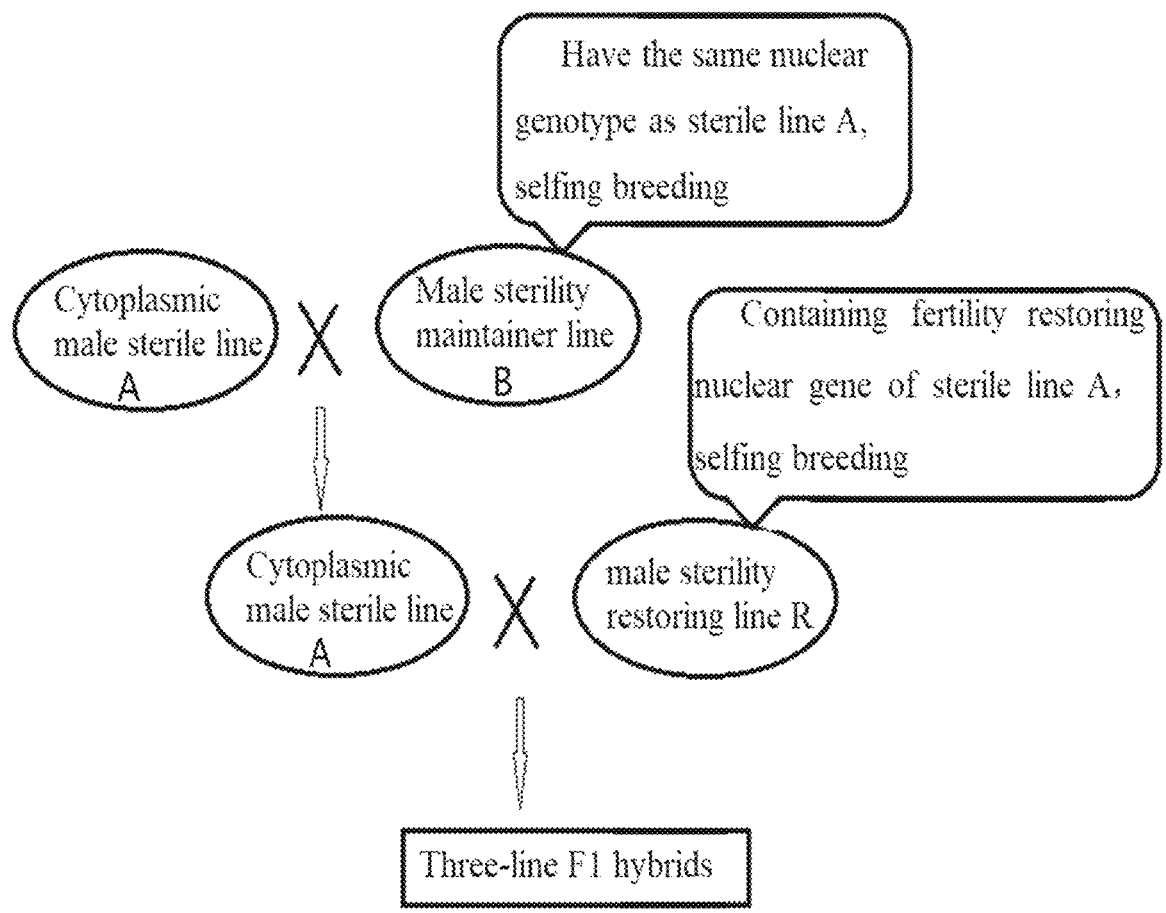
FIG. 1A shows a schematic diagram of a three-line hybrid breeding technology process in the prior art.
Figure 1B:
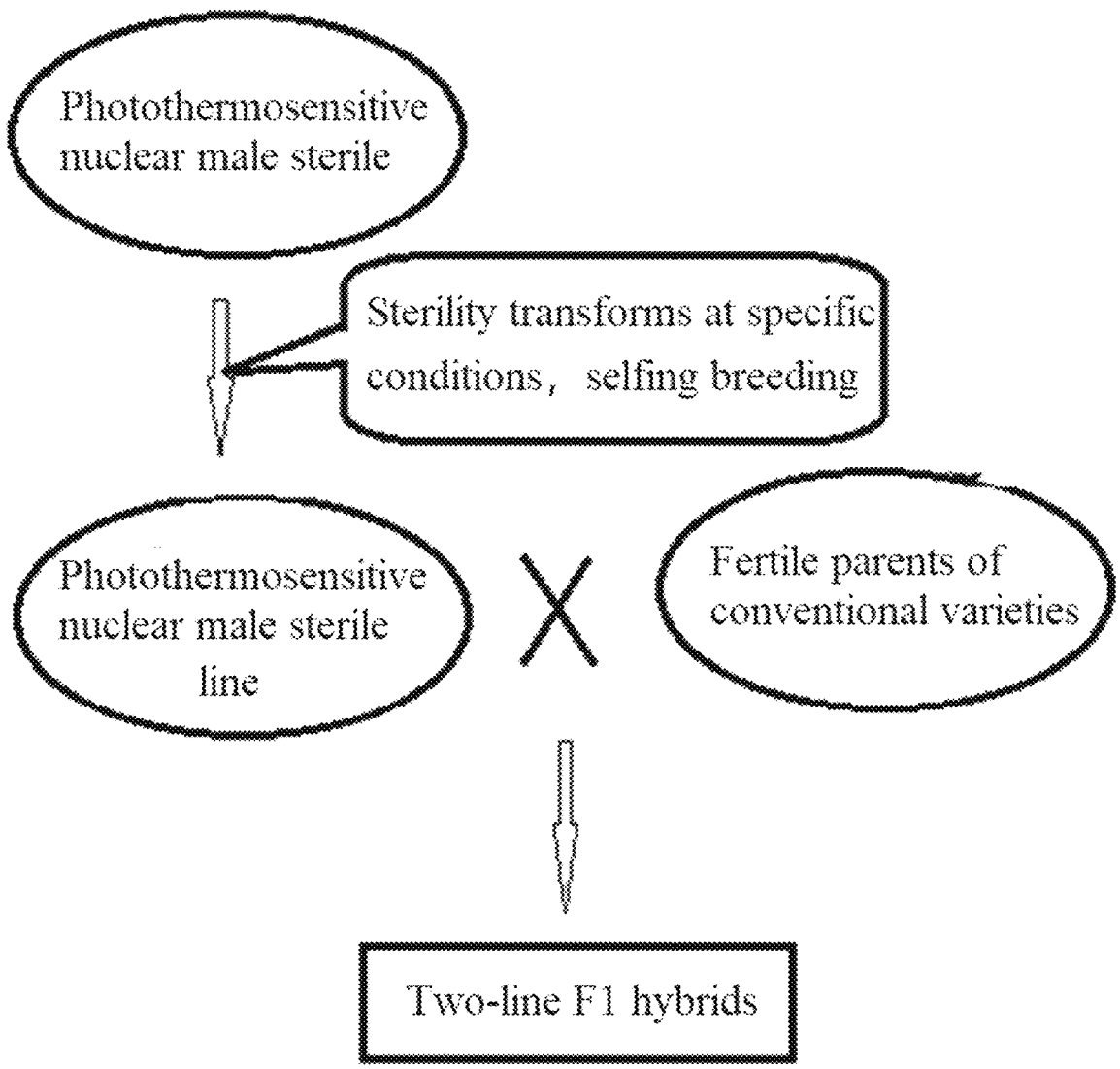
FIG. 1B shows a schematic diagram of a two-line hybrid breeding technology process in the prior art.

It should be noted that the Examples in the present application and the features in the Examples may be combined with each other without conflicting. Hereinafter, the present disclosure will be described in detail with reference to the drawings and in conjunction with the Examples.

The terminologies involved in the present disclosure are explained as follows:

Heterosis refers to the phenomenon that the first generation of hybrid is superior to the parent in terms of body size, growth rate, fecundity, and behavior characteristics.

Meiosis refers to when the germ cell divides, the chromosome duplicates only once, and the cell divides twice continuously. This is a special way of halving the number of chromosomes.

Mitosis, also known as indirect division, is discovered in plants by E. Strasburger (1880). It is characterized by the appearance of spindles and chromosomes during cell division, so that the daughter chromosomes that have been replicated in the S phase are equally distributed into the daughter cells, such way of division is commonly seen in higher plants and animals (animals and higher plants).

Chromosome ploidy (number) refers to the number of chromosomes or genomes contained in a cell, such as haploid staining and polyploid staining.

Diploid female gametes: gametes refer to genoblasts produced by the reproductive system during sexual reproduction in organisms, referred to as germ cells. Gametes include male gametes and female gametes; generally, when germ cell divides, the chromosome duplicates only once, and the cell divides twice continuously, and the number of chromosomes is halved. However, if the number of chromosomes is not halved when the female gametes are produced, but is consistent with the number of chromosome complement in the somatic cell of the species, it is called diploid female gametes.

Haploid: An individual or cell whose number of somatic chromosome complement is equal to the number of gamete chromosome complement of the species.

Parthenogenesis, also known as autogenesis, refers to eggs can develop into normal new individuals without being fertilized.

In the present disclosure, hybrids refer to plants or seeds whose genotypes are heterozygous, and the progenies of their sexual reproduction will be genetically segregated.

According to a typical embodiment of the present disclosure, a method for using plant heterosis is provided. The method includes the following steps: S1, transforming the meiosis of germ cells of hybrids into mitosis-like so as to obtain gametes whose genotype and chromosome ploidy are consistent with hybrids by using gene mutation or gene engineering technology; and S2, influencing and involving in the development of gametes or embryos in plants by using gene mutation and gene engineering technology, wherein a protein influenced is MTL protein.

Wherein, the gene mutation includes random mutagenesis and directed mutagenesis; the random mutagenesis includes chemical mutagenesis, physical mutagenesis, and biological mutagenesis; the directed mutagenesis includes gene editing technology, preferably, the gene editing technology includes CRISPR/Cas gene editing technology, CRISPR/Cpf1 gene editing technology, TALEN gene editing technology, homing endonuclease gene editing technology and ZFN gene editing technology; the gene engineering technology includes transgene technology to induce specific expression, ectopic expression or gene silencing of genes.

Specifically, commonly used methods in physical mutagenesis include rays (ultraviolet rays, X-rays, Y-rays, neutron rays), laser microbeams, ion beams, microwaves, ultrasound, and heat, etc. Commonly used methods in chemical mutagenesis include immersion method, smear method, drip method, injection method, application method and fumigation method. Chemical mutagens include: an alkylating agent, a base analogue, lithium chloride, a nitroso compound, an azide, an antibiotic, hydroxylamine, acridine, diethyl sulfate (DFS), 5-bromouracil (5-BU), nitrogen mustard (Nm), N-Methyl-N'-nitro-N-nitrosoguanidine (NTG), etc. Biological mutagenesis methods include space condition treatment mutagenesis, pathogenic microorganism mutagenesis, tissue culture mutagenesis, and transgenic mutagenesis.

As an example, the application can be TILLING (Targeting Induced Local Lesions IN Genomes), described by McCallum et al., Plant Physiology, 2000, 123, 439-442). Directed mutagenesis is performed using standard techniques, which are known in the art and utilize homologous recombination, preferably in combination with nucleases such as TALEN or CRISPR.

According to a typical embodiment of the present disclosure, the method includes the following steps: S1, transforming the meiosis of germ cells of hybrids into mitosis-like so as to obtain gametes whose genotype and chromosome ploidy are consistent with hybrids by using gene mutation or gene engineering technology, and S2, inducing the gametes to develop into seeds or plants.

By applying the technical solution of the present disclosure, hybrids can produce cloned seeds or plants whose genotypes and chromosome ploidy are completely consistent with their own, so that the hybrids can be used for a long time, and the problems such as difficulty in interparental hybridization due to the inconsistent florescence, etc., low seed production, and high cost of hybrids, etc. during the use of heterosis can be solved.

According to a typical embodiment of the present disclosure, the S1 includes taking hybrid seeds, transforming the meiosis of germ cells of hybrids into mitosis-like so as to obtain gametes whose genotype and chromosome ploidy are consistent with hybrids by using gene mutation or gene engineering technology. For example, the specific operation can be: S1 includes taking hybrid F1 generation seeds, transforming the meiosis of germ cells into mitosis-like so as to obtain the diploid gametes of the F1 generation by using gene engineering technology. The specific operation can be: taking hybrid F1 generation seeds, editing the key genes involved in meiosis by introducing the gene editing system to obtain the gene-edited F1 generation plants, the female gametes of the gene-edited F1 generation plants are diploid gamete, preferably, the key genes involved in meiosis are the three genes REC8, OSD1, and PAIR1.

According to a typical embodiment of the present disclosure, the S1 includes editing the parent of the hybrid seeds using gene mutation or gene engineering technology, and then obtaining the hybrid seeds through interparental hybridization, so as to obtain hybrid gametes whose meiosis of germ cells is transformed into mitosis-like. For example, the specific operation can be: S1 includes editing the parents of the hybrid seeds using gene engineering technology to obtain plants having key genes involved in meiosis are all heterozygous mutants, and then obtaining the hybrid seeds through interparental hybridization, screening hybrid seeds having key genes involved in meiosis are all homozygous mutant, so as to obtain the diploid female gametes of the F1 generation whose meiosis of germ cells is transformed into mitosis-like. The specific operation can be: taking the male parent and female parent of the hybrid seeds, respectively, editing the above three key genes involved in meiosis by introducing a gene editing system, so as to obtain parent plants whose the above three gene-edited genes are all in a heterozygous state, then hybridizing the two parents, the resulting seeds will show different genotypes, among them, selecting seeds whose the above three genes are homozygous mutations. Such plants are the F1 generation seeds that are expected by the present disclosure, and the female gametes of the F1 generation seeds are diploid female gametes.

According to a typical embodiment of the present disclosure, the S1 includes editing proteins involved in meiosis in plants to realize the transformation of meiosis of germ cells into mitosis-like by using gene mutation or gene engineering technology; wherein the proteins include a first protein, a second protein and a third protein, among them, the first protein is a protein involved in the formation of DNA double-strand break, and the first protein is a protein selected from the group consisting of:

a PAIR1 protein as shown in SEQ ID NO:13 (MKLKMNKACDIASISVLPPRRTGGSSGASASGSVA-VAVASQPRSQPLS QSQQSFSQGASASLLHSQSQF- SQ-VSLDDNLLTLLPSPTRDQRFGLHDDSSKRMSSLPAS SASCAREESQLQLAKLPSNPVHRWNPSIADTRSGQV-TNEDVERKFQHLASSVHKMG MVVDSVQSDV-MQLNRAMKEASLDSGSIRQKIAVLESSLQQILKGQD-DLKALFGSSTK HNPDQTSVLNSLGSKLNEISST-LATLQTQMQARQLQGDQTTVLNSNASKSNEISSTLA TLQTQMQADIRQLRCDVFRVFTKEMEGVVRAIRSV-NSRPAAMQMMADQSYQVPVS NGWTQINQTPV-AAGRSPMNRAPVAAGRSRMNQLPETKVLSAHL-VYPAKVTDLKPKV EQGKVKAAPQKPFASSYYRVA-PKQEEVAIRKVNIQVPAKKAPVSIIIESDDDSEGRASC VILKTETGSKEWKVTKQGTEEGLEILRRARKRRRRE-MQSIVLAS), a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO:14 (MVMAQKTKEAEITEQDSLLLTRNLLRIAIYNISYIR-GLFPEK YFNDKSVPALEMKIKKLMPMDTESRRLI-DWMEKGVYDALQKKYLKTLLFCICEKEE GPMIE-EYAFSFSYPNTSGDEVAMNLSRTGSKKNSATFKS-NAAEVTPDQMRSSACKMIR TLVSLMRTLD-QMPEERTILMKLLYYDDVTPEDYEPPFFKCCAD-NEAINIWNKNPLKM EVGNVNSKHLVLALKVKS-VLDPCDDNNVNSEDDNMSLDNESDQDNDFSDTE-VRPSE AERYIVAPNDGTCKGQNGTISEDDTQDPV-HEEELTAQVREWICSRDTESLEVSDVLVN FPDIS-MEMVEDIMERLLKDGLLSRAKKDSYSVNKIADP-TTPHIKKEVIMQNVSPTEGT KNSNGDLMYMKALYH-ALPMDYVSVGKLHGKLDGEASQNMVRKLIE-KMVQDGYVK NSANRRLGKAVIHSEVTNRKLLEIK-KILEVDIAEQMAIDTNAEPGEPERKDHLSGHEM RDGSTMGCLQSVGSDLTRTRELPEPQQNVSMQSG-QEASTVDKDPSRTPTSVREASVCSLESGVLGQK-VRKSLAGAGGTQCSQDKRFRKASTVKEPILQYVK-RQKSQVQVQVQ), a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO:15 (MEVELT-NIQKATSSDYWSLASNQYPCGKFPKVSVGVTIPRT-SSVSR GRDAASTAAFEKNLSQGTDGRSRPPKMDNA-SLQVSPEAANHGGSAKEVPKPVPAKV SVSQPDDNA-IEQTGTFSFGTRREQDSHLDQLDRPPLVSSQGKRQ-VESADKNKPNSEMLRMKLWEILGGTSQNKEAV-ASPNPEDIETPCQPKSQIANGPSSGRQKVFTSPVPY-NIKT PAQFNSQTANKPSSDPIESDSDSPQVVEVRP-ITRSLGRKKEPTGSTHQDKSGSAKKPLS THRSTPK-QKILDNVFAFNDKCTPKTVGKSANGESGSLRNLRSL-SRRAKVEPKKAHCS DRISHKTTQDDMERKVPSKY-IPSEKKGEKTNSFSSLSRTGKTAESCSRSPKRERRVNT MANVGARKMQLSENLLVKTLNDGEHKLSSPQLT-SFKSKGKCSSISPQQKENDNTHIPE ASDRTAARNSFN-STPSPAANPSPVLRKYSWEHDENPAINGKSGQKDAS-PLADRFSDMP DDFASPTFAANIKISPHRSKML-DDDLFSSKYPKGVNRSRSTSFTSDPESEPLDKMEKTN ELPGSESPNSQEERQNRKQPHLSPLSPIESEGAQI-SIPSFRKGYKSHKWLSDVDSPDKSS IEHLGRK-SHLKEGRKGKRQLTSPTHFATSGTQETMSDKE-PEKVPENYLTRAFDQLVVV LGRFQTKIKSETR-NKSSKILAATGEIIRQHLEGVEGQMQADVDKLV-NAGKSKRKRLES TFEEQQEKLRILHEKFKEEVN-QQLLGCKNSVEDFEAYHAELKGVADKQKASHKKL-LQ NAEKTVGAQLSDAETKIAEVQKRARKRMKG-LKFVLKELIAETAE), a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO:16 (MEMVLIMSFRVLLYHRLTAQTGPFKLHCLGILLN-STKDAATYIGDKQ SLYLNLVNNLRLPSDEIRGEIL-FVLYKLSLLNATPWDDICDNDNVDLSAIGRSLLQF-SLE VLLKTQNDDVRLNCIALLLTLAKKGAFDILLL-SDPSLINSAEAEDNVPLNDSLVILFAE AVKGSLLST-NIEVQTGTLELIFHFLSSDANIFVLKTLIDQNVADY-VFEVLRLSGMRNHL LQSSNASQFLTKLLYVSGNND-PLVISSIKVLSILANSEERFKEKLAIAVSTLLPVLHYVS EIPFHPVQSQVLRLVCISIINCSGILSLSQEEQIACTL-SAILRRHGNGELGMSSETFALVCS MLVEILKLPSAD-DIQKLPSFIVEASKHAISLTFSHEYDCLFLIPHSLLL-LKEALIFCLEGN KDQILRKKSLEDSIIETCETYLL-PWLESAIVDGNDEETLSGILQIFQIILSRASDNKSFKF AEMLASSSWFSLSFGFMGLFPTDHVKSAVYLVIS-SIVDKVLGISYGETIRDACIYLPPDP AELLYLLGQ-CSSEDFNLASCQCAILVILYVCSFYNERLAADNQI-LASVEQYILLNGAKF PHEIPGSLMLTLLVHLYAFVRG-ISFRFGIPHSPEAEKTLFHAMTHKEWDLLLIRVHLIAL KWLFQNEELMEPLSFHLLNFCKFFCEDRTVMLS-SSTQLVDIQLIAELVYSGETCISSLLV SLLSQMIKE-SAEDEVLSVVNVITEILVSFPCTSDQFVSCGIVDAL-GSIYLSLCSSRIKSVC SLLIFNILHSASAMTFTCDD-DAWLALTMKLLDCFNSSLAYTSSEQEWKILIGILCLI-LNH SANKVLIEPAKAIILNNCLALLMDGIVQEAC-AKGPSLFQHNQETTFGELLILMLLLIFFS VRSLQA-ILEASIDWQEFLQYSDDTESSSVLGIPCHDLCRLMH-FGPSPVKLIASQCLLEL LNRISDQRSCLNAELRCSA-KYLKSMIAVTEGMVFDQDSRVAENCGACLTVILGW-ERF GSREKAVIRESKWSRLILEEFAVALTAPGLTSKS-FSNQQKIAANIALSLLQLSQVPDWLT SLFSDSLISGI-VANLSARNVTAEIVTLFSELMAKNYLNQEHIAGLH-NLFQVCRRQAYEG GGGSKAQPSEQKAAAARCAD-DVRALLFGMMLEQRACSRATVEMEQQRLLREIDSFF FQESSLREQNSVK), a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO:17 (MAPPAS-RPPTPTPTPTANAAASSSRIESPSLRAALAMALIHYN-RLP SRAAAAAAPSPQALLNWKRKAKDRKREILRL-REELKLLQDGARGEEMEPPVASCRC HFFDGCG-DLPPPTDGDAGEHWVDDVLRRRFVRLVRWKDK-RRRLDRSLPTSSLMEYN TEDEVQQLSLSIDFLVEL-SDGLFAKREAGSSFTTFSHQAVDFILASLKNILSSER-EKEIIE EIINGLVARLMKRMCTTPENAGSVDCSDA-QFSLQHLFRKLGNEEFVGQRIILAISQKIS NVSEKLL-LADPFDDGFPEMHSNMFIMIQLIEFLISDSFNNWL-CRDHFDRKLFEEWVRSI LKARKDLEVLDGRNGLYV-VYIERVIGRLAREVAPAAHQGKLDLEVLSKLLY), a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO:18 (MAGREKRRRVAALDGEERRRRQEEAATLLHRIRGL-VRWV VAEVAAGRSPTVALHRYQNYCSSASAAAASP-CACSYDVPVGTDVLSLLHRGSHASRL NVLLRVLL-VVQQLLQQNKHCSKRDIYYMYPSIFQEQAVVDRA-INDICVLFKCSRHNL NVVPVAKGLVMGWIRFLEG-EKEVYCVTNVNAAFSIPVSIEAIKDVVSVADYILI-VEKE TVFQRLANDKFCERNRCIVITGRGYPDIPTR-RFLRYLVEQLHLPVYCLVDADPYGFDIL ATYKFGS-LQLAYDANFLRVPDIRWLGVFTSDFEDYRLPDCCL-LHLSSEDRRKAEGILS RCYLHREAPQWRLELEAML-QKGVKFEIEALSACSISFLSEEYIPKKIKQGRHI), a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO:19 (MAEAGVAAASLFGADRRLCSADILPPAEVRARIEVA-VLNFLAALTD PAAPAISALPLISRGAANRGLRRA-LLRDDVSSVYLSYASCKRSLTRANDAKAFVRVWK VMEMCYKILGEGKLVTLRELFYTLLSESPTYFTC-QRHVNQTVQDVVSLLRCTRQSLGI MASSRGALI-GRLVVQGPEEEHVDCSILGPSGHAITGDLNVLSK-LIFSSDARYIIVVEKD AIFQRLAEDRIYSHLPCILITA-KGYPDLATRFILHRLSQTYPNMPIFALVDWNPAGLAIL CTYKYGSISMGLESYRYACNVKWLGLRGDDLQLI-PQSAYQELKPRDLQIAKSLLSSKF LQDKHRAELTLM-LETGKRAEIEALYSHGFDFLGKYVARKIVQGDYI), a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO:20 (MPPTM-LASVPTRPRSHPFRRRRGAAAAAPPLLPDQIAAA-AAAAAKRP AESSTSASSCFHSEVISATSTTCPTSLA-AAQRPEKRPRYQDVDEEQPAASECSEIIGGAR PRAA-EVEVSESSCLASVLESYLACPEQLANDAETTAY-SSAREDLTLSETEEEEEEEEVR SGPCICTDCSFSPL-HESSSSSDDDNAVPSPTFSLFLALAEQFVPFTHPKTP-TATDVALQA GEGKRFEDLDNEVSYERFRRRERRG-VVARDYIEVYSSMLGSYGRAVVEQRVVMVNW IME-HSQAMKLQPETVFMGIGLMDRFLTRGYVKG- SRNL-QLLGIACTTLATRIEENQPYN CILQKAFKVGINTYSR-SEVVAMEWLVQEVLDFQCFVTTTHHFLWFYLKAA-NADDRVE DLAKYLALLSLLDHKHLSFWPSTVA-AAVVALACLATNNESSCHLVMETHMRTKNDD LPE-CLMSLEWLTNYAS), a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO:21 (MSAP-MEVSFSAPPPPDAASAAAAAPSLVPAVSAAAVAATT-VSCS PQPPTGSPSADDRILVSVEVLLHATSTARAEDV-CAAVERMLEARSLSYVDGPVPIPND DPFLLANVK-RIQICDTDEWTENHKVLLFWQVRPVVHVFQLS- ED-GPGEEPGEDDTLSS FNEWALPAKEFDGLWESLLYE-VGLKQRLLRYAASALLFTEKGVDPCLVSWNRIVLLH GPPGTGKTSLCKALAQKLSIRFKSRYSMCQLIEVNA-HSLFSKWFSESGKLVAKLFQKIQ EMVEEESN- LVF-VLIDEVESLAAARQAAISGSEPSDSIRVVN- ALL-TQMDKLKSWPNVIIL TTSNITTAIDIAFVDRADIKAY-VGPPTLQARYEILRSCLQELLRVGILTHTQGGNSLCLL SYFSLMENQHCPEVADPHGSVHLSGLLHKAAE-ICEGLSGRTLRKLPFLAHASVANPSC CDASAFLHAL-IQTAQRELSESRG), a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a P31$^{comet}$ protein as shown in SEQ ID NO:22 (MER-ATTSGGGGGGSQPPRGVGLPLVEVQAAAASLRRSE-VFYVVKE LLGFVLYMHHQIPAVLQNLENEFASLKEE-MTEMALPPGEMKPSDQRKYNTRKREVRR RIKKQE-KLMNGLSSVFSALQKALDEVPSIEGVLLILGGSLVR-PLFVYDITISHGRFDAG SANERGASKLAQSVSRKAI-RALISSGAGSLSYTGPTKLFVLVRCPCTLNLPLDFL-PKRD FRYSKKVVPLQMCIKCNIAGIQIDNQQITSIV-DASRCTSESTISEVIWFQCKHTIRGLPC KASLEE), a protein having at least 30%, 35%, 40%, 45%, 50%, 55%, 60%, 65%, 70%, 75%, 80%, 85%, 90%, 95% or 98% sequence identity with the P31$^{comet}$ protein, or a protein having at least 40%, 45%, 50%, 55%, 60%, 65%, 70%, 75%, 80%, 85%, 90%, 95% or 98% sequence similarity with the P31$^{comet}$ protein;

a MTOPVIB protein as shown in SEQ ID NO:23 (MASSPPPSTASPTSSSPYRKLLHSLIYWAVQRCRMS-ESPCRLTVSVKR SPEPAGSSPLRISVSDTGVGSKLE-EFLELDALARETPVEKWDGTLLITTGIDDKAIYRY QFNLQEDTSSSTRFTKLATMYKSRAIFSGTEVCLCLP-TEADVDDLILWLVGFVRKIFVL RASNLACELFVA-QTDSAGSGDVCLSQDSDDVHISITTSSIDRLVSGL-KDYALSHANTSD RCEACYMNRDRLKIGTGTAKY-VDKRKAKGQLVEVVIMIAPTSSDLSCWMTNCSSTQ VLHFVEFIPCPISQSSLSALMSIDWQSYGFKFKGG-FIDDDGNAELQWDNMAFSHVDIA IHTYHEGAVDE-WKSSQPERHLLRKALKSALFGLKADHAEDFLSCH-GQKVREYVPDL AESIAGLILSSNDQEFQDECIALLG-LGSDQDLTEGAVRSCIGEKMNRIIEMNDTKENVE HN-APYLFECERFDEDYSLLDEDDPDEDMIFDF), a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO:24 (MRHNIKFK-SKGTLKIRNTAQISLWKKCSDSMIADQTYLFINRV-QDRR FDEESLRILELSLVAMNVKSFLEVRSRLRDF-MRSESVVIFGELTGESMVAKLSVLEFFA RAFALLGD-MESCLAMRYEALNLRQLKSPSCLWLGVSHSEWTK-FAVQSMENGFPSIAG KASENALLSLKKDSLIEPKS-EDNSDILDAAEKVRRLRDSAASLTSSHSGIFIYIVS-SLKFA VCNRLLTTF), a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

a REC8 protein as shown in SEQ ID NO:25 (MFYSHQL-LARKAPLGQIWMAATLHSKINRKRLDKLDIIKICEE-ILN PSVPMALRLSGILMGGVAIVYERKVKALYDD- VSRFLIEINEAWRVKPVADPTVLPKGKTQAKYEAVTLPENIMDMDVEQPMLFSEADTTRFRGMRLEDLDDQYINVNLDDDDFS RAENHHQADAENITLADNFGSGLGETDVFNRFERFDITDDDATFNVTPDGHPQVPSNLVPSPPRQEDSPQQQENHHAASSPLHEEAQQGGASVKNEQEQQKMKGQQPAKSSKRK KRRKDDEVMMDNDQIMIPGNVYQTWLKDPSSLITKRHRINSKVNLIRSIKIRDLMDLP LVSLISSLEKSPLEFYYPKELMQLWKECTEVKSPKAPSSGGQQSSSPEQQQRNLPPQAF PTQPQVDNDREMGFHPVDFADDIEKLRGNTSGEYGRDYDAFHSDHSVTPGSPGLSRR SASSSGGSGRGFTQLDPEVQLPSGRSKRQHSSGKSFGNLDPVEEEFPFEQELRDFKMR RLSDVGPTPDLLEEIEPTQTPYEKKSNPIDQVTQSIHSYLKLHFDTPGASQSESLSQLAH GMTTAKAARLFYQACVLATHDFIKVNQLEPYGDILISRGPKM), a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

an OSD1 protein as shown in SEQ ID NO:26 (MPEVRNSGGRAALADPSGGGFFIRRTTSPPGAVAVKPLARRA LPPTSNKENVPPSWAVTVRATPKRRSPLPEWYPRSPLRDITSVVKAVERKSRLGNAAV RQQIQLSEDSSRSVDPATPVQKEEGVPQSTPTPPTQKALDAAAPCPGSTQAVASTSTAY LAEGKPKASSSSPSDCSFQTPSRPNDPALADLMEKELSSSIEQIEKMVRKNLKRAPKA AQPSKVTIQKRTLLSMR), a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO:27 (MSSSSRNLSQENPIPRPNLAKTRTSLRDVGNRRAPLGDITNQKN GSRNPSPSSTLVNCSNKIGQSKKAPKPALSRNWNLGILDSGLPPKPNAKSNIIVPYEDT ELLQSDDSLLCSSPALSLDASPTQSDPSISTHDSLTNHVVDYMVESTTDDGNDDDDDEI VNIDSDLMDPQLCASFACDIYEHLRVSEVNKRPALDYMERTQSSINASMRSILIDWLVE VAEEYRLSPETLYLAVNYVDRYLTGNAINKQNLQLLGVTCMMIAAKYEEVCVPQVED FCYITDNTYLRNELLEMESSVLNYLKFELTTPTAKCFLRRFLRAAQGRKEVPSLLSECL ACYLTELSLLDYAMLRYAPSLVAASAVFLAQYTLHPSRKPWNATLEHYTSYRAKHME ACVKNLLQLCNEKLSSDVVAIRKKYSQHKYKFAAKKLCPTSLPQELFL), a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein;

a TDM1 protein as shown in SEQ ID NO:28 (MCPCVERRAPPGVYYTPPPARTSDHVAAMPMTERRRPPYSCSSSSE RRDPFHIVHKVPSGDSPYVRAKHAQLIDKDPNRAISLFWTAINAGDRVDSALKDMAV VMKQLGRSDEGIEAIKSFRYLCSFESQDSIDNLLLELYKKSGRIEEEAVLLEHKLQTLE QGMGFGGRVSRAKRVQGKHVIMTIEQEKARILGNLGWVHLQLHNYGIAEQHYRFGF VTKIPNIDYCLVMRALGLERDKNKLCNLAICLMRMSRIPEAKSLLDDVRDSPAESECG DEPFAKSYDRAVEMLAEIESKKPEADLSEKFYAGCSFVNRMKENIAPGTANKNYSDVS SSPASVRPNSAGLYTQPRRCRLFEEETRGAARKLLFGKPQPFGSEQMKILERGEEEPM KRKKLDQNMIQYLHEFVKDTADGPKSESKKSWADIAEEEEAEEEEEERLQGELKTAE M), a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein.

Among them, the PAIR1 protein is involved in the initiation of meiotic recombination and catalyzes the formation of DNA double-strand gaps. The deletion of the PAIR1 gene will cause the loss of the recombination process; the REC8 protein is responsible for closely linking the newly duplicated sister chromosomes and is a key regulatory factor that guarantees sister (or homologous) chromosomes to be correctly separated and assigned to the daughter cells. The loss of its function will cause the sister chromatids to separate at the end of the first meiotic division and move to the bipolar, the loss of the function of OSD1 gene will cause the formation of gametes to skip the second meiotic division process directly.

Knockout of the above-mentioned gene is a simple and effective method to transform the meiosis of germ cells into mitosis-like.

The suppression of the protein in the present disclosure refers to the mutagenesis of the gene encoding the protein or its promoter, and the selection of partial or complete loss of protein activity, including obtaining the suppression of related proteins by expressing silencing RNA in plants.

According to a typical embodiment of the present disclosure, the S2 includes influencing and involving in the development of gametes or embryos in plants, and induce the gametes to develop into seeds or plants by using gene mutation and gene engineering technology. In addition, S2 may include pollinating induced pollen from other plants to induce the gametes to develop into seeds or plants. For example, S2 includes pollinating the diploid female gamete with haploid inducer pollen to induce the diploid female gametes to develop into seeds; as another example, S2 includes inducing the gametes to develop into seeds or plants through physical stimulation, biotic stress, or chemical agent treatment; as another example, S2 includes inducing the gametes to develop into seeds or plants through anther culture or pollen culture.

Preferably, MTL protein is a MTL protein as shown in SEQ ID NO:29 (MAASYSCRRTCEACSTRAMAGCVVGEPASAPGQRVTLLAIDGGGIRGLIPGTILAFLE ARLQELDGPDARLADYFDCIAGTSTGGLITAMLAAPGDHGRPLFAASDINRFYLDNGP LIFPQKRCGMAAAMAALTRPRYNGKYLQGKIRKMLGETRVRDTLTNVVIPTFDVRLL QPTIFSTYDAKSMPLKNALLSDICISTSAAPTYLPAHCFQTTDDATGKVREFDLIDGGVAANN- PTMVAMTQITKKIMVKDKEELYPVKPSDCGKFLVLSVGTGSTSDQGMYTARQ CSRWGIVRWLRNKGMAPIIDIFMAASSDLVDIHAAVMFQSLHSDGDYLRIQDNTLHG DAATVDAATRDNMRALVGIGERMLAQRVSRVNVETGRYVEVPGAGSNADALRGFAR QLSEERRARLGRRNACGGGGEGEPSGVACKR), a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein. Wherein, the inducer pollen can be originated from plants that produce gametes whose genotype and ploidy are consistent with the hybrid, also can be originated from other plants. Preferably, the inducer pollen is originated from plants that produce female gametes whose genotype and ploidy are consistent with the hybrid, and is achieved by knocking out REC8, OSD1, PAIR1 and MTL genes simultaneously in the hybrid.

According to a typical embodiment of the present disclosure, plants include monocotyledonous plants and dicotyledonous plants; preferably, plants include rice, maize, sorghum, millet, barley, wheat, rye, oats, buckwheat, coix seed, sugar cane, asparagus, bamboo shoots, *Allium tuberosum*, yams, soybeans, potatoes, peas, mung beans, adzuki beans, *Vicia faba, Vigna sesquipedalis, Phaseolus vulgaris, Lens culinaris, Calopogonium mucunoides*, chickpeas, cassava, sweet potato, rape, cotton, beets, eggplant, peanuts, tea, mint, coffee, sesame, sunflower, *Ricinus communis*, perillaseed, safflower, tomato, pepper, cucumber, *Brassica chinensis*, lettuce, spinach, garlic, *Brassica oleracea, Brassica juncea, Zizania aquatica*, welsh onion, *Benincasa hispida*, zucchini, loofah, chinese cabbage, radish, onion, watermelon, grape, carrot, cauliflower, pumpkin, tobacco, pasture, *Pennisetum purpureum* schumach, *Pennisetum alopecuroides, Sorghum sudanense*, orchids, lilies, tulips and alfalfa.

The implementation principle of the present application is as follows:

the principle of apomixis in the present application is to directly form embryos and produce seeds by bypassing the process of meiosis and fertilization, which is mainly divided into two major steps:

the first step: meiosis is a special cell division process that occurs during the reproduction period of animals and plants. During meiosis, the genetic information from the parents will be recombined to produce gametes with the number of chromosomes halved.

After the genes involved in three different important stages of plant meiosis are mutated simultaneously (this three-mutated material is named as MiMe, Mitosis instead of Meiosis), the meiosis of the plant will be transformed into a process similar to mitosis.

The number of chromosomes and genotypes in the female and male gamete cells produced by MiMe plants are exactly the same as somatic cells. Their self-bred progenies are all genotypic heterozygous tetraploid, which proves that by mutating three genes simultaneously, hybrid plants can bypass the process of meiosis to produce cloned gametes whose genotype are consistent with the somatic cells.

Step 2: The pollen-specific phospholipase gene (MATRILINEAL, MTL) mainly acts on plant male gametes. It is a gene that controls the induction of haploids. It was first cloned in maize. The haploid inducing material mtl can be obtained by knocking out the MTL gene. In the process of double fertilization, the genome of the mtl male gamete in the zygote is degraded, that is, the paternal sperm nucleus does not form a zygote with the receptor egg nucleus, which induces haploid egg nucleus to seed-set.

Therefore, by modifying the four endogenous genes MiMe and MTL in plants simultaneously, a Fix (Fixation of hybrids) material that can undergo apomixis is obtained, that is, by bypassing the process of meiosis and fertilization to preserve the maternal genome, a plant whose cell ploidy is diploid and whose genotype is exactly the same as that of the parent is obtained. This proves that by modifying four endogenous genes simultaneously, apomixis characteristics can be introduced into hybrid plants to achieve the fixation of heterozygous genotypes.

According to a typical embodiment of the present disclosure, it includes the following steps: 1) transforming meiosis during gamete formation into mitosis-like. The study has found that when the three genes REC8, OSD1, and PAIR1 involved in meiosis stage are knocked out simultaneously (this material is named as MiMe, Mitosis instead of Meiosis), the chromosome duplicates only once, and the germ cell divides once instead of dividing twice originally, in the resulting gametes, the number of chromosomes has not halved, and is consistent with somatic cells. That is, transforming meiosis into mitosis-like to achieve the purpose of doubling the chromosomes; 2) the female gametes produced are stimulated by pollen that can induce the development of female gametes, that is, the female gametes can develop into embryos without fusion with the chromosomes of sperm cells, forming seeds having genotypes that are exactly the same as the somatic cells. Knocking out MTL gene can obtain pollen that induces haploid production. Using hybrid seeds as transgenic background, knocking out the four genes REC8, OSD1, PAIR1 and MTL simultaneously by using gene mutation or gene engineering technology. The female gametes produced by this plant have the same chromosomal ploidy as somatic cells, and due to the destruction of MTL gene, the pollen produced can induce the female gametes to develop into seeds or plants, so that the seeds or plants obtained do not undergo gene isolation (separation of traits or fertility), and the genotypes are exactly the same as mother cells (the background material hybrids used for transgenosis), and finally achieving the purpose of fixing heterosis.

FIGS. 2 and 3 clearly show that the genotype and chromosome ploidy of F1 filial generation of the present disclosure are consistent with the hybrid mother cells.

According to a typical embodiment, a plant or seed that maintains heterosis is provided. The plant or seed is prepared by any of the above methods, the seed can well fix the heterosis.

According to a typical embodiment, a kit for maintaining heterosis in plants is provided. The kit includes a vector and/or reagent capable of transforming meiosis of germ cells in plants into mitosis-like, and a vector and/or reagent for the development of gametes into seeds or plants. Preferably, the vector and/or reagent capable of transforming meiosis of germ cells in plants into mitosis-like and the vector and/or reagent for inducing parthenogenesis of plant gametes are vector and/or reagent for random mutagenesis or directed mutagenesis. Wherein, the random mutagenesis includes chemical mutagenesis, physical mutagenesis, and biological mutagenesis; the directed mutagenesis includes CRISPR/Cas gene editing technology, CRISPR/Cpf1 gene editing technology, TALEN gene editing technology, homing endonuclease gene editing technology and ZFN gene editing technology; the gene engineering technology includes transgene technology to induce specific expression, ectopic expression or gene silencing of genes.

According to a typical embodiment, the vector and/or reagent capable of transforming meiosis of germ cells in plants into mitosis-like is a vector and/or reagent used in gene engineering technology to suppress proteins involved in meiotic recombination in plants to realize the transformation of meiosis of germ cells into mitosis-like, wherein the proteins include a first protein, a second protein and a third protein, among them, the first protein is a protein involved in the formation of DNA double-strand break, and the first protein is a protein selected from the group consisting of:

a PAIR1 protein as shown in SEQ ID NO: 13, a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO: 14, a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO: 15, a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO: 16, a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO: 17, a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO: 18, a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO: 19, a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO: 20, a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO: 21, a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a P31$^{comet}$ protein as shown in SEQ ID NO: 22, a protein having at least 30%, 35%, 40%, 45%, 50%, 55%, 60%, 65%, 70%, 75%, 80%, 85%, 90%, 95% or 98% sequence identity with the P31$^{comet}$ protein, or a protein having at least 40%, 45%, 50%, 55%, 60%, 65%, 70%, 75%, 80%, 85%, 90%, 95% or 98% sequence similarity with the P31$^{comet}$ protein;

a MTOPVIB protein as shown in SEQ ID NO: 23, a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO: 24, a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

a REC8 protein as shown in SEQ ID NO: 25, a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

a OSD1 protein as shown in SEQ ID NO: 26, a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO: 27, a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein;

a TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein.

Further, the vector and/or reagent for the development of gametes into seeds or plants, among them, include a vector and/or reagent for inducing gametes to develop into seeds or plants by using gene mutation and gene engineering technology to influence the MTL protein involved in the development of gametes or embryos in plants, the MTL protein is a MTL protein as shown in SEQ ID NO: 29, a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein.

For the convenience of sale and use, preferably, the kit contains vector and/or reagent for simultaneously knocking out REC8, OSD1, PAIR1 and MTL genes in hybrids.

According to a typical embodiment, a plant is provided. The meiosis of germ cells of the plant is transformed into mitosis-like so that it can produce gametes whose genotype and chromosome ploidy are consistent with hybrids; for example, the meiosis of germ cells of the plant is transformed into mitosis-like so that it can produce gametes whose chromosome ploidy and genotype are consistent with hybrids. Preferably, plants can induce gametes to develop into plants or seeds.

According to a typical embodiment, the plant is a genetically mutanted or genetically engineered plant, proteins involved in meiosis in plants are regulated to realize the transformation of meiosis of germ cells into mitosis-like by the gene mutation or gene engineering technology; the MTL protein involved in the development of gametes in plants is influenced by gene mutation or gene engineering technology so as to induce gametes to develop into seeds or plants; wherein the proteins include a first protein, a second protein and a third protein, among them, the first protein is a protein involved in the formation of DNA double-strand breaks, and the first protein is a protein selected from the group consisting of:

a PAIR1 protein as shown in SEQ ID NO: 13, a protein having at least 30%, 35%, 40%, 45%, 50%, 55%, 60%, 65%, 70%, 75%, 80%, 85%, 90%, 95% or 98% sequence identity with the PAIR1 protein, or a protein having at least 40%, 45%, 50%, 55%, 60%, 65%, 70%, 75%, 80%, 85%, 90%, 95% or 98% sequence similarity with the PAIR1 protein;

a PAIR2 protein as shown in SEQ ID NO: 14, a protein having at least 30%, 35%, 40%, 45%, 50%, 55%, 60%, 65%, 70%, 75%, 80%, 85%, 90%, 95% or 98% sequence identity with the PAIR2 protein, or a protein having at least 40%, 45%, 50%, 55%, 60%, 65%, 70%, 75%, 80%, 85%, 90%, 95% or 98% sequence similarity with the PAIR2 protein;

a PAIR3 protein as shown in SEQ ID NO: 15, a protein having at least 30%, 35%, 40%, 45%, 50%, 55%, 60%, 65%, 70%, 75%, 80%, 85%, 90%, 95% or 98% sequence identity with the PAIR3 protein, or a protein having at least 40%, 45%, 50%, 55%, 60%, 65%, 70%, 75%, 80%, 85%, 90%, 95% or 98% sequence similarity with the PAIR3 protein;

a PRD1 protein as shown in SEQ ID NO: 16, a protein having at least 30%, 35%, 40%, 45%, 50%, 55%, 60%, 65%, 70%, 75%, 80%, 85%, 90%, 95% or 98% sequence identity with the PRD1 protein, or a protein having at least 40%, 45%, 50%, 55%, 60%, 65%, 70%, 75%, 80%, 85%, 90%, 95% or 98% sequence similarity with the PRD1 protein;

a PRD2 protein as shown in SEQ ID NO: 17, a protein having at least 30%, 35%, 40%, 45%, 50%, 55%, 60%, 65%, 70%, 75%, 80%, 85%, 90%, 95% or 98% sequence identity with the PRD2 protein, or a protein having at least 40%, 45%, 50%, 55%, 60%, 65%, 70%, 75%, 80%, 85%, 90%, 95% or 98% sequence similarity with the PRD2 protein;

a SPO11-1 protein as shown in SEQ ID NO: 18, a protein having at least 30%, 35%, 40%, 45%, 50%, 55%, 60%, 65%, 70%, 75%, 80%, 85%, 90%, 95% or 98% sequence identity with the SPO11-1 protein, or a protein having at least 40%, 45%, 50%, 55%, 60%, 65%, 70%, 75%, 80%, 85%, 90%, 95% or 98% sequence similarity with the SPO11-1 protein;

a SPO11-2 protein as shown in SEQ ID NO: 19, a protein having at least 30%, 35%, 40%, 45%, 50%, 55%, 60%, 65%, 70%, 75%, 80%, 85%, 90%, 95% or 98% sequence identity with the SPO11-2 protein, or a protein having at least 40%, 45%, 50%, 55%, 60%, 65%, 70%, 75%, 80%, 85%, 90%, 95% or 98% sequence similarity with the SPO11-2 protein;

a SDS protein as shown in SEQ ID NO: 20, a protein having at least 30%, 35%, 40%, 45%, 50%, 55%, 60%, 65%, 70%, 75%, 80%, 85%, 90%, 95% or 98% sequence identity with the SDS protein, or a protein having at least 40%, 45%, 50%, 55%, 60%, 65%, 70%, 75%, 80%, 85%, 90%, 95% or 98% sequence similarity with the SDS protein;

a CRC1 protein as shown in SEQ ID NO: 21, a protein having at least 30%, 35%, 40%, 45%, 50%, 55%, 60%, 65%, 70%, 75%, 80%, 85%, 90%, 95% or 98% sequence identity with the CRC1 protein, or a protein having at least 40%, 45%, 50%, 55%, 60%, 65%, 70%, 75%, 80%, 85%, 90%, 95% or 98% sequence similarity with the CRC1 protein;

a P31$^{comet}$ protein as shown in SEQ ID NO: 22, a protein having at least 30%, 35%, 40%, 45%, 50%, 55%, 60%, 65%, 70%, 75%, 80%, 85%, 90%, 95% or 98% sequence identity with the P31$^{comet}$ protein, or a protein having at least 40%, 45%, 50%, 55%, 60%, 65%, 70%, 75%, 80%, 85%, 90%, 95% or 98% sequence similarity with the P31$^{comet}$ protein;

a MTOPVIB protein as shown in SEQ ID NO: 23, a protein having at least 30%, 35%, 40%, 45%, 50%, 55%, 60%, 65%, 70%, 75%, 80%, 85%, 90%, 95% or 98% sequence identity with the MTOPVIB protein, or a protein having at least 40%, 45%, 50%, 55%, 60%, 65%, 70%, 75%, 80%, 85%, 90%, 95% or 98% sequence similarity with the MTOPVIB protein;

a DFO protein as shown in SEQ ID NO: 24, a protein having at least 30%, 35%, 40%, 45%, 50%, 55%, 60%, 65%, 70%, 75%, 80%, 85%, 90%, 95% or 98% sequence identity with the DFO protein, or a protein having at least 40%, 45%, 50%, 55%, 60%, 65%, 70%, 75%, 80%, 85%, 90%, 95% or 98% sequence similarity with the DFO protein;

the second protein is involved in controlling the adhesion between sister chromosomes during meiosis, and the second protein is a protein selected from the group consisting of:

a REC8 protein as shown in SEQ ID NO: 25, a protein having at least 30%, 35%, 40%, 45%, 50%, 55%, 60%, 65%, 70%, 75%, 80%, 85%, 90%, 95% or 98% sequence identity with the REC8 protein, or a protein having at least 40%, 45%, 50%, 55%, 60%, 65%, 70%, 75%, 80%, 85%, 90%, 95% or 98% sequence similarity with the REC8 protein;

the third protein is involved in the second division of meiosis, and the third protein is a protein selected from the group consisting of:

a OSD1 protein as shown in SEQ ID NO: 26, a protein having at least 30%, 35%, 40%, 45%, 50%, 55%, 60%, 65%, 70%, 75%, 80%, 85%, 90%, 95% or 98% sequence identity with the OSD1 protein, or a protein having at least 40%, 45%, 50%, 55%, 60%, 65%, 70%, 75%, 80%, 85%, 90%, 95% or 98% sequence similarity with the OSD1 protein;

a TAM protein as shown in SEQ ID NO: 27, a protein having at least 30%, 35%, 40%, 45%, 50%, 55%, 60%, 65%, 70%, 75%, 80%, 85%, 90%, 95% or 98% sequence identity with the TAM protein, or a protein having at least 40%, 45%, 50%, 55%, 60%, 65%, 70%, 75%, 80%, 85%, 90%, 95% or 98% sequence similarity with the TAM protein; the TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein;

a TDM1 protein as shown in SEQ ID NO: 28, a protein having at least 30%, 35%, 40%, 45%, 50%, 55%, 60%, 65%, 70%, 75%, 80%, 85%, 90%, 95% or 98% sequence identity with the TDM1 protein, or a protein having at least 40%, 45%, 50%, 55%, 60%, 65%, 70%, 75%, 80%, 85%, 90%, 95% or 98% sequence similarity with the TDM1 protein;

a MTL protein is a MTL protein as shown in SEQ ID NO: 29, a protein having at least 30%, 35%, 40%, 45%, 50%, 55%, 60%, 65%, 70%, 75%, 80%, 85%, 90%, 95% or 98% sequence identity with the MTL protein, or a protein having at least 40%, 45%, 50%, 55%, 60%, 65%, 70%, 75%, 80%, 85%, 90%, 95% or 98% sequence similarity with the MTL protein.

The beneficial effects of the present disclosure will be further illustrated in combination with examples below. Steps or reagents that are not described in detail in the following examples can be achieved by conventional technical means or conventional reagents in the art.

Example 1

1. In this example, the $F_1$ hybrid used is an approved, commercial hybrid rice variety Chunyou84. Chunyou84 is a new japonica-non-indica-restorer intersubspecific hybrid rice combination bred by using the early flowering late japonica sterile line Chunjiang 16A and the indica-japonica intermediate type of wide compatibility and restorer line C84. The hybrid rice has the advantages of high yield potential, high seed production, excellent comprehensive agronomic traits, good blast resistance, and wide adaptability, etc. The genetic transformation background material used in this example is the callus induced by hybrid rice $F_1$ seeds, and has not passed through the sexual reproduction stage. Therefore, the transgenic $T_0$ generation material obtained after transgene is consistent with the hybrid rice $F_1$ plant on the basis of genetic background.

2. Construction of multigene knockout vectors.

The main steps are as follows (Specific details can also be found on CN201510485573.2):

1) Construction of a single target SK-gRNA:

The following four sites were selected as the sites for the CRISPR-Cas9 gene editing system to knock out REC8, OSD1, PAIR1 and MTL sites (PAM sequence indicated by the underline):

```
OSD1 gene knockout site (SEQ ID NO: 1):
CTGCCGCCGACGAGCAACAAGG

PAIR1 gene knockout site (SEQ ID NO: 2):
AAGCAACCCAGTGCACCGCTGG

REC8 gene knockout site (SEQ ID NO: 3):
CCCATGGCACTAAGGCTCTCCG

MTL gene knockout site (SEQ ID NO: 4):
GGTCAACGTCGAGACCGGCAGG
```

Two complementary DNA sequences were designed, respectively: adding GGCA before the forward sequence and adding AAAC before the reverse complementary sequence;

there are two AarI restriction sites on SK-gRNA. After digestion with AarI, a vector with sticky ends was formed; after denaturation and annealing of the designed forward and reverse primers of the target sequence, T4 ligase was ligated to the previously constructed intermediate vector SK-gRNA to form a single target gRNA;

2) The concatenation of multiple gRNAs and the construction of the final binary expression vector:

by using of the characteristics of BglII and BamHI, NheI and XbaI, SalI and XhoI being the isocaudarner, the gRNA was polymerized: SK-gRNA OSD1 was digested with KpnI and XhoI as a vector; SK-gRNA PAIR1 was digested with SalI and XbaI to provide the PAIR1 sgRNA fragment, SK-gRNA REC8 was digested with NheI and BamHI to provide REC8 sgRNA fragment, and SK-gRNA MTL was digested with BglII and KpnI to provide MTL sgRNA fragment, one step rapid polymerization of gRNA within the above 4 was carried out; finally the polymerized gRNA OSD1-gRNA REC8-gRNA PAIR1-gRNA MTL fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA OSD1-gRNA REC8-gRNA PAIR1-gRNA MTL of which the four REC8, OSD1, PAIR1 and MTL genes were knocked out simultaneously, was obtained, and which was used for transgenosis to prepare rice multi-mutant.

3. Production of transgenic plants.

The multi-gene knockout binary expression vector pC1300-Cas9-gRNA OSD1-gRNA REC8-gRNA PAIR1-gRNA MTL was transferred into the *Agrobacterium tumefaciens* strain EHA105 by electroporation, and the binary expression vector was transferred into the callus of rice Chunyou84 using *Agrobacterium tumefaciens*-mediated transformation. The specific method of transformation is to sterilize the embryos of hybrid rice Chunyou84 seeds, and then inoculate same into the medium for inducing callus. After 1 week of culture, vigorously growing, light yellow, and relatively loose embryogenic callus was selected as the recipient of transformation. The EHA105 strain containing pC1300-Cas9-gRNA OSD1-gRNA REC8-gRNA PAIR1-gRNA MTL plasmid was used to infect rice callus, after cultured in the dark at 25° C. for 3 days, the resistant callus and the transgenic seedlings were screened on the selection medium containing 50 mg/l hygromycin. The transgenic seedlings that grow normally on hygromycin selection medium were selected.

4. Identification of quadruple mutants by sequencing

The molecular biology method was used to identify the mutations of target genes. The genomic DNA of transgenic plants was extracted from a single plant by CTAB method, and the target band was amplified by PCR. Primer pair used:

```
OSD1-F (SEQ ID NO: 5):
atctccaggatgcctgaagtgag

OSD1-R (SEQ ID NO: 6):
cctagactgctactcttgctagtgat

PAIR1-F (SEQ ID NO: 7):
ctgtacctgtgcatctaattacag

PAIR1-R (SEQ ID NO: 8):
ccccatatatgtactgagcttgccag

REC8-F (SEQ ID NO: 9):
gcgacgcttcactcgaagatca

REC8-R (SEQ ID NO: 10):
cgccatgcctcgttgatctcaa

MTL-F (SEQ ID NO: 11):
acagtgactagtgacaaacgatcg

MTL-R (SEQ ID NO: 12):
gatcgcgtcagcatgatgcgtgtac
```

The obtained PCR products were sent to a sequencing company, and OSD1-F, PAIR1-F, REC8-F, MTL-F were used as sequencing primers for sequencing. The results were aligned with the wild-type sequence. Sequencing results are bimodal. Degenerate codon strategy was used for analysis (http://dsdecode.scgene.com/ for peak pattern analysis) to obtain mutation information directly. Quadruple mutants whose four genes are all biallelic mutations were screened out.

5. Identification of ploidy and genotype-fixed plants in the first filial generation.

1) Among the first filial generation plants of the quadruple mutant plants identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

FIG. 4A shows the cell ploidy test results of the F1 generation plant Chunyou84; and FIG. 4B shows the cell ploidy test results of the heterosis fixed plants.

2) Whole genome sequencing.

Figure 5:
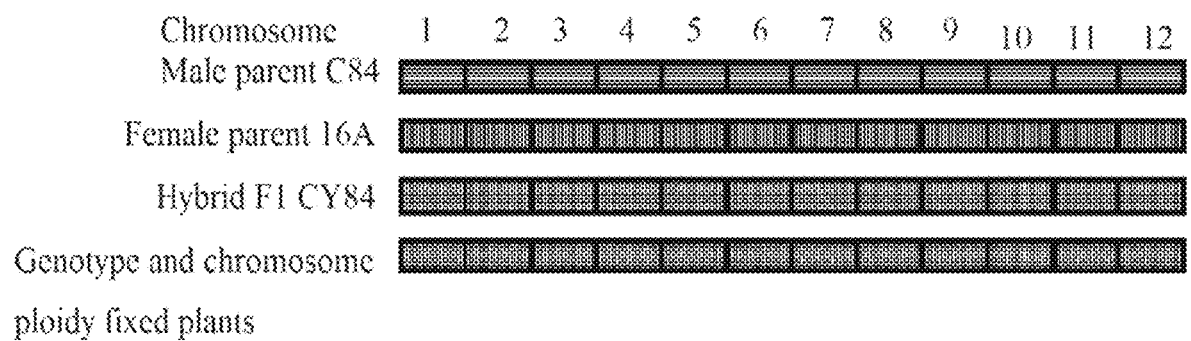
FIG. 5 shows the results of whole gene sequencing of the male parent C84, female parent 16A, hybrid Chunyou84 (CY84), genotype and chromosome ploidy fixed plants in Example 1.

The leaves of two parents Chunjiang 16A and C84, Chunyou84 and the ploidy fixed first filial generation (4 plants were randomly selected) were selected, and DNA was extracted for whole genome sequencing. According to the whole genome sequencing results (FIG. 5): there are many different homozygous genotypes between Chunjiang 16A and C84. The genotypes of the hybrid Chunyou84 at these sites are in a heterozygous state having genotypes of both Chunjiang 16A and C84. The genotypes of the 4 plants tested were consistent with Chunyou84, and all were heterozygous. From the molecular biology point of view, it was proved that the genotype was completely consistent with the hybrid mother cell.

Example 2

1. In this example, the maintainer line Chunjiang 16B and the indica-japonica intermediate type of wide compatibility and restorer line C84 were used. The genetic transformation background material used in this example is the callus induced by parent seeds.

2. Construction of multigene knockout vectors.

The main steps are as follows

1) Construction of a single target SK-gRNA:

The following four sites were selected as the sites for the CRISPR-Cas9 gene editing system to knock out REC8, OSD1, PAIR1 and MTL sites (PAM sequence indicated by the underline):

```
OSD1 gene knockout site (SEQ ID NO: 1):
CTGCCGCCGACGAGCAACAAGG

PAIR1 gene knockout site (SEQ ID NO: 2):
AAGCAACCCAGTGCACCGCTGG

REC8 gene knockout site (SEQ ID NO: 3):
CCCATGGCACTAAGGCTCTCCG

MTL gene knockout site (SEQ ID NO: 4):
GGTCAACGTCGAGACCGGCAGG
```

Two complementary DNA sequences were designed, respectively: adding GGCA before the forward sequence and adding AAAC before the reverse complementary sequence;

there are two AarI restriction sites on SK-gRNA. After digestion with AarI, a vector with sticky ends was formed; after denaturation and annealing of the designed forward and reverse primers of the target sequence, T4 ligase was ligated to the previously constructed intermediate vector SK-gRNA to form a single target gRNA;

4) The concatenation of multiple gRNAs and the construction of the final binary expression vector:

by using of the characteristics of BglII and BamHI, NheI and XbaI, SalI and XhoI being the isocaudarner, the gRNA was polymerized: SK-gRNA OSD1 was digested with KpnI and XhoI as a vector; SK-gRNA PAIR1 was digested with SalI and XbaI to provide the PAIR1 sgRNA fragment, SK-gRNA REC8 was digested with NheI and BamHI to provide REC8 sgRNA fragment, and SK-gRNA MTL was digested with BglII and KpnI to provide MTL sgRNA fragment, one step rapid polymerization of gRNA within the above 4 was carried out; finally the polymerized gRNA OSD1-gRNA REC8-gRNA PAIR1-gRNA MTL fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA OSD1-gRNA REC8-gRNA PAIR1-gRNA MTL of which the four REC8, OSD1, PAIR1 and MTL genes were knocked out simultaneously, was obtained, and which was used for transgenosis to prepare rice multi-mutant.

3. Production of transgenic plants.

The multi-gene knockout binary expression vector pC1300-Cas9-gRNA OSD1-gRNA REC8-gRNA PAIR1-gRNA MTL was transferred into the *Agrobacterium tumefaciens* strain EHA105 by electroporation, and the binary expression vector was transferred into the callus of Chunjiang 16B and C84 using *Agrobacterium tumefaciens*-mediated transformation. The specific method of transformation is to sterilize the embryos of seeds, and then inoculate same into the callus-inducing medium. After 1 week of culture, vigorously growing, light yellow, and relatively loose embryogenic callus was selected as the recipient of transformation. The EHA105 strain containing pC1300-Cas9-gRNA OSD1-gRNA REC8-gRNA PAIR1-gRNA MTL plasmid was used to infect rice callus, after cultured in the dark at 25° C. for 3 days, the resistant callus and the transgenic seedlings were screened on the selection medium containing 50 mg/l hygromycin. The transgenic seedlings that grow normally on hygromycin selection medium were selected.

4. Chunjiang 16B and C84 materials whose all four genes are heterozygous mutation were identified by sequencing, and then hybridized them to screen out hybrid plants whose four genes are mutations.

The molecular biology method was used to identify the mutations of target genes. The genomic DNA of transgenic plants was extracted from a single plant by CTAB method, and the target band was amplified by PCR. Primer pair used:

```
OSD1-F (SEQ ID NO: 5):
atctccaggatgcctgaagtgag

OSD1-R (SEQ ID NO: 6):
cctagactgctactcttgctagtgat

PAIR1-F (SEQ ID NO: 7):
ctgtacctgtgcatctaattacag

PAIR1-R (SEQ ID NO: 8):
ccccatcttatgtactgagcttgccag

REC8-F (SEQ ID NO: 9):
gcgacgcttcactcgaagatca

REC8-R (SEQ ID NO: 10):
cgccatgcctcgttgatctcaa

MTL-F (SEQ ID NO: 11):
acagtgactagtgacaaacgatcg

MTL-R (SEQ ID NO: 12):
gatcgcgtcagcatgatgcgtgtac
```

The obtained PCR products were sent to a sequencing company, and OSD1-F, PAIR1-F, REC8-F, MTL-F were used as sequencing primers for sequencing. The results were aligned with the wild-type sequence to obtain the mutation information directly.

After screening out the Chunjiang 16B and C84 materials with heterozygous mutations, intercrossed them and screened out hybrid plants with biallelic mutations in the F1 generation.

5. The seeds from hybrid plants were collected, and the ploidy and genotype-fixed plants were identified in the first filial generation.

1) Among the first filial generation plants of the triple mutant plants identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

2) Whole genome sequencing.

The leaves of two parents Chunjiang 16B and C84, Chunyou84 and the ploidy fixed first filial generation (2 plants were randomly selected) plants were selected, and DNA was extracted for whole genome sequencing. According to the whole genome sequencing results: there are many different homozygous genotypes between Chunjiang 16B and C84. The genotypes of the hybrid Chunyou84 at these sites are in a heterozygous state having genotypes of both Chunjiang 16B and C84. The genotypes of the 2 plants tested were consistent with Chunyou84, and all were heterozygous. From the molecular biology point of view, it was proved that the genotype was completely consistent with the hybrid mother cell.

Example 3

1. In this example, the $F_1$ hybrid used is an approved, commercial hybrid rice variety Chunyou84. Chunyou84 is a new japonica-non-indica-restorer intersubspecific hybrid rice combination bred by using the sterile line Chunjiang 16A and the indica-japonica intermediate type of wide compatibility and restorer line C84. The hybrid rice has the advantages of high yield potential, high seed production, excellent comprehensive agronomic traits, good blast resistance, and wide adaptability, etc. The genetic transformation background material used in this example is the callus induced by hybrid rice $F_1$ seeds, and has not passed through the sexual reproduction stage. Therefore, the transgenic $T_0$ generation material obtained after transgene is consistent with the hybrid rice $F_1$ plant on the basis of genetic background.

2. Construction of multigene knockout vectors.

The main steps are as follows

1) Construction of a single target SK-gRNA:

The following three sites were selected as the sites for the CRISPR-Cas9 gene editing system to knock out REC8, OSD1, and PAIR1 (PAM sequence indicated by the underline):

```
OSD1 gene knockout site (SEQ ID NO: 1):
CTGCCGCCGACGAGCAACAAGG

PAIR1 gene knockout site (SEQ ID NO: 2):
AAGCAACCCAGTGCACCGCTGG

REC8 gene knockout site (SEQ ID NO: 3):
CCCATGGCACTAAGGCTCTCCG
```

Two complementary DNA sequences were designed, respectively: adding GGCA before the forward sequence and adding AAAC before the reverse complementary sequence;

there are two AarI restriction sites on SK-gRNA. After digestion with AarI, a vector with sticky ends was formed; after denaturation and annealing of the designed forward and reverse primers of the target sequence, T4 ligase was ligated to the previously constructed intermediate vector SK-gRNA to form a single target gRNA;

2) The concatenation of three gRNAs and the construction of the final binary expression vector:

by using of the characteristics of BglII and BamHI, NheI and XbaI, SalI and XhoI being the isocaudarner, the gRNA was polymerized; finally the polymerized gRNA OSD1-gRNA REC8-gRNA PAIR1 fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA OSD1-gRNA REC8-gRNA PAIR1 of which the three REC8, OSD1 and PAIR1 genes were knocked out simultaneously, was obtained, and which was used for transgenosis to prepare rice multi-mutant.

3. Production of transgenic plants.

The multi-gene knockout binary expression vector pC1300-Cas9-gRNA OSD1-gRNA REC8-gRNA PAIR1-gRNA was transferred into the *Agrobacterium tumefaciens* (*Agrobacterium tumefaciens*) strain EHA105 by electroporation, and the binary expression vector was transferred into the callus of rice Chunyou84 using *Agrobacterium tumefaciens*-mediated transformation. The specific method of transformation is to sterilize the embryos of hybrid rice Chunyou84 seeds, and then inoculate same into the medium for inducing callus. After 1 week of culture, vigorously growing, light yellow, and relatively loose embryogenic callus was selected as the recipient of transformation. The EHA105 strain containing pC1300-Cas9-gRNA OSD1-gRNA REC8-gRNA PAIR1 plasmid was used to infect rice callus, after cultured in the dark at 25° C. for 3 days, the resistant callus and the transgenic seedlings were screened on the selection medium containing 50 mg/l hygromycin. The transgenic seedlings that grow normally on hygromycin selection medium were selected.

4. Identification of triple mutants by Sequencing

The molecular biology method was used to identify the mutations of target genes. The genomic DNA of transgenic plants was extracted from a single plant by CTAB method, and the target band was amplified by PCR. Primer pair used:

```
OSD1-F (SEQ ID NO: 5):
atctccaggatgcctgaagtgag

OSD1-R (SEQ ID NO: 6):
cctagactgctactcttgctagtgat

PAIR1-F (SEQ ID NO: 7):
ctgtacctgtgcatctaattacag

PAIR1-R (SEQ ID NO: 8):
ccccatatatgtactgagcttgccag

REC8-F (SEQ ID NO: 9):
gcgacgcttcactcgaagatca

REC8-R (SEQ ID NO: 10):
cgccatgcctcgttgatctcaa
```

The obtained PCR products were sent to a sequencing company, and OSD1-F, PAIR1-F, and REC8-F were used as sequencing primers for sequencing. The results were aligned with the wild-type sequence. Sequencing results are bimodal. Degenerate codon strategy was used for analysis (http://dsdecode.scgene.com/ for peak pattern analysis) to obtain mutation information directly.

Among them, mutants with biallelic mutations at these 3 sites are plants that can produce gametes whose genotype and chromosome ploidy are consistent with somatic cells.

5. Using the triple mutant as the female parent, pollen from other haploid inducer plant was pollinated to induce the female gametes to develop into seeds, and a large number of hybrids that maintained heterosis were obtained.

6. Identification of ploidy and genotype-fixed plants in the first filial generation.

1) Among the first filial generation plants of the triple mutant plants identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

2) Whole genome sequencing.

The leaves of two parents Chunjiang 16A and C84, Chunyou84 and the ploidy fixed first filial generation (4 plants were randomly selected) were selected, and DNA was extracted for whole genome sequencing. According to the whole genome sequencing results: there are many different homozygous genotypes between Chunjiang 16A and C84. The genotypes of the hybrid Chunyou84 at these sites are in a heterozygous state having genotypes of both Chunjiang 16A and C84. The genotypes of the 4 plants tested were consistent with Chunyou84, and all were heterozygous. From the molecular biology point of view, it was proved that the genotype was completely consistent with the hybrid mother cell.

Example 4

1. In this example, the $F_1$ hybrid used is an approved, commercial hybrid rice variety Chunyou84. Chunyou84 is a new japonica-non-indica-restorer intersubspecific hybrid rice combination bred by using the sterile line Chunjiang 16A and the indica-japonica intermediate type of wide compatibility and restorer line C84. The hybrid rice has the advantages of high yield potential, high seed production, excellent comprehensive agronomic traits, good blast resistance, and wide adaptability, etc. The genetic transformation background material used in this example is the callus induced by hybrid rice $F_1$ seeds, and has not passed through the sexual reproduction stage. Therefore, the transgenic $T_0$ generation material obtained after transgene is consistent with the hybrid rice $F_1$ plant on the basis of genetic background.

2. Construction of multigene knockout vectors.

The main steps are as follows

1) Construction of a single target SK-gRNA:

The following three sites were selected as the sites for the CRISPR-Cas9 gene editing system to knock out REC8, OSD1, and PAIR1 (PAM sequence indicated by the underline):

```
OSD1 gene knockout site (SEQ ID NO: 1):
CTGCCGCCGACGAGCAACAAGG

PAIR1 gene knockout site (SEQ ID NO: 2):
AAGCAACCCAGTGCACCGCTGG

REC8 gene knockout site (SEQ ID NO: 3):
CCCATGGCACTAAGGCTCTCCG
```

Two complementary DNA sequences were designed, respectively: adding GGCA before the forward sequence and adding AAAC before the reverse complementary sequence;

there are two AarI restriction sites on SK-gRNA. After digestion with AarI, a vector with sticky ends was formed; after denaturation and annealing of the designed forward and reverse primers of the target sequence, T4 ligase was ligated to the previously constructed intermediate vector SK-gRNA to form a single target gRNA;

2) The concatenation of three gRNAs and the construction of the final binary expression vector:

by using of the characteristics of BglII and BamHI, NheI and XbaI, SalI and XhoI being the isocaudarner, the gRNA was polymerized; finally the polymerized gRNA OSD1-gRNA REC8-gRNA PAIR1 fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA OSD1-gRNA REC8-gRNA PAIR1 of which the three REC8, OSD1 and PAIR1 genes were knocked out simultaneously, was obtained, and which was used for transgenosis to prepare rice multi-mutant.

3. Production of transgenic plants.

The multi-gene knockout binary expression vector pC1300-Cas9-gRNA OSD1-gRNA REC8-gRNA PAIR1 was transferred into the *Agrobacterium tumefaciens* (*Agrobacterium tumefaciens*) strain EHA105 by electroporation, and the binary expression vector was transferred into the callus of rice Chunyou84 using *Agrobacterium tumefaciens*-mediated transformation. The specific method of transformation is to sterilize the embryos of hybrid rice Chunyou84 seeds, and then inoculate same into the medium for inducing callus. After 1 week of culture, vigorously growing, light yellow, and relatively loose embryogenic callus was selected as the recipient of transformation. The EHA105 strain containing pC1300-Cas9-gRNA OSD1-gRNA REC8-gRNA PAIR1 plasmid was used to infect rice callus, after cultured in the dark at 25° C. for 3 days, the resistant callus and the transgenic seedlings were screened on the selection medium containing 50 mg/l hygromycin. The transgenic seedlings that grow normally on hygromycin selection medium were selected.

4. Identification of triple mutants by Sequencing

The molecular biology method was used to identify the mutations of target genes. The genomic DNA of transgenic plants was extracted from a single plant by CTAB method, and the target band was amplified by PCR. Primer pair used:

```
OSD1-F (SEQ ID NO: 5):
atctccaggatgcctgaagtgag

OSD1-R (SEQ ID NO: 6):
cctagactgctactcttgctagtgat

PAIR1-F (SEQ ID NO: 7):
ctgtacctgtgcatctaattacag
```

-continued

```
PAIR1-R (SEQ ID NO: 8):
ccccatcttatgtactgagcttgccag

REC8-F (SEQ ID NO: 9):
gcgacgcttcactcgaagatca

REC8-R (SEQ ID NO: 10):
cgccatgcctcgttgatctcaa
```

The obtained PCR products were sent to a sequencing company, and OSD1-F, PAIR1-F, and REC8-F were used as sequencing primers for sequencing. The results were aligned with the wild-type sequence. Sequencing results are bimodal. Degenerate codon strategy was used for analysis (http://dsdecode.scgene.com/ for peak pattern analysis) to obtain mutation information directly.

Among them, mutants with biallelic mutations at these 3 sites are plants that can produce gametes whose genotype and chromosome ploidy are consistent with somatic cells.

5. After the triple mutants developed to a certain stage, the anthers or pollen were taken by aseptic operation, respectively, and inoculated on the artificially configured anther medium to induce the formation of callus, and then the plants were obtained through tissue culture.

6. Identification of ploidy and genotype-fixed plants in the tissue culture plants.

1) Among the first filial generation plants of the triple mutant plants identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

2) Whole genome sequencing.

The leaves of two parents Chunjiang 16A and C84, Chunyou84 and the ploidy fixed first filial generation (4 plants were randomly selected) were selected, and DNA was extracted for whole genome sequencing. According to the whole genome sequencing results: there are many different homozygous genotypes between Chunjiang 16A and C84. The genotypes of the hybrid Chunyou84 at these sites are in a heterozygous state having genotypes of both Chunjiang 16A and C84. The genotypes of the 4 plants tested were consistent with Chunyou84, and all were heterozygous. From the molecular biology point of view, it was proved that the genotype was completely consistent with the hybrid mother cell.

Example 5

1. In this example, the $F_1$ hybrid used is an approved, commercial hybrid rice variety Chunyou84. Chunyou84 is a new japonica-non-indica-restorer intersubspecific hybrid rice combination bred by using the sterile line Chunjiang 16A and the indica-japonica intermediate type of wide compatibility and restorer line C84. The hybrid rice has the advantages of high yield potential, high seed production, excellent comprehensive agronomic traits, good blast resistance, and wide adaptability, etc. The genetic transformation background material used in this example is the callus induced by hybrid rice $F_1$ seeds, and has not passed through the sexual reproduction stage. Therefore, the transgenic $T_0$ generation material obtained after transgene is consistent with the hybrid rice $F_1$ plant on the basis of genetic background.

2. Construction of multigene knockout vectors.

The main steps are as follows

1) Construction of a single target SK-gRNA:

The following three sites were selected as the sites for the CRISPR-Cas9 gene editing system to knock out REC8, OSD1, and PAIR1 (PAM sequence indicated by the underline):

```
OSD1 gene knockout site (SEQ ID NO: 1):
CTGCCGCCGACGAGCAACAAGG

PAIR1 gene knockout site (SEQ ID NO: 2):
AAGCAACCCAGTGCACCGCTGG

REC8 gene knockout site (SEQ ID NO: 3):
CCCATGGCACTAAGGCTCTCCG
```

Two complementary DNA sequences were designed, respectively: adding GGCA before the forward sequence and adding AAAC before the reverse complementary sequence;

there are two AarI restriction sites on SK-gRNA. After digestion with AarI, a vector with sticky ends was formed; after denaturation and annealing of the designed forward and reverse primers of the target sequence, T4 ligase was ligated to the previously constructed intermediate vector SK-gRNA to form a single target gRNA;

2) The concatenation of three gRNAs and the construction of the final binary expression vector:

by using of the characteristics of BglII and BamHI, NheI and XbaI, SalI and XhoI being the isocaudarner, the gRNA was polymerized; finally the polymerized gRNA OSD1-gRNA REC8-gRNA PAIR1 fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA OSD1-gRNA REC8-gRNA PAIR1 of which the three REC8, OSD1 and PAIR1 genes were knocked out simultaneously, was obtained, and which was used for transgenosis to prepare rice multi-mutant.

3. Production of transgenic plants.

The multi-gene knockout binary expression vector pC1300-Cas9-gRNA OSD1-gRNA REC8-gRNA PAIR1 was transferred into the Agrobacterium tumefaciens (Agrobacterium tumefaciens) strain EHA105 by electroporation, and the binary expression vector was transferred into the callus of rice Chunyou84 using Agrobacterium tumefaciens-mediated transformation. The specific method of transformation is to sterilize the embryos of hybrid rice Chunyou84 seeds, and then inoculate same into the medium for inducing callus. After 1 week of culture, vigorously growing, light yellow, and relatively loose embryogenic callus was selected as the recipient of transformation. The EHA105 strain containing pC1300-Cas9-gRNA OSD1-gRNA REC8-gRNA PAIR1 plasmid was used to infect rice callus, after cultured in the dark at 25° C. for 3 days, the resistant callus and the transgenic seedlings were screened on the selection medium containing 50 mg/l hygromycin. The transgenic seedlings that grow normally on hygromycin selection medium were selected.

4. Identification of triple mutants by Sequencing

The molecular biology method was used to identify the mutations of target genes. The genomic DNA of transgenic plants was extracted from a single plant by CTAB method, and the target band was amplified by PCR. Primer pair used:

```
OSD1-F (SEQ ID NO: 5):
atctccaggatgcctgaagtgag

OSD1-R (SEQ ID NO : 6):
cctagactgctactcttgctagtgat

PAIR1-F (SEQ ID NO: 7):
ctgtacctgtgcatctaattacag

PAIR1-R (SEQ ID NO: 8):
ccccatcttatgtactgagcttgccag

REC8-F (SEQ ID NO: 9):
gcgacgcttcactcgaagatca

REC8-R (SEQ ID NO: 10):
cgccatgcctcgttgatctcaa
```

The obtained PCR products were sent to a sequencing company, and OSD1-F, PAIR1-F, and REC8-F were used as sequencing primers for sequencing. The results were aligned with the wild-type sequence. Sequencing results are bimodal. Degenerate codon strategy was used for analysis (http://dsdecode.scgene.com/ for peak pattern analysis) to obtain mutation information directly.

Among them, mutants with biallelic mutations at these 3 sites are plants that can produce gametes whose genotype and chromosome ploidy are consistent with somatic cells.

5. Chemically induced parthenogenesis

The rice material that knocked out the three genes of REC8, OSD1 and PAIR1 simultaneously was taken. Before the rice bloomed, emasculation by cutting glume was carried out according to the general hybridization technique, and then the rice ears were immersed in the treatment solution of 5-50 mg/L maleic hydrazide or 2-20 mg/L 6-benzylamino adenine for 2-3 minutes, bagging tightly to prevent pollen from entering. Twenty days after the treatment, immature embryos or grains were taken and cultured to obtain parthenogenetic plants.

6. Identification of ploidy and genotype-fixed plants in the first filial generation.

1) Among the first filial generation plants of the triple mutant plants identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

2) Whole genome sequencing.

The leaves of two parents Chunjiang 16A and C84, Chunyou84 and the ploidy fixed first filial generation (4 plants were randomly selected) were selected, and DNA was extracted for whole genome sequencing. According to the whole genome sequencing results: there are many different homozygous genotypes between Chunjiang 16A and C84. The genotypes of the hybrid Chunyou84 at these sites are in a heterozygous state having genotypes of both Chunjiang 16A and C84. The genotypes of the 4 plants tested were consistent with Chunyou84, and all were heterozygous. From the molecular biology point of view, it was proved that the genotype was completely consistent with the hybrid mother cell.

Example 6

1. Mutant mutagenesis and screening

In soybean variety Zhonghuang39, through EMS mutagenesis, the progenies were screened by high-throughput sequencing technology to obtain plants whose REC8 and OSD1 are heterozygous mutations, respectively. Through the hybridization between heterozygous plants and the progeny screening, plants whose REC8 and OSD1 are heterozygous mutations were obtained; in soybean variety Qihuang34, through EMS mutagenesis, the progenies were screened by high-throughput sequencing technology to obtain plants whose SPO11-1 and CENH3 are heterozygous mutations, respectively. Through the hybridization between heterozygous plants and the progeny screening, plants whose SPO11-1 and CENH3 are heterozygous mutations were obtained; the plants whose REC8 and OSD1 are heterozygous mutations and the plants whose SPO11-1 and CENH3 are heterozygous mutations were hybridized, the progenies were screened to obtain plants whose all four genes are heterozygous mutations.

2. Construction of transgenic vector

A binary vector with oocyte specifically-expressed EC1.2 to drive wild-type CENH3 expression was constructed, and the vector was transformed into plants whose four genes are all heterozygous mutations; the self-bred progenies of plants were identified and screened to obtain a single plant whose REC8, OSD1, SPO11-1 and CENH3 genes are all homozygous mutations and has Ec1.2:: CenH3 transgenic components, the self-bred seeds of the plant were harvested.

3. Identification of ploidy and genotype-fixed plants in the first filial generation.

1) Among the first filial generation plants, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.

2) Genotype testing.

The ploidy fixed progeny (4 plants were randomly selected) and the leaves of the previous generation plants were selected to extract DNA; 16 heterozygous sites were randomly selected from the previous generation hybrid materials, and the detection primers were designed. Genotype testing was performed on the first filial generation plants, and it was found that the genotypes of the 4 plants at 16 sites were exactly the same as those of the previous generation, that is, all were heterozygous. From the molecular biology point of view, it was proved that the heterozygous genotype did not undergo recombination or separation.

Example 7

1. In this Example, the $F_1$ hybrid used is the maize hybrid Jiahe158, which is a combination of LD140×LD975.
2. Construction of multigene knockout vectors.
The main steps are as follows
1) Construction of a single target SK-gRNA:
The following four sites were selected as the sites for the CRISPR-Cas9 gene editing system to knock out maize REC8, OSD1, PAIR1 and MTL sites (PAM sequence indicated by the underline):

```
ZmOSD1 gene knockout site (SEQ ID NO: 30):
TCTGCCTGTACTGGAGTTATTGG

ZmPAIR1 gene knockout site (SEQ ID NO: 31):
GGATTGCTGCGACAGCGGCTGGG

ZmREC8 gene knockout site (SEQ ID NO: 32):
GGAAGTCCCACGAGTAATTATGG

ZmMTL gene knockout site (SEQ ID NO: 33):
GGAAGGCGAGGATGGTTCCCGGG
```

2) The concatenation of multiple gRNAs and the construction of the final binary expression vector:
by using of the characteristics of BglII and BamHI, NheI and XbaI, SalI and XhoI being the isocaudarner, the gRNA was polymerized: SK-gRNA ZmOSD1 was digested with KpnI and XhoI as a vector, SK-gRNA ZmPAIR1 was digested with KpnI and XhoI to provide the ZmPAIR1 sgRNA fragment, SK-gRNA ZmREC8 was digested with NheI and BamHI to provide ZmREC8 sgRNA fragment, and SK-gRNA ZmMTL was digested with BglII and KpnI to provide ZmMTL sgRNA fragment, one step rapid polymerization of gRNA within the above 4 was carried out; finally the polymerized gRNA ZmOSD1-gRNA ZmREC8-gRNA ZmPAIR1-gRNA ZmMTL fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA ZmOSD1-gRNA ZmREC8-gRNA ZmPAIR1-gRNA ZmMTL of which the four maize REC8, OSD1, PAIR1 and MTL genes were knocked out simultaneously, was obtained, and which was used for transgenosis to prepare maize multi-mutant.
3. Production of transgenic plants.
The maize multigene knockout vector obtained in the previous step was transferred into *Agrobacterium tumefaciens* strain LBA4404 by electroporation, and this binary expression vector was transferred into the callus of maize hybrid Jiahe158 by *Agrobacterium tumefaciens*-mediated transformation. After the maize was pollinated, it was bagged artificially for 9-12 days, the female ears were taken and peeled off the bracts, and were sprayed 75% alcohol when each bract was peeled off to disinfect the surface, and a size of 1.0-1.2 mm of immature embryos was picked under the clean bench with a blade and then placed in a hyperosmotic solution for later use, and the time in the hyperosmotic solution should not exceed 1 hour. When the *Agrobacterium tumefaciens* was cultivated to an OD600 value of 0.8, the bacteria were collected by centrifugation, using 1 mol/L of suspension, after resuspended, acetosyringone was added to a final concentration of 200 μmol/L, this bacteria solution was used to infect the immature embryos for 5 minutes, then the mixture was transferred to a co-culture medium and cultured in the dark at 25° C. for 7 days. The immature embryos were transferred to a selection medium containing 15 mg/l hygromycin and a regeneration medium in the later period to screen resistant callus and transgenic plants.
4. Identification of quadruple mutants by sequencing
The CTAB method was used to extract genomic DNA of transgenic maize from a single plant, and Hi-Tom was used to identify the mutation of the target gene (specific details can be found in CN201710504178.3).
5. Identification of ploidy and genotype-fixed maize plants in the first filial generation.
1) Among the first filial generation plants of the quadruple mutant maize identified, flow cytometry was used to screen the cell ploidy, and the plants having the same cell ploidy as the parent plants were obtained.
The specific method is as follows:
A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 μL of pre-cooled PI (1 mg/ml) and RNase A (1 mg/ml) for 10 min in the dark, tested on the machine to screen out diploid plants.
2) Whole genome sequencing.
The leaves of two parents LD140 and LD975, Jiahe158 and the ploidy fixed first filial generation maize plants were selected, and DNA was extracted for whole genome sequencing. The genotypes of the first filial generation maize plants tested were consistent with Jiahe158, and they are all heterozygous. From the molecular biology point of view, it was proved that the genotypes were completely consistent with the hybrid mother cells.

Example 8

1. In this example, the $F_1$ hybrid used is the tomato hybrid Elisa, the female parent is the low-temperature-tolerant inbred line "Syi2-4", and the male parent is the high-quality disease-resistant inbred line "S28".
2. Construction of multigene knockout vectors.
The main steps are as follows
1) Construction of a single target SK-gRNA:
The following four sites were selected as the sites for the CRISPR-Cas9 gene editing system to knock out tomato REC8, OSD1, SPO11 and MTL sites (PAM sequence indicated by the underline):

```
SlOSD1 gene knockout site (SEQ ID NO: 34):
CAGAAGCAGGGAGAATGGCAGG

SlSPO11 gene knockout site (SEQ ID NO: 35):
TGAGGATCTCGCTCGAGGTAGG

SlREC8 gene knockout site (SEQ ID NO: 36):
GCACAGGAGGAACCTGCTAAGG

SlMTL gene knockout site (SEQ ID NO: 37):
TGATTGCCGGAACGAGCACCGG
```

2) The concatenation of multiple gRNAs and the construction of the final binary expression vector:
by using of the characteristics of BglII and BamHI, NheI and XbaI, SalI and XhoI being the isocaudarner, the gRNA was polymerized: SK-gRNA SlOSD1 was digested with KpnI and XhoI as a vector, SK-gRNA SlSPO11 was digested with SalI and XbaI to provide the SlSPO11 sgRNA fragment, SK-gRNA SlREC8 was digested with NheI and BamHI to provide SlREC8 sgRNA fragment, and SK-gRNA SlMTL was digested with BglII and KpnI to provide SlMTL sgRNA fragment, one step rapid polymerization of gRNA within the above 4 was carried out; finally the polymerized gRNA SlOSD1-gRNA S1REC8-gRNA SlPAIR1-gRNA SlMTL fragment was digested with KpnI and BglII, and the fragments were recovered, and ligated into the binary vector pC1300-Cas9 expressing Cas9 protein (between KpnI and BamHI sites), and finally the multigene knockout vector pC1300-Cas9-gRNA SlOSD1-gRNA SlREC8-gRNA SlSPO11-gRNA SlMTL of which the four tomato REC8, OSD1, SPO11 and MTL genes were knocked out simultaneously, was obtained, and which was used for transgenosis to prepare tomato multi-mutant.

3. Production of transgenic plants.

The tomato multigene knockout vector obtained in the previous step was transferred into *Agrobacterium tumefaciens* strain EHA105 by electroporation through leaf disc method, and this binary expression vector was transferred into the callus of tomato hybrid Elisa by *Agrobacterium tumefaciens*-mediated transformation.

The tomato seeds were aseptically treated and sown on ½ MS medium, cultivated in the dark for 2-3 days, after germination, cultivated under light. After 10-12 days, when the cotyledons of the seedlings were fully expanded, but no true leaves were formed, the cotyledons were selected as explants, the two ends of the cotyledons were cut off, the middle part was divided into two horizontally, and the small pieces were the leaf discs. The leaf discs were inoculated in a pre-culture medium with the leaves facing up and pre-cultured for 2 days. The pre-cultured cotyledon leaf disc was soaked with the prepared *Agrobacterium tumefaciens* bacteria solution, which was fully infiltrated for 5 minutes, the leaf disc was properly blotted up with sterile filter paper, with the back of the leaf facing up, cultivated in the dark for 48-72 hours at a culture temperature of 28° C. The leaf discs co-cultured with *Agrobacterium tumefaciens* were transferred to sterile medium and cultured under light. After 5 days, the leaf discs were transferred to the screening medium, and transferred once every 14 days. When the resistant bud grew to about 2 cm, it was cut from the explant and transferred to the rooting medium. After the root system was developed, it was transplanted to the soil.

4. Identification of quadruple mutants by sequencing

The CTAB method was used to extract genomic DNA of transgenic tomato from a single plant, and Hi-Tom was used to identify the mutation of the target gene (specific details can be found in CN201710504178.3).

5. Identification of ploidy and genotype-fixed tomato plants in the first filial generation.

1) Among the first filial generation plants of the quadruple mutant tomato identified, flow cytometry was used to screen the cell ploidy, and the plants having the same cell ploidy as the parent plants were obtained.

The specific method is as follows:

A certain amount of plant tissue was put into a glass petri dish, 1-2 ml of plant lysis buffer LB01 was added, the same was chopped with a blade (this operation was always performed on ice); the dissociation solution in the petri dish was aspirated, and filtered through a 50 μm nylon net into a centrifuge tube; centrifuged at 1,200 rpm, 4° C. for 5 min; the supernatant was discarded, 450 μl of LB01 was added, which was stained with 25 uL of pre-cooled PI (1 mg/ml) and RNase A (1 mg/ml) for 10 min in the dark, tested on the machine to screen out diploid plants.

2) Whole genome sequencing.

The leaves of two parents "Syi2-4" and "S28", tomato hybrid Elisa and the ploidy fixed first filial generation tomato plants were selected, and DNA was extracted for whole genome sequencing. The genotypes of the first filial generation tomato plants tested were consistent with Elisa, and they are all heterozygous. From the molecular biology point of view, it was proved that the genotypes were completely consistent with the hybrid mother cells.

In addition, all the vectors and reagents used in this example are included in the kit of this example.

The above description is only the preferred embodiment of the present disclosure, and is not intended to limit the present disclosure, and various modifications and changes can be made to the present disclosure for those skilled in the art. Any modification, equivalent substitution, improvement, and the like made within the spirit and principle of the present disclosure shall be included into the protection scope of the present disclosure.

What is claimed is:

1. A method for maintaining plant heterosis, wherein it comprises the following steps:
    S1, transforming the meiosis of germ cells of hybrids into mitosis-like to obtain gametes whose genotype and chromosome ploidy are consistent with hybrids by using gene mutations or gene engineering technology; the S1 comprises editing proteins involved in meiosis in plants to realize the transformation of meiosis of germ cells into mitosis-like by using gene mutation or gene engineering technology; when the plant is rice, the proteins comprise a OSD1 protein as shown in SEQ ID NO:26, a PAIR1 protein as shown in SEQ ID NO:13 and a REC8 protein as shown in SEQ ID NO:25 and
    S2, knocking out an MTL gene as shown in SEQ ID NO:29 by using gene engineering technology to induce the gametes whose and chromosome ploidy are consistent with hybrids to develop into seeds or plants.

2. The method according to claim 1, wherein the gene mutation comprises directed mutagenesis; the directed mutagenesis comprises gene editing technology, the gene editing technology comprises CRISPR/Cas gene editing technology, CRISPR/Cpf1 gene editing technology, TALEN gene editing technology, homing endonuclease gene editing technology and ZFN gene editing technology; the gene engineering technology comprises transgene technology to induce specific expression, ectopic expression or gene silencing of genes.

3. The method according to claim 1, wherein the S1 comprises using hybrid seeds inducing the callus and editing genes by using gene mutation or gene engineering technology to transform the meiosis of germ cells of transgenic plant into mitosis-like to obtain gametes whose genotype and chromosome ploidy are consistent with hybrids.

4. The method according to claim 1, wherein the S1 comprises editing the parent of the hybrid seeds using gene mutation or gene engineering technology, and then obtaining the hybrid through interparental hybridization, so as to obtain hybrid gametes whose meiosis of germ cells is transformed into mitosis-like.

* * * * *